US009532519B2

(12) United States Patent
Ogawa et al.

(10) Patent No.: US 9,532,519 B2
(45) Date of Patent: Jan. 3, 2017

(54) PLANT GROWTH REGULATOR AND USE THEREOF

(71) Applicant: Japan Science and Technology Agency, Kawaguchi (JP)

(72) Inventors: Kenichi Ogawa, Kaga-gun (JP); Kenji Henmi, Kaga-Gun (JP)

(73) Assignees: Japan Science And Technology Agency, Kawaguchi-Shi (JP); Okayama Prefecture, Okayama-Shi (JP)

(*) Notice: Subject to any disclaimer, the term of this patent is extended or adjusted under 35 U.S.C. 154(b) by 0 days.

(21) Appl. No.: 14/600,984

(22) Filed: Jan. 20, 2015

(65) Prior Publication Data

US 2015/0140599 A1    May 21, 2015

Related U.S. Application Data

(62) Division of application No. 12/518,581, filed as application No. PCT/JP2007/073795 on Dec. 10, 2007, now Pat. No. 8,999,888.

(30) Foreign Application Priority Data

Dec. 11, 2006  (JP) ................................. 2006-333635

(51) Int. Cl.
| | |
|---|---|
| A01N 37/46 | (2006.01) |
| A01N 25/26 | (2006.01) |
| A01N 37/18 | (2006.01) |
| A01H 1/04 | (2006.01) |
| A01N 63/00 | (2006.01) |
| C12N 15/82 | (2006.01) |

(52) U.S. Cl.
CPC ................. *A01H 1/04* (2013.01); *A01N 37/46* (2013.01); *A01N 63/00* (2013.01); *C12N 15/8261* (2013.01)

(58) Field of Classification Search
None
See application file for complete search history.

(56) References Cited

U.S. PATENT DOCUMENTS

| | | | |
|---|---|---|---|
| 4,361,436 A | 11/1982 | McCarthy | |
| 4,436,547 A | 3/1984 | Sampson | |
| 5,211,738 A | 5/1993 | Sasaki | |
| 5,256,558 A | 10/1993 | Coruzzi | |
| 5,350,689 A | 9/1994 | Shillito | |
| 5,538,878 A | 7/1996 | Thomas | |
| 5,595,733 A | 1/1997 | Carswell | |
| 5,595,896 A | 1/1997 | Coruzzi | |
| 5,643,853 A | 7/1997 | Morre | |
| 5,766,900 A | 6/1998 | Shillito | |
| 5,770,450 A | 6/1998 | Shillito | |
| 5,824,302 A | 10/1998 | Carswell | |
| 5,869,456 A | 2/1999 | Levy | |
| 5,872,216 A | 2/1999 | Hannah | |
| 5,883,048 A * | 3/1999 | Morre ................. | A01N 31/02 504/138 |
| 5,955,651 A | 9/1999 | Coruzzi | |
| 6,030,950 A | 2/2000 | Ohlenschlager | |
| 6,031,156 A | 2/2000 | Coruzzi | |
| 6,107,547 A | 8/2000 | Coruzzi | |
| 6,166,293 A | 12/2000 | Doerner | |
| 6,442,486 B1 | 8/2002 | Satake | |
| 6,559,358 B1 | 5/2003 | Murray | |
| 6,864,405 B1 | 3/2005 | Coruzzi | |
| 7,479,267 B2 * | 1/2009 | Ogawa ................. | A01H 3/04 424/9.2 |
| 8,268,748 B2 * | 9/2012 | Ogawa ................. | A01N 37/46 504/116.1 |
| 8,575,428 B2 * | 11/2013 | Kondo ................. | A01N 37/46 800/290 |
| 8,927,286 B2 | 1/2015 | Ogawa | |
| 8,999,888 B2 | 4/2015 | Ogawa | |
| 2002/0069430 A1 | 6/2002 | Kisaka | |
| 2003/0110527 A1 | 6/2003 | Ogawa et al. | |
| 2003/0115638 A1 | 6/2003 | Izui | |
| 2003/0177520 A1 | 9/2003 | Yanagisawa | |
| 2004/0052774 A1 | 3/2004 | Creissen | |
| 2004/0133947 A1 | 7/2004 | Kisaka | |
| 2005/0114925 A1 | 5/2005 | Kisaka | |
| 2006/0123505 A1 | 6/2006 | Kikuchi | |
| 2006/0183137 A1 | 8/2006 | Harper | |
| 2007/0130643 A1 | 6/2007 | Kisaka | |
| 2008/0182752 A1 | 7/2008 | Izumori et al. | |
| 2008/0271200 A1 | 10/2008 | Dudits | |
| 2009/0099023 A1 | 4/2009 | Ogawa et al. | |
| 2010/0016166 A1 | 1/2010 | Ogawa | |
| 2010/0083404 A1 | 4/2010 | Ogawa | |

(Continued)

FOREIGN PATENT DOCUMENTS

| | | |
|---|---|---|
| CA | 2652482 | 8/2007 |
| CN | 101557709 A | 10/2009 |

(Continued)

OTHER PUBLICATIONS

Kuk et al.,Mechanism of paraquat tolerance in cucumber leaves of various stages, Weed Science, 2006, vol. 54 No. 1, pp. 6-15.*
Ma et al.,Study on regeneration system for alfalfa in Xinjiang, Xinjiang Nongye Kexue, 2005, vol. 42 No. 1, pp. 19-23.—ABS.*
L-Buthionine (S,R)-Sulfoximine Product Sheet, [online] 2011, [retrieved Nov. 30, 2011], retrieved from URL:<<http://www.chemspidercom/Chemical-Structure.106767.html>>, pp. 1-2.
Office Action dated Jul. 15, 2014, issued for U.S. Appl. No. 12/518,581.
Office Action dated Mar. 24, 2014, issued for U.S. Appl. No. 12/518,581.

(Continued)

*Primary Examiner* — Alton Pryor
(74) *Attorney, Agent, or Firm* — Locke Lord LLP

(57) ABSTRACT

A plant growth regulator containing glutathione allows increasing harvest index. This provides a technique for specifying a control factor for a plant, thereby effectively controlling germination, growth, anthesis etc. of the plant.

14 Claims, 42 Drawing Sheets

(56) References Cited

U.S. PATENT DOCUMENTS

| | | |
|---|---|---|
| 2010/0242141 A1 | 9/2010 | Ogawa |
| 2011/0078818 A1 | 3/2011 | Kondo |
| 2011/0191898 A1 | 8/2011 | Crowley |
| 2012/0324601 A1 | 12/2012 | Ogawa |
| 2014/0121100 A1 | 5/2014 | Habib |

FOREIGN PATENT DOCUMENTS

| | | |
|---|---|---|
| CN | 101583713 A | 11/2009 |
| CN | 102076856 A | 5/2011 |
| EP | 0655196 A2 | 5/1995 |
| EP | 1277404 A1 | 1/2003 |
| EP | 1992219 | 11/2008 |
| EP | 2208419 A1 | 7/2010 |
| FR | 2710234 | 3/1995 |
| JP | 59-106407 | 6/1984 |
| JP | 62-100225 | 5/1987 |
| JP | 04-500369 | 1/1992 |
| JP | 04217608 | 8/1992 |
| JP | 5-49470 | 3/1993 |
| JP | 0-199611 | 7/1994 |
| JP | 08-228621 | 9/1996 |
| JP | 9-503389 | 4/1997 |
| JP | 10-271924 | 10/1998 |
| JP | 10-323128 | 12/1998 |
| JP | 11-501034 A | 1/1999 |
| JP | 2000-038308 | 2/2000 |
| JP | 2000-300077 | 10/2000 |
| JP | 2000-515020 | 11/2000 |
| JP | 2001-505410 | 4/2001 |
| JP | 2001-288011 | 10/2001 |
| JP | 2001-519659 | 10/2001 |
| JP | 2001-346464 | 12/2001 |
| JP | 2003-125661 | 5/2003 |
| JP | 2003-310072 | 11/2003 |
| JP | 2004-264245 | 9/2004 |
| JP | 2004-267044 | 9/2004 |
| JP | 2004-352679 | 12/2004 |
| JP | 2005-052114 | 3/2005 |
| JP | 2005-110506 | 4/2005 |
| JP | 2005-130770 | 5/2005 |
| JP | 2006-141252 | 6/2006 |
| JP | 2006-188482 | 7/2006 |
| JP | 2007-131562 | 5/2007 |
| JP | 2007-530063 | 11/2007 |
| JP | 2008-070384 | 3/2008 |
| JP | 2008-120815 | 5/2008 |
| JP | 2009-165494 | 7/2009 |
| JP | 2010-166851 | 8/2010 |
| JP | 4621891 | 11/2010 |
| RU | 2126047 C1 | 2/1999 |
| RU | 2415573 | 4/2011 |
| WO | 91/00008 | 1/1991 |
| WO | 00/05969 | 2/2000 |
| WO | 00/36911 | 6/2000 |
| WO | WO-01/080638 | 11/2001 |
| WO | 02/10210 | 2/2002 |
| WO | 02/33105 | 4/2002 |
| WO | 03/000041 | 1/2003 |
| WO | 2004/016726 | 2/2004 |
| WO | WO-2006023782 A2 | 3/2006 |
| WO | WO-2007/091634 | 8/2007 |
| WO | 2008/072602 | 6/2008 |
| WO | 2008/082602 | 7/2008 |
| WO | 2009/063806 | 5/2009 |

OTHER PUBLICATIONS

Office Action dated Dec. 6, 2011, issued for U.S. Appl. No. 12/518,581.
Office Action dated Jun. 9, 2011, issued for U.S. Appl. No. 12/518,581.
Nature, vol. 187, pp. 81-82 (1960).
Plant & Cell Physiology, vol. 45, No. 2, pp. 129-137 (2004).
Biochemical and Biophysical Research Communications, vol. 133, No. 3, pp. 988-993 (1985).
Biochemical Organic Compounds for Research and Diagnostic Reagents, 1989. Sigma Chemical Company. p. 657, product No. G4251.
Australian Office Action mailed May 4, 2010. (Application No. 2007330795).
Decision to Grant issued in corresponding Russian Application No. 2009123026 mailed Sep. 15, 2009.
Ogawa, K. et al. "Level of Glutathione is Regulated by ATP-Dependent Ligation of Glutamate and Cysteine through Photosynthesis in *Arabidopsis thaliana*:Mechanism of Strong Interacion of Light Intensity with Flowering", Plant and Cell Physiology, vol. 45, No. 1, pp. 1-8.
Henmi K. et al., "A Possible Role of Glutathione and Glutathione Disulfide in Tracheary Element Differentiation in the Cultured Mesophyll Cells of *Zinnia Elegans*" Plant Cell Physiol., vol. 42, No. 6, pp. 673-676(2001).
Razem F. et al., "The RNA-binding protein FCA is an abscisic Acid Receptor" Nature, vol. 439, No. 7074, pp. 290-294 (2006).
Fei-Yi, T. et al., "A Comparative Study of the Effects of Abscisic Acid and Methyl Jasmonate on Seedling Growth of Rice" Plant Growth Regulation, vol. 21, No. 1, pp. 37-42 (1997).
Supplementary European Search Report fot Corresponding European Application No. EP-07850363, Issued Dec. 1, 2011.
Examiner's Report for Australian Application No. 2008321944 dated Sep. 13, 2010.
Office Action issued in Australian Patent Application No. 2009224235 on Dec. 16, 2011.
Canadian Office Action mailed on Apr. 4, 2013, during prosecution of CanadianPatent Application No. 2,687,249.
1st Office Action for CN 201280061106.1 issued of Feb. 25, 2015, with full English Translation.
1st Office Action for CN 201280052993.6 issued on Dec. 8, 2014, with full English translation.
2nd Office Action for CN 201280052993.6 issued on Aug. 13, 2015, with full English translation.
Decision on Reexamination for CN 200780045685.X issued on Sep. 23, 2015,with full English translation.
Supplementary European Search Report for European Application No. 08849628.6, mailed Dec. 22, 2011.
European Examination Report issued Apr. 6, 2011 in European Application No. 01 922 034.2.
European Examination Report issued Feb. 13, 2006 in corresponding European Application No. 01 922 034.2.
European Examination Report issued Jul. 27, 2007 in corresponding European Application No. 01 922 034.2.
European Examination Report issued Jun. 1, 2012 in European Application No. 09 009 268.5.
European Examination Report issued Jun. 30, 2010 in European Application No. 01 922 034.2.
European Examination Report issued May 21, 2012 in European Application No. 10 180 526.5.
European Examination Report issued May 23, 2012 in European Application No. 10 180 963.0.
European Examination Report issued Nov. 4, 2008 in European Application No. 01 922 034.2.
European Examination Report issued Nov. 8, 2010 in European Application No. 01 922 034.2.
European Patent Office Search Report issued Nov. 17, 2010 in European Patent Application No. 10180963.
Examination Report issued Jul. 20, 2011 in European Application No. 10 002 403.1.
Examination Report issued May 8, 2012 in European Application No. 10 002 403.3.
Extended European Search Report issued Nov. 18, 2010 in European Application No. 10180526.5.
Extended European Search Report issued Oct. 19, 2010 in European Patent Application EP 10 00 2403.
Extended European Search Report issued Oct. 19, 2010 in European Patent Application No. EP 09 00 9268.
Office Action issued in the European Patent Application No. 01922034 dated Sep. 22, 2009.

(56) References Cited

OTHER PUBLICATIONS

Partial European Search Report issued Dec. 21, 2004 in European Application No. 01 922 034.2.
Partial European Search Report issued Jul. 19, 2010 in European Application No. 10002403.3.
Partial European Search Report issued Jul. 20, 2010 in European Application No. 09009268.5.
Supplementary European Search Report issued May 2, 2005 in European Application No. 01 922 034.2.
Notice of Reasons for Refusal (with English translation) issued Oct. 2, 2007 in JP Application No. 2001-577748.
Notice of Reasons for Refusal (with partial English translation) issued Feb. 15, 2011 in JP Application No. 2007-312518.
English translation of office action mailed Jul. 2, 2013, JP patent application No. 2011-545244.
Japanese Office Action mailed on May 7, 2013, in JP Application No. 2009-541115 with full English Translation.
Office Action for JP patent application No. 2013-549197,issued on Oct. 27, 2015 with full English Translation.
Notice of Allowance dated Oct. 4, 2011, for Russian Patent Application No. 2009139630, and English Translation.
2nd Office Action for TW 101146054 issued on Aug. 28, 2015, with English translation.
Office Action dated Aug. 17, 2011, in connection with U.S. Appl. No. 12/599,710.
Office Action dated Feb. 24, 2012, in connection with U.S. Appl. No. 12/599,710.
Office Action dated Nov. 22, 2011, in connection with U.S. Appl. No. 12/599,710.
1st Office Action for U.S. Appl. No. 12/314,433 issued on Dec. 19, 2013.
1st Office Action for U.S. Appl. No. 10/258,234 issued on Dec. 31, 2003.
1st Office Action for U.S. Appl. No. 12/879,581 issued on Oct. 17, 2012.
1st Office Action for U.S. Appl. No. 13/514,402 issued on Nov. 1, 2013.
1st Office Action for U.S. Appl. No. 13/586,612 issued on Sep. 24, 2012.
1st Office Action for U.S. Appl. No. 12/314,433 issued on Aug. 3, 2010.
1st Office Action for U.S. Appl. No. 14/364,477 issued on Dec. 16, 2015.
2nd Office Action for U.S. Appl. No. 10/258,234 issued on Aug. 25, 2004.
2nd Office Action for U.S. Appl. No. 13/514,402 issued on Mar. 31, 2014.
2nd Office Action for U.S. Appl. No. 12/314,433 issued on Feb. 26, 2015.
3rd Office Action for U.S. Appl. No. 10/258,234 issued on May 12, 2005.
5th Office Action for U.S. Appl. No. 10/258,234 issued on Oct. 11, 2007.
5th Office Action for U.S. Appl. No. 10/258,234 issued on Nov. 1, 2006.
4th Office Action for U.S. Appl. No. 10/258,234 issued on Feb. 9, 2006.
Advisory Action for U.S. Appl. No. 10/258,234 issued on Aug. 8, 2007.
Advisory Action for U.S. Appl. No. 12/314,433 issued on May 20, 2011.
Advisory Action for U.S. Appl. No. 13/514,402 issued on Sep. 4, 2014.
Corrected Notice of Allowance for U.S. Appl. No. 13/514,402 issued on Oct. 7, 2014.
Election/Restriction Requirement for U.S. Appl. No. 14/364,477 issued on Oct. 2, 2015.
Final Office Action for U.S. Appl. No. 10/258,234 issued on Apr. 25, 2008.
Final Office Action for U.S. Appl. No. 10/258,234 issued on Jun. 21, 2007.
Final Office Action for U.S. Appl. No. 13/514,402 issued on Jul. 24, 2014.
Final Office Action for U.S. Appl. No. 13/586,612 issued on Apr. 4, 2013.
Final Office Action for U.S. Appl. No. 12/314,433 issued on Dec. 8, 2015.
Final Office Action for U.S. Appl. No. 12/314,433 issued on Dec. 14, 2010.
Final Office Action for U.S. Appl. No. 12/314,433 issued on Oct. 17, 2014.
Notice of Allowance for U.S. Appl. No. 10/258,234 issued on Oct. 1, 2008.
Notice of Allowance for U.S. Appl. No. 12/879,581 issued on Jul. 8, 2013.
Notice of Allowance for U.S. Appl. No. 13/514,402 issued on Sep. 23, 2014.
Notice of Allowance for U.S. Appl. No. 13/586,612 issued on Jun. 3, 2013.
Office Action for U.S. Appl. No. 14/473,001 issued on Mar. 24, 2016.
Restrictions Requirement for U.S. Appl. No. 10/258,234 issued on Sep. 2, 2003.
International Preliminary Examination Report (English translation) issued Mar. 25, 2002 in International Application No. PCT/JP01/03491.
International Search Report (English translation) issued Jul. 17, 2001 in International (PCT) Application No. PCT/JP01/03491.
English translation of International Search Report mailed Mar. 15, 2011, International Patent Application No. PCT/JP2010/072137.
International preliminary report on patentability (Chapter I ) of PCT/JP2012/078073 issued on Feb. 5, 2013.
International preliminary report on patentability PCT/JP2012/080771 dated Jun. 12, 2014.
International Search Report of PCT/JP2012/078073 dated Feb. 5, 2013.
International Search Report of PCT/JP2012/080771 dated Mar. 5, 2013.
"Formation of Callus and Redifferentiation of Shoots from *Arabidopsis thaliana* Petal and Sepal Explants", Memoirs of Osaka Kyoiku University. Ser. 3. Natural Science and Applied Science, vol. 49, No. 2, 2001, pp. 277-283, Abstract, <hap ://sciencelinks.jp/j-east/article/200115/000020011501A0457740.php>.
O. Fontaine et al., "Effect of glutathione on dormancy breakage in barley seeds," Plant Growth Regulation, vol. 16, pp. 55-58,1995.
C.J. Kim et al., "*Arabidopsis* ORF Clones", Accession No. AAM10415, dated Apr. 13, 2002 (Unpublished),ncbi.nlm.nih.gov/sviewer/viewerfcgi?tool=portal&sendto=on&log$-seqv . . . (dated Jan. 20, 2012).
Elhiti, Mohamed, et al., "Modulation of embryo-forming capacity in culture through the expression of *Brassica* genes involved in the regulation of the shoot apical meristem", Journal of Experimental Botany, vol. 61, No. 14, 2010, pp. 1069-4085.
Gupta, Ashima S., et al., "Response of Photosynthesis and Cellular Antioxidants to Ozone in Populus Leaves", Plant physiol.,vol. 96, 1991, pp. 650-655.
Habaguchi, Kazuo, "Alterations in polyphenol oxidase activity during organ redifferentiation in carrot calluses cultured invitro", Plant Cell Physiol., vol. 18, Issue 1, 1977, pp. 181-189, Abstract,< http ://pcp.oxfordj ournals.org/content/18/1/181.abstract>.
Hopkins, et al., "On Glutathione. A Thermostable Oxidation-reduction Systems", J. Biol. Chem.(1992) 54, p. 527-563.
Ito, H. et al., "The Sugar-Metabolic Enzymes Aldolase and Those-Phosphate Isomerase areTargets of Glutathionylation in *Arabidopsis thaliana*; Detection using Biotinylated Glutathione",Plant Cell Physiol. (2003) 44(7); p. 355-660 (2003).
K. Ogawa et al., "Involvement of Glutathione in Flowering in *Arabidopsis Thaliana*," Plant Cell Physiol. (2001), vol. 42, No. Supplemental, p. S78.
"Kazoe", Farm Chemicals Handbook, 1995 edition, C214.

(56) References Cited

OTHER PUBLICATIONS

Koprivova, Anna, et al., "Regulation of Sulfate Assimilation by Nitrogen in *Arabidopsis*", Plant Physiology, vol. 122, Mar. 2000, pp. 737-746.
L. Liu et al., "Localization of hydrogen peroxide production in Zinnia elegans L. Stems", Phytochemistry, vol. 52, No. 4, pp. 545-554, 1999.
Lappartient, Anne G., et al., "Glutathione-Mediated Regulation of ATP Sulfurylase Activity, SO42—Uptake, and Oxidative Stress Response in Intact Canola Roots", Plant Physiol., vol. 114, 1997, pp. 177-183.
M. Yanagida et al., "The Vernalization-Induced Bolting Involeves Glutathione Redox Regulation in Eustoma Grandiflorum," Plant and Cell Physiol. (2001), vol. 42, No. Supplement, p. S78.
Nieto-Sotelo, Jorge, et al., "Effect of Heat Shock on the Metabolism of Glutathione in Maize Roots", Plant Physiol., vol. 32, 1986, pp. 1031-1035.
Nishi, Toyoyuki, et al., "Organ Redifferentiation and Plant Restoration in Rice Callus", Nature, vol. 219, Aug. 1968, pp. 508-509, Abstract, <http://www.nature.com/nature/journal/v219/n5153/abs/219508a0.html>.
Ogawa, K. et al., "Fructose-1,6-Bisphosphate Aldolase is a Target Protein of Glutathionylationin Arabidopsis Chloroplasts", XP003016751, 13th International Congress on Photosynthesis,HTTP://abstracts.co.allenpress.com/oweb/pwc2004/document/?ID+39705 (2007).
Ogura, Hisakazu, "The effects of a morphactin, chlorflurenol, on organ redifferentiation from tobacco calluses cultured invitro", Journal of Plant Research, vol. 88, No. 1, 1975, pp. 1-8, Abstract<http://www.springerlink.com/content/735413224084k5x6/>.
Patterson, John W., et al., ""Reactions of Alloxan and Dialuric Acid with the Sulfhydryl Group"", J. Biol. Chem., vol. 177, 1949, pp. 197-204.
Peter J. Lea, "Primary Nitrogen Metabolism", Chapter 7 in Plant Biochemistry, Dey and Harbome., eds., 305-306, 1997.
Phillips, G. C. and G. B. Collins, "Induction and Development of Somatic Embryos from Cell Suspension Cultures of SoybeanGlycine—Max," Plant Tissue and Organ Culture (1981), Obtained from Database Biosis [Online].
Phillips, Gregory and G.B. Collins, "Induction and development of somatic embryos from cell suspension cultures of soybean," Plant Cell Tissue Organ Culture, vol. 1, No. 2, pp. 123-130, 1981.
R. Macknight, et al., "FCA, a Gene Controlling Lowering Time in *Arabidopsis*, Encodes a Protein Containing RNA-Binding Domains", Cell, vol. 89, pp. 737-745, 1997.
Rauser, Wilfried E., et al., "Cysteine, γ-Glutamylcysteine, and Glutathione Levels in Maize Seedlings", Plant Physiol., vol. 97, 1991, pp. 128-138.
Reese et al., "Effects of Buthionine Sulfoximine on Cd-Binding Peptide Levels in Suspension-Cultured Tobacco Cells Treated with Cd, Zn, or Cu", Plant Physiology, 84: 574-577, 1987.
Shi, Zheng-Zheng, et al., "Glutathione synthesis is essential for mouse development but not for growth in culture", PNAS. vol. 97, No. 10, May 9, 2000, pp. 5101-5106.
Shimada, T., et al., "In Vitro Culture of Wheat Tissues. I. Callus Formation, Organ Redifferentiation and Single Cell culture", Canadian Journal of Genetics and Cytology, vol. 11, No. 2, 1969, pp. 294-304, Abstract,< h t t p ://www.nrcresearchpress.com/doi/abs/10.1139/g69-037?journalCode=cgc>.
Simoni et al., "The Discovery of Glutathione by F. Gowland Hopkins and the Beginning of Biochemistry at Cambridge University", J. Biol. Chem, vol. 277, No. 24, 2002.
Smith, Ivan K., "Stimulation of Glutathione Synthesis in Photorespiring Plants by Catalase Inhibitors", Plant Physiol., vol. 79,1985, pp. 1044-1047.
Streb, P., et al., "Significance of antioxidants and electron sinks for the cold-hardening-induced resistance of winter rye leaves to photooxidative stress", Plant, Cell and Environment, vol. 22, 1999, pp. 1225-1237.

Tanemura, Yasuko, "Polyamine Enhances the Regeneration of Reduced Glutathione by the Activation of NADP-dependentDehydrogenases in yeast", Biomedical Research, vol. 25, No. 2, pp. 69-74 (2004).
U. Sethi et al., "Control of Cell Proliferation and Differentiation by Regulating Polyamine Biosynthesis in Cultures of *Brassica* and its Correlation with Glyoxalase-I Activity," Plant Science, vol. 56, No. 2, pp. 167-176, 1988.
Wingsle, et al. ,"Differential redox regulation by glutathione of glutathione reductase and CuZn-superoxide Dismutase Gene Expression in *Pinus Sylvestris* L. needles," Planta (1996) 198: p. 151-157.
Yamada, Yasuyuki, et al., "Nucleic Acid in Callus Formation and in Redifferentiation of Callus in *Nicotiana Tabacum*", Soil Science and Plant Nutrition, vol. 14, No. 1, 1968, pp. 35-38.
Yoshida, Kaoru T., et al., "Control of Organogenesis and Embryogenesis in Rice Calli", Breeding Science, vol. 44, 1994, pp. 355-360.
A. Groover et al., "Programmed cell death of plant tracheary elements differentiating in vitro", Protoplasma, vol. 196, No. 3-4, pp. 197-211, 1997.
"Informal discussion about amino acids of plants", Life World, 1990, No. 2 with English translation.
"Absorption and Utilization of amino acids by plant", Journal of Southwest University of Science and Technology, vol. 19, No. 1, Mar. 2004 with English translation.
"Absorption and Utilization of amino acids by plant and application of amino acids on agriclture", Soil and Fertilizer Science in China, 2008, No. 1 with English translation.
Alvarez et al. (Cell, (1998) 92: pp. 773-784).
Angela Saez et al., "Gain-of-function and loss-of-function phenotypes of the protein phosphatase 2C HAB1 reveal its role as a negative regulator of abscisic acid signalling", The Plant Journal, 2004, 37: 354-369.
Annals of Botany, vol. 43: 305-318 (1979).
Asada, T., "Tree Propagation Technology and Research Topics on Afforestation at Corporate Level," Forestry Research Institute, Oji Paper Company Limited (Research note, Regulation of Plant Growth & Development vol. 41, No. 1, pp. 83-89 (2006), The Japanese Society for Chemical Regulation of Plants, with partial translation.
Auderset et al. Stimulation of Root Formation by Thiol Compounds (Hort h Science 31(2):240-242. (1996).
B. Earnshaw, et al., "Control of Wild Carrot Somatic Embryo Development by Antioxidants'—A Probable Mode of action of 2,4-Dichlorophenoxyacetic Acid", Plant Physiol., vol. 85, pp. 273-276, 1987.
B. Earnshaw, et al.,"The Effect of Glutathione on Development in Wild Carrot Suspension Cultures", Biochemical and Biophysical Research Communications, vol. 133, No. 3, pp. 988-993, 1985.
Belmonte, M.F., et al., "Alterations of the glutathione redox state improve apical meristem structure and somatic embryo quality in white spruce (*Picea glauca*)," Journal of Experimental Botany, vol. 56, No. 419, pp. 2355-2365, Sep. 2005, Advance Access Publication Jul. 4, 2005.
Belmonte, M.F., et al., "Glutathione-induced growth of embryogenic tissue of white spruce correlates with change sin pyrimidine nucleotide metabolism," Plant Science (2005), vol. 168, pub. 12, Nov. 12, 2004, pp. 803-812.
Bull. Hyogo Pre. Agri. Inst. (Agriculture) 50, 41-46 (2002) with partial English translation.
C. Chien et al., "Mechanism of hydrogen peroxide in improving the germination of *Cinnamomum camphora* seed", Seed Science and Technology, vol. 22, No. 2, pp. 231-236, 1994.
Caliskan et al., The Plant Journal, (1998),15(2), pp. 165-171).
Crop Science, vol. 43: 2206-2211 (2003).
David Reyes et al., "Overexpression of a Protein Phosphatase 2C from Beech Seeds in *Arabidopsis* Shows Phenotypes Related to Abscisic Acid Responses and Gibberellin Biosynthesis", Plant Physiology, 2006, 141: 1414-1424.

(56) References Cited

OTHER PUBLICATIONS

E Koesema et al., "*Arabidopsis* cDNA Clones", Accession No. AAK91405, dated Aug. 20, 2001 (Unpublished), http://www.ncbi.nlm.nih.gov/sviewer/viewerfcgi?tool=portal&sendto=on&log$-seqv . . . (dated Jan. 20, 2012).
E Tarenghi, et al., "Polyamines, floral induction and floral developments of strawberry (*Fragaria ananassa* Duch.)", Plant Growth Regulation, vol. 17, pp. 157-165, 1995.
Finch-Savage (New Phytologist, (2006), 171:pp. 501-523).
Gossett et al. (Plant Phsiol. (1996), 112: pp. 803-809).
H. Fukuda, "Tracheary element differentiation", Plant Cell, vol. 9, No. 7, pp. 1147-1156, 1997.
Henmi et al. (Plant Cell Physiol. (2005), 46(11), pp. 1757-1765).
Herschnach et al (Plant Cell Physiol. 1998 39(4): 447-451).
Howden, Ross, et al., "Cadmium-Sensitive Mutants of *Arabidopsis thaliana*", Plant Physiol., vol. 99, 1992, pp. 100-107.
Imin, N., et al., "Factors involved in root formation in Medicago truncatula," Journal of Experimental Botany (2007), vol. 58(3), Advance Access pub. Dec. 6, 2006, pp. 439-451.
J. Kurepa, et al., "Oxidative stress tolerance and longevity in *Arabidopsis*: The late-flowering mutant gigantea is tolerant to paraquat", Plant Journal, vol. 14, No. 6, pp. 759-764, 1998.
K. Ogawa, et al "A mechanism for promoting the germination of *Zinnia elegans* seeds by hydrogen peroxide", Plant and Cell Physiology, vol. 42, No. 3, pp. 286-291, 2001.
K.C. Kim, et al.,"Photoperiodic Floral Induction in Pharbitis Cotyledons Affected by Polyamines and Ethylene", J.Plant Biol., vol. 38, No. 3, pp. 227-234,1995.
K.P. Reddy, et al., "Catalase activity in rice shoot apex during panicle initiation", Plant and Cell Physiology, vol. 26, No. 7, pp. 1419-1424, 1985.
Le Roux et al. Micropropagation and tissue culture of Eucalyptus (Tree Physiology 9, 435-477, 1991).
M.E.B. Naredo et al., "Responses to seed dormancy-breaking treatments in rices species", Seed Science and Technology, vol. 26, No. 3, pp. 675-689, 1998.
Noctor G. et al., "Manipulation of Glutathione and Amino Acid Biosynthesis in the Chloroplast", Plant Physiol. (1998) 118: 471-482.
Mapson, L.W., "The Estimation of Oxidized Glutathione" Biochem Journal, vol. 55, No. 4, 1953, pp. 714-717.
Mary Paz Gonzalez-Garcia et al., "Negative Regulation of Abscisic Acid Signaling by the Fagus sylvatica FsPP2C1 Plays a Role in Seed Dormancy Regulation and Promotion of Seed Germination", Plant Physiology, 2003, 133: 135-144.
McGraw-Hill Dictionary of Scientific and Technical Terms, Second Edition, McGraw-Hill, Inc., 1978, pp. 1337.
Meinhard and Grill, FEBS Letters (2001) 508:443-446.
N. Wada, et al., "Flower Induction by Polyamines and Related Compounds in Seedlings of Morning Glory (*Pharbitis nilcy*cv. Kidachi)", Plant Cell Physiol., vol. 35, No. 3, pp. 469-472, 1994.
Norby et al., "Effects of Atmospheric Co2 Enrichment on the Growth and Mineral Nutrition of *Qurecus alba* Seedings in Nutrient-Poor Soil," (Plant Physiol. (1986) 82, 83-89).
O. Fontaine et al., "Dormancy breakage of Hordeum vulgare seeds: Effects of hydrogen peroxide and scarification on glutathione level and glutathione reductase activity", Plant Phyiology and Biochemistry, vol. 32, No. 5, pp. 677-683, 1994.
O. Tanaka, et al.,"Effect of Ferricyanide, Ferrocyanide and KCN on Growth and Flowering in the Short-Day Plant *Lemna paucicostata* 6746", Plant and Cell Physiol. vol. 24, No. 4, pp. 705-711, 1983.
P. B. Applewhite, et al., "A role for spermidine in the bolting and flowering of *Arabidopsis*", Physiologia Plantarum, vol. 108, pp. 314-320, 2000.
Penfield et al. (Current Biology, pp. 2366-2370, (2006)).
Plant Cell Physiology 43(10) • 1096-1105 (2002).
Plant Cell Physiology 46(8); 1175-1189 (2005).
Plant Physiology, vol. 84:1126-1131 (1987).

R. Sanchez-Fernandez, et al., "Cell proliferation and hair tip growth in the *Arabidopsis* root are under mechanistically lifferent forms of redox control", Proc. Natl. Acad. Sci., vol. 94, pp. 2745-2750, 1997.
S. Gallais et al., "Pyridine nucleotides and redox charges during germination of non-dormant and dormant caryopses of *Avena sativa* L", Journal of Plant Physiology, vol. 153, No. 5-6, pp. 664-669, 1998.
S. Sato et al., "Structural Analysis of *Arabidopsis Thaliana* Chromosomes 3. I. Sequence Features of the "Regions of 4,504,864 by Covered by Sixty P1 and TAC Clones"" Accession No. BAA95773, dated Feb. 14, 2004, DNA Res, 7 (2):131-135, ncbi.nlm.nih.gov/sviewer/viewerfcgi?tool=portal&sendto=on&log$-seqv . . . (dated Jan. 20, 2012).
Schweighofer et al,Trends in Plant Sci. (2004) 9:236-243.
Science 286:1960-1962 (1999).
Sotelo, M., et al., "Micropropagation of *Eucalyptus maidenii* elite trees," Agrociencia (2007) vol. XI No. 1, pp. 81-89.
T. Potikha, et al., "The Involvement of Hydrogen Peroxide in the Differentiation of Secondary Walls in Cotton Fibers", Plant Physiology, vol. 119, pp. 849-858, 1999.
Tri--Panji Et. Al., Fatty acid composition of juvenile palm leaf and its possible application for prediction of yield potential, Proceedings of BTIG Workshop on Oil Palm Improvement through Biotechnology, p. 122-126, Dec. 1998.
Tyburski et al., "Glutathione and glutathione disulfide effect adventitious root formation and growth in tomato seedling cuttings." Acta Physiol. Plant (2010) 32: 411-417. Published online :Nov. 24, 2009.
Umbarasaite et al., Methods in Mol. Bio. (2011) 779:149-161.
Velikova et al. (Plant Science, (2000) 151; pp. 59-66).
Willekens et al., (EMBO journal; vol. 16, No. 16, pp. 4806-4816, (1997)).
X. Lin et al., "*Arabidopsis thaliana* chromosome III BAC F18C1 Genomic Sequence", Accession No. AAF26133, dated Oct. 30, 2002 (Unpublished), ncbi.nlm.nih.gov/sviewer/viewerfcgi?tool=portal&sendto=on&log$-seqv . . . (dated Jan. 20, 2012).
Y. Totoki et al., "Large-Scale Analysis of RI KEN *Arabidopsis* Full-length (RAFL) cDNAs", Accession No. BAF00337, dated Jul. 27, 2006 (Unpublished), ncbi.nlm.nih.gov/sviewer/viewerfcgi?tool=portal&sendto=on&log$-seqv . . . (dated Jan. 20, 2012).
Z. Naturforsch, "Effects of Polyamines on Glutathione Reductase Activity in Spinach", vol. 63(c), 2008, pp. 260-266.
Z. Ye, et al., "The developmental transition to flowering represses ascorbate peroxidase activity and induces enzymatic lipid peroxidation in leaf tissue in *Arabidopsis thaliana*", Plant Biology, vol. 1999, p. 75, 1999.
Z. Ye, et al., "The developmental transition to flowering represses ascorbate peroxidase activity and induces enzymatic lipid peroxidation in leaf tissue in *Arabidopsis thaliana*", Plant Science, vol. 158, No. 1-2, pp. 115-127, 2000.
Jiao et al.,"Monitoring crop yield using NOAA/AVHRR-based vegetation indices," Transactions of the CSAE, vol. 21(4), pp. 104-108,2005., with English translation.
Digital Farming Technology CAO Wei-xing et al., p. 357, Science Press, Aug. 2008, first edition with English translation.
Yang et al.,"Relationships of Canopy Reflectance Spectra with Wheat Yield and Yield Components," Chinese Journal of Agrometeorogy, vo;29(3),pp. 338-342,2008 with English transaltion.
"Application of Near Infrared Spectroscopy in Detection of quality of Rice", Chinese Agrliculture Press,p. 65, 2008 with English translation.
Journal of Home Economics of Japan (Nippon Kaseigaku Kaishi), vol. 53, No. 2, pp. 199-203 (2002) with partila English translation.
Office Action Dated May 31, 2016 for U.S. Appl. No. 14/364,477.
Pamin K. et al., Genetic variation and selection response for oil composition in corn; Crop Science, vol. 26, pp. 279-282, (1986).
Brossman G.D. et al., Induction of genetic variation for oil properties and argnonomic characteristics of soybean, Crop Science, vol. 24, pp. 783-787, (1984).

(56) References Cited

OTHER PUBLICATIONS

Allowance for RU Patent Application No. 2014118883/13(029800), dated May 30, 2016, (Corresponding to co-pending U.S. Appl. No. 14/355,768.).
Belmonte, et al. The effects of reduced and oxidized glutathione on white spruce somatic embryogenesis. In Vitro Cell Dev. Biol. Plant, 40:61-66, 2004.
Not-final Office Action dated Sep. 6, 2016 for U.S. Appl. No. 14/473,001, filed Aug. 29, 2014.
Abbasi, et al., Relationship Between Seed Colour and Linolenic Acid with Seed Yield and Yield Components of Flax (Linum usitatissimum L.) in Isfahan, Journal of Water and Soil Science, 7(1):141-153, 2003, Abstract.
Election/Restriction Requirement dated Sep. 26, 2016 for U.S. Appl. No. 14/355,768, filed May 1, 2014.
Gautheret, The Nutrition of Plant Tissue Cultures, Annu. Rev. Plant. Physiol, 6:433-484, 1955.
Non-final Office Action dated Sep. 9, 2016 for U.S. Appl. No. 12/314,433, filed Dec. 10, 2008.

\* cited by examiner (a)

(b)

(c)

Control

PLANT GROWTH REGULATOR AND USE THEREOF

CROSS-REFERENCE TO RELATED APPLICATIONS

This Application is a Division of U.S. application Ser. No. 12/518,581 filed on Jun. 10, 2009, which is the national stage application pursuant to 35 U.S.C. §371 of International Application No. PCT/JP2007/073795, filed Dec. 10, 2007 which claims priority to Japanese Application 2006-333635 filed on Dec. 11, 2006. The contents of all prior applications are incorporated herein by reference in their entirely.

TECHNICAL FIELD

The present invention relates to a plant growth regulator for regulating growth of a plant and a technique for use thereof. To be specific, the present invention relates to a plant growth regulator capable of increasing harvest index by use of glutathione, and a technique for use of the plant growth regulator.

BACKGROUND ART

Conventionally, plants have been deeply involved with human as foods, ornaments, industrial materials such as paper and chemicals, and fuels. Further, recently, plants have been spotlighted as biomass energy that will substitute fossil fuel.

Although plants have been used in such various fields, their mechanisms such as budding, growth, and anthesis have not yet been clarified in many regards. Consequently, cultivation of plants has been mainly based on experiences and intuition, and harvest of the plants has been greatly influenced by natural conditions such as weather. Therefore, clarification of plants' mechanisms such as budding, growth, and anthesis and regulating and controlling the mechanisms are very important not only for increasing yields of ornamental plants and food plants such as grains and vegetables, but also for growing woods in forests and biomass energy.

In order to regulate growth of plants, there have been made attempts such as regulation of anthesis by artificial environments such as a conservatory, and promotion of growth by use of chemicals such as ethylene. However, most of these conventional attempts are regulations of growth of plants based on experiences and intuition, and are not based on data that allows scientific evaluation of growth of plants.

In view of the above, the inventors of the present invention have researched on the plants' mechanisms of budding, growth, and anthesis. Consequently, the inventors have shown that reactive oxygen species (ROS) is essential not only as a substrate for biosynthesis but also as a factor for controlling growth of plants (see Patent Literature 1). Specifically, Patent Literature 1 describes a regulator that contains a redox state regulation substance for cells and that regulates differentiation of cells or organs, a method for controlling differentiation and morphogenesis of a organism, and a organism thus obtained.

Further, Patent Literature 2 discloses an adjuvant for regulating growth of plants and a method for preparing redifferentiated plants by used of the adjuvant. Specifically, a callus induced from a part of a plant such as rice and eustoma is cultivated in a redifferentiating culture medium containing glutathione, preferably oxidized glutathione (which may be hereinafter referred to as GSSG) so as to promote rhizogenesis, effectively obtaining a redifferentiated body from the callus in a short time.

CITATION LIST

Patent Literature 1
International Application Publication No. WO01/080638 (Publication Date: Jul. 22, 2003)
Patent Literature 2
Japanese Patent Application Publication, Tokukai, No. 2004-352679 A (Publication Date: Dec. 16, 2004)

SUMMARY OF INVENTION

Patent Literature 1 discloses a technique for controlling differentiation and morphogenesis of plants by use of a substance that regulates a redox state of the plants. However, the control mechanism is not yet sufficiently clarified and it is not known what substance serves as a factor for controlling growth of the plants. Further, although Patent Literature 2 discloses a technique for preparing a redifferentiated plant body, the technique is not sufficient. A new technique for controlling the amount of biomass, the yield of seeds, the quality of next-generation seeds etc. is required.

Scientifically understanding the process of growth of plants, scientifically predicting anthesis, and regulating them are very important not only to ornamental flowers and plants for foods, but also to forests and plant resources for biomass energy. Therefore, there has been a strong request for developing a technique for specifying a control factor for plants and effectively controlling budding, growth, anthesis etc. of plants.

The present invention was made in view of the foregoing problems. An object of the present invention is to provide a technique for specifying a control factor for plants and effectively controlling budding, growth, anthesis etc. of plants.

In order to solve the foregoing problems, the inventors of the present invention have diligently studied and found that cultivation of a plant by use of glutathione allows greatly increasing the number of seeds and the number of flowers of the plant. Further, the inventors have found that when a plant having mutation in its function for synthesizing a plant hormone (e.g. gibberellin) or responding to a plant hormone is cultivated by use of glutathione, it is possible to greatly increase the number of lateral shoots (axillary buds), and accordingly to increase the number of flowers (sheaths). The inventors have completed the present invention based on these findings. The present invention has been completed based on these new findings and includes the following subject matters.

(1) A plant growth regulator for increasing harvest index, comprising glutathione.

(2) The plant growth regulator as set forth in (1), wherein the glutathione is oxidized glutathione.

(3) The plant growth regulator as set forth in (1) or (2), for increasing the number of seeds and/or flowers of a plant.

(4) The plant growth regulator as set forth in (1) or (2), for increasing the number of lateral shoots and/or tillers of a plant.

(5) A method for cultivating a plant, comprising the step of cultivating a plant by use of glutathione so as to increase harvest index of the plant.

(6) The method as set forth in (5), wherein the glutathione is oxidized glutathione.

(7) The method as set forth in (5) or (6), wherein the glutathione is supplied intermittently.

(8) The method as set forth in any one of (5)-(7), wherein the glutathione is supplied at around a time of transition from vegetative to reproductive development.

(9) A method for increasing the number of seeds and/or flowers of a plant by use of glutathione.

(10) The method as set forth in (9), wherein the glutathione is oxidized glutathione.

(11) A method for increasing the number of lateral shoots and/or tillers of a plant by use of glutathione.

(12) The method as set forth in (11), wherein the glutathione is oxidized glutathione.

(13) The method as set forth in (11) or (12), wherein the plant has mutation in a function for synthesizing a plant hormone and/or a function for responding to a plant hormone.

(14) The method as set forth in (13), wherein the plant hormone is gibberellin.

(15) A plant obtained by a method as set forth in any one of (5)-(14), having increased harvest index.

For a fuller understanding of the nature and advantages of the invention, reference should be made to the ensuing detailed description taken in conjunction with the accompanying drawings.

DESCRIPTION OF EMBODIMENTS

Figure 1:
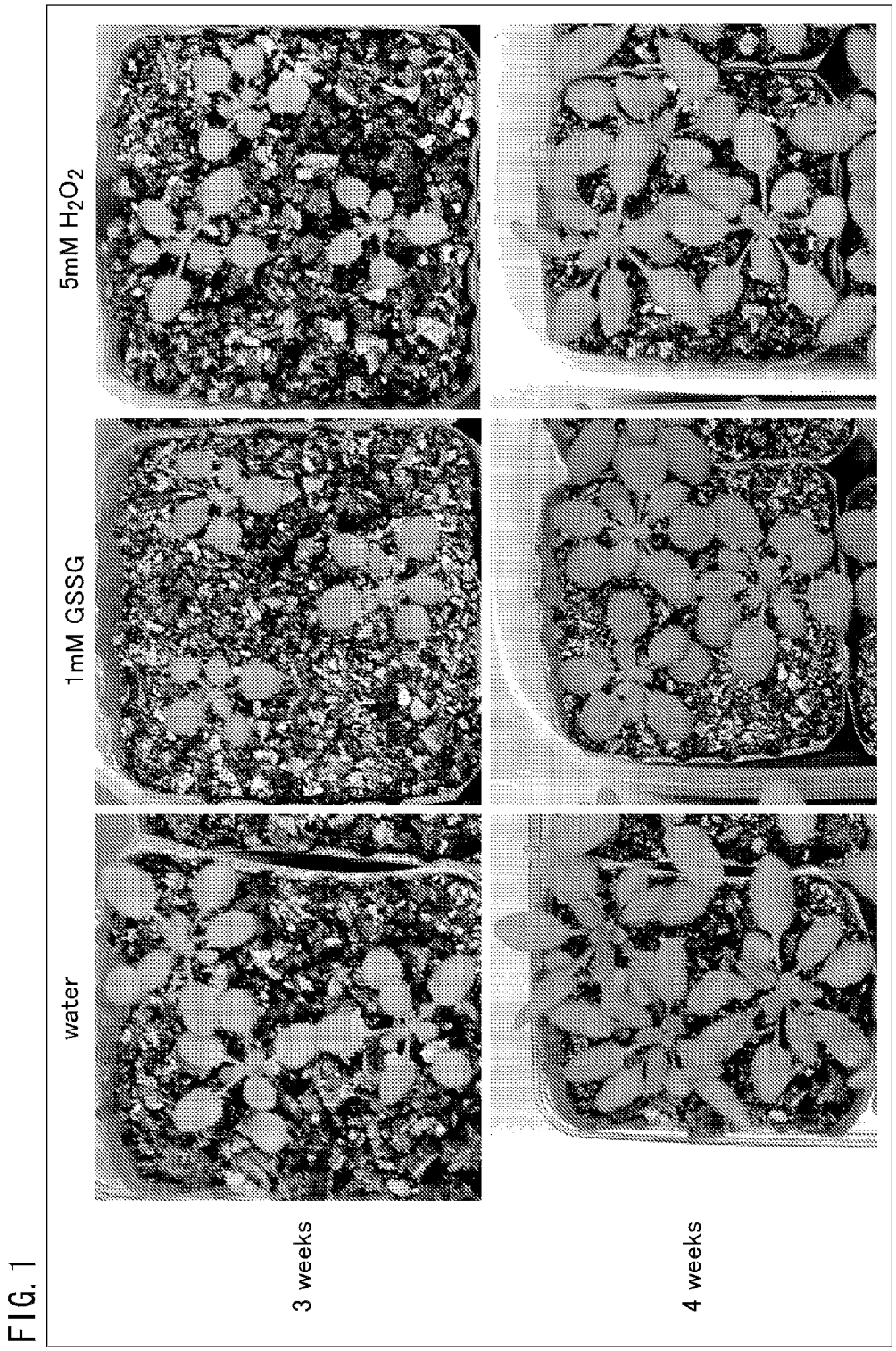
FIG. 1 is a drawing illustrating states of *Arabidopsis* treated with water, a GSSG solution, or an $H_2O_2$ solution, observed 3 or 4 weeks after sowing.

One embodiment of the present invention is described below with reference to the attached drawings. Note that the present invention is not limited to the embodiment.

A plant growth regulator of the present invention is not particularly limited as long as it contains glutathione, and specific factors of the plant growth regulator such as density and other components etc. are not particularly limited. The glutathione may be reduced glutathione (which may be hereinafter referred to as "GSH") or may be an oxidized glutathione (which may be hereinafter referred to as "GSSG"), but GSSG is preferable.

As is well known by a person skilled in the art, GSH has a property of easy oxidation. Consequently, when GSH is added as glutathione to the plant growth regulator of the present invention, the plant growth regulator generally contains not a small amount of GSSG. That is, the plant growth regulator of the present invention may contain, as glutathione, GSH and GSSG in a mixed state.

The plant growth regulator of the present invention may be arranged so as to contain GSH as glutathione and the GSH is oxidized to be GSSG when the plant growth regulator is stored or used. Further, GSH may be oxidized to be GSSG after the plant growth regulator was supplied to a plant.

A method for oxidizing GSH to be GSSG is not particularly limited. For example, GSH can be easily changed to GSSG by air oxidization. Alternatively, GSH may be changed to GSSG by any conventional artificial method that has been publicly known so far.

"Oxidized glutathione" in the present invention is a substance that is well known by a person skilled in the art and does not require any special explanation. For example, "oxidized glutathione" may be defined as a molecule obtained by disulfide-bonding two-molecular reduced glutathiones.

In general, it is known that most (98% or more) of glutathione in cells of an organism is reduced glutathione. Consequently, a person skilled in art would conceive reduced glutathione as glutathione, and therefore use of oxidized glutathione is not general. Further, a person skilled in the art has an impression that oxidized glutathione worsens growth of plants. Therefore, a person skilled in the art would not have been motivated to use oxidized glutathione for cultivation of plants.

Under such a situation, the inventors have found that functions of fructose-1,6-bisphosphate aldolase that is an enzyme for Calvin cycle are controlled by bonding with glutathione. The inventors have added oxidized glutathione necessary for the bonding from outside, succeeding in greatly increasing the productivity of biomass and the yield.

That is, the inventors of the present invention have found that cultivation of a plant by use of "oxidized glutathione (GSSG)" that has not been generally used in cultivation of plants allows greatly increasing the number of seeds of the plant and the number of flowers of the plant, and thus completed the present invention. Therefore, the present invention has a significant originality.

The plant growth regulator of the present invention contains glutathione and increases harvest index of plants.

In the present specification, "harvest index" indicates a ratio of the weight of harvest to the weight of a plant as a whole. In other words, "harvest index" indicates a ratio of the amount of biomass of the harvest to the amount of all biomass of individual plants.

In the present specification, "harvest" indicates a portion of a plant to be eaten. For example, in a case of a plant whose fruit is to be eaten, the "harvest" is the fruit. In a case of a plant whose seed is to be eaten, the "harvest" is the seed. In a case of a plant whose stem is to be eaten, the "harvest" is the stem. In a case of a plant whose root is to be eaten, the "harvest" is the root. In a case of a plant whose flower is to be eaten, the "harvest" is the flower. In a case of a plant whose leaf is to be eaten, the "harvest" is the leaf. Further, the "harvest" indicates a portion that is not edible but contains a product targeted in cultivating a plant. Specifically, in a case of ornamental plants, examples of the "harvest" include flowers, stems, leaves, roots, seeds etc. each of which is to be appreciated.

Further, in the present invention, "increasing harvest index" indicates an effect of increasing harvest index compared with a condition under which the plant growth regulator of the present invention is not supplied, and indicates that a ratio of the amount of biomass of the harvest to the amount of all biomass can be increased under a conventional and standard fertilization condition that is optimized to obtain the maximum amount of yield per unit area. Although the amount of yield per unit area increases as a planting rate increases, this effect gets saturated at a certain planting rate. "Increasing harvest index" in the present specification indicates that a ratio of the amount of biomass of harvest to the amount of all biomass can be increased even under such a planting condition.

Since the plant growth regulator of the present invention allows increasing harvest index of a plant, it is possible not only to increase the amount of foods or biomass resources produced per unit area but also to greatly contribute to increased production of industrially applicable plants and harvests obtained therefrom.

Further, it is preferable that the plant growth regulator of the present invention increases the number of seeds of a plant and/or the number of flowers of the plant. As described in later-mentioned Examples, it is clearly demonstrated that use of the plant growth regulator of the present invention allows increasing the number of seeds and the number of flowers. Further, it is also demonstrated that other performance of the plant growth regulator of the present invention is lengthening of the life of a plant, causing a leaf to be more round and larger, shortening the plant length, and thickening a stem of the plant.

This allows increasing the yield of seeds for example. Therefore, industrial applicability of the plant growth regulator is quite high not only in a case of selling seeds themselves but also in a case of seeds containing fats and oils and other effective components since the yields of such fats and oils etc. also increase. Further, such increased yields are also useful for biomass material production.

When the plant growth regulator is applied to ornamental plants or shade trees, the performance of lengthening the life of a plant allows extending the interval of exchanging plants due to withering of the plants. This reduces work burden on maintenance of the ornamental plants or the shade trees. Further, the performance of causing a leaf to be more round and larger is applicable to production of unique ornamental plants having unusual appearances. Further, the performance of shortening the plant length and thickening a stem of the plant is applicable to production of ornamental plants and to increasing durability of crops against strong winds.

Further, it is preferable that the plant growth regulator of the present invention increases the number of lateral shoots and/or tillers of plants. As explained in later-mentioned Examples, this invention is made on a new finding that when a plant having mutation in function for synthesizing plant hormone (gibberellin) or function for responding to plant hormone is cultivated by use of oxidized glutathione, the number of lateral shoots increases greatly. As the number of lateral shoots and/or tillers increases, the number of flowers (sheaths) increases.

Therefore, when the plant growth regulator of the present invention is applied to a plant such as gramineae whose tillers have a great influence on the yield, it is possible to increase the yield of seeds.

The target plant to which the plant growth regulator is to be applied is preferably a plant having mutation in function for synthesizing plant hormone or responding to plant hormone. This is because application of glutathione, preferably oxidized glutathione to the mutant or a transformant having the same function as the mutant allows further exerting the performance of the oxidized glutathione.

Herein, "a plant having mutation in function for synthesizing plant hormone or responding to plant hormone" indicates a plant which has mutation in at least one of an enzyme of a biosynthesis system of plant hormone, a receptor of plant hormone, a biological substance of a communication system of plant hormone etc. and which is a plant whose function concerning plant hormone does not work compared with a wild-type plant or which is a plant highly susceptive (acquired) to plant hormone due to mutation. In particular, it is preferable to use a mutant whose function concerning plant hormone is lower than that of a wild-type or whose function concerning plant hormone is substantially lost.

An example of the plant is, as explained in later-mentioned Examples, a mutant in which a DNA fragment such as T-DNA is inserted into a gene encoding an enzyme of a biosynthesis system of plant hormone.

The plant hormone is preferably gibberellin. It is considered that oxidized glutathione functions at the downstream of plant hormone such as gibberellin or in corporation with plant hormone.

Further, it is preferable that the plant growth regulator of the present invention promotes growth of a sprout, induction of a floral bud, and/or anthesis. As explained in the later-mentioned Examples, it is clearly demonstrated that the plant growth regulator of the present invention promotes growth of a sprout, induction of a floral bud, and/or anthesis.

This allows shortening the length of cultivating a plant and increasing productivity of the plant. In a case of a plant used as foods, this performance contributes to increasing production of foods. Further, since the plant growth regulator allows controlling anthesis or growth of a plant, application of the plant growth regulator allows effective production of a plant. This allows regulating supply of the plant to the market in response to demand of the market.

Further, it is preferable that the plant growth regulator of the present invention promotes growth of roots of a plant. As explained in the later-mentioned Examples, it is clearly demonstrated that use of the plant growth regulator of the present invention promotes growth of roots of a plant.

This allows obtaining a large number of harvests from a plant whose roots are harvests in a short time. Therefore, application of the plant growth regulator to a plant whose roots are edible allows increasing production of foods.

Further, it is preferable that the plant growth regulator of the present invention prevents deterioration of growth due to lack of nitrogen. It is known that shortage or lack of a nitrogen source generally reduces growth of a plant. However, as explained in the later-mentioned Examples, even when a plant is cultivated under a nitrogen-deficient condition, application of the plant growth regulator of the present invention allows preventing deteriorated growth due to lack of a nitrogen source.

Therefore, even when a plant suffers from deteriorated growth due to lack of nitrogen, application of the plant growth regulator to the plant allows promotion of the growth of the plant.

In a case where the plant growth regulator contains oxidized glutathione, the amount of glutathione is not particularly limited. In a case of *Arabidopsis*, the amount of glutathione is preferably 10 µM-20 mM, more preferably 0.2 mM-5 mM, and further more preferably 0.5 mM-2 mM.

On the other hand, in a case where the plant growth regulator contains reduced glutathione, the amount of reduced glutathione is preferably larger than that of oxidized glutathione to be contained in the plant growth regulator. Specifically, in a case of *Arabidopsis*, the amount of reduced glutathione is preferably 100 uM-40 mM, more preferably 0.4 mM-20 mM, and further more preferably 4 mM-10 mM.

In the case where the plant growth regulator contains reduced glutathione in the above range, when 50% of reduced glutathione is oxidized while preserving or using the plant growth regulator, the concentration of oxidized glutathione in the plant growth regulator ranges at least from 1 mM to 2.5 mM. This yields substantially the same effect as when the plant growth regulator contains 1 mM-2.5 mM of oxidized glutathione. Oxidization of 50% of reduced glutathione in the plant growth regulator easily occurs because of properties of the reduced glutathione. This can be easily understood by a person skilled in the art.

In a case of supplying a specific amount of solution as explained in the later-mentioned Examples, when the amount of oxidized glutathione or reduce glutathione is in the above range, it is possible to control growth of a plant appropriately. Note that the above concentration range is a range in a case of supplying a specific amount of solution to *Arabidopsis*. Change of the amount to be supplied or change of the kinds of plants (e.g. tree etc.) may allow oxidized glutathione or reduced glutathione with higher concentration to be supplied. In some cases, it is possible to realize the performance of the plant growth regulator of the present invention with oxidized glutathione or reduced glutathione with lower concentration.

The feature of the present invention is based on the finding that oxidized glutathione increases the number of seeds and/or the number of flowers of a plant, lengths the life of the plant, causes a leaf to be more round and larger, increases the number of lateral shoots and/or tillers, and increases the number of flowers (sheaths) in accordance with an increase in the number of lateral shoots etc. so as to increase the yield of seeds, and other limitation is not intended. Therefore, the concentration range in the present invention is not limited to the above range.

How to supply the plant growth regulator of the present invention to a plant is not particularly limited, and the plant growth regulator of the present invention may be used in the same manner as a conventional and publicly known plant growth regulator. For example, in a case where the plant growth regulator of the present invention is in the form of a liquid or emulsion, the plant growth regulator may be sprayed to, dropped on, or applied to not only a vegetative point but also a part of or all of a plant such as a stem and a leaf. In a case where the plant growth regulator of the present invention is in the form of a solid agent or a powder agent, the plant growth regulator may be absorbed into a root via the earth. In a case where a plant is a water plant such as a floating grass, the plant growth regulator of the present invention may be absorbed as an aquarium additive into a root or the plant growth regulator in the form of the solid agent may be dissolved gradually in water. In particular, in a case where the plant growth regulator of the present invention is used for a terrestrial plant, it is preferable that the plant is subjected to a solution culture by use of the plant growth regulator in the form of an aqueous solution.

As long as the plant growth regulator of the present invention contains glutathione (GSH and/or GSSG), other specific components of the plant growth regulator are not particularly limited. For example, in a case where the plant growth regulator is in the form of an aquarium additive or a solid agent, carrier components are solid carriers, examples of which include inorganic materials such as talc, clay, vermiculite, diatomite, kaoline, calcium carbonate, calcium hydroxide, white clay, and silica gel, and flour and starch. In a case where the plant growth regulator is in the form of a liquid agent, carrier components are liquid carriers, examples of which include: water; aromatic hydrocarbons such as xylene; alcohols such as ethanol and ethyleneglycol; ketones such as acetone; ethers such as dioxane and tetrahydrofuran; dimethylformamide; dimethylsulfoxide; and acetonitrile.

Further, the plant growth regulator of the present invention may contain other adjuvant if necessary. Examples of the adjuvant include: negative ion surfactants such as ester alkylsulfates, alkyl sulfonate, alkylaryl sulfonate, and dialkyl sulfosuccinate; positive ion surfactants such as salts of higher aliphatic amine; non-ion surfactants such as polyoxyethyleneglycol alkylether, polyoxyethyleneglycol acylester, polyoxyethyleneglycol multivalent alcohol acylester, and cellulose derivative; and a thickener such as gelatin, casein, and gum Arabic; a filler; and a binder.

If necessary, other plant growth regulator such as benzoic acid, nicotine acid, nicotine acid amide, and pipecolic acid may be added to a product in such an amount that does not prevent an intended effect of the present invention. Further, a conventional and well-known fertilizer may be added to the product.

A plant to which the plant growth regulator of the present invention is to be supplied is not particularly limited, and the plant growth regulator may be supplied to every kinds of plants such as monocotyledons, dicotyledons, and trees. Examples of monocotyledons include: Lemnaoideae including *Spirodela* (floating grass) and *Lemna* (*L. perpusilla* and *L. trisulca*); Orchidaceae including *Cattleya, Cymbidium, Dendrobium, Phalaenopsis, Vanda, Paphiopedilum*, and *Oncidium*; Typhaceae; Sparganiaceae; Potamogetonaceae; Najadaceae; Scheuchzeriaceae; Alismataceae, Hydrocharitaceae; Triuridaceae; Poaceae; Cyperaceae; Arecaceae; Araceae; Eriocaulaceae; Commelinaceae; Pontederiaceae; Juncaceae; Stemonaceae; Liliaceae; Amaryllidaceae; Dioscoreaceae; Iridaceae; Musaceae; Zingiberaceae; Cannaceae; and Burmanniaceae.

Examples of dicotyledonous include: Convolvulaceae including *Pharbitis* (morning glory), *Calystegia* (*Calystegia japonica, Calystegia hederacea*, and *Calystegia soldanella*), *Ipomoea* (*Ipomoea pes-caprae, Ipomoea batatas*), and *Cuscuta* (*Cuscuta japonica, Cuscuta australis*); Caryophyllaceae including *Dianthus* (*Dianthus caryophyllus* etc.), *Stellaria, Minuartia, Cerastium, Sagina, Arenaria, Moehringia, Pseudostellaria, Honckenya, Spergula, Spergularia salina, Silene, Lychnis, Melandryum*, and *Cucubalus;* Casuarinaceae; Saururaceae; Piperaceae; Chloranthaceae; Salicaceae; Myricaceae; Juglandaceae; Betulaceae; Fagaceae; Ulmaceae; Moraceae; Urticaceae; Podostemaceae; Proteaceae; Olacaceae; Santalaceae; *Viscum album;* Aristolochiaceae; Mitrastemonaceae; Balanophoraceae; Polygonaceae; Chenopodiaceae; Amaranthaceae; Nyctaginaceae; Theligonaceae; Phytolaccaceae; Tetragoniaceae; Portulacaceae; Magnoliaceae; Trochodendraceae; Cercidiphyllaceae; Nymphaeaceae; Ceratophyllaceae; Ranunculaceae; Lardizabalaceae; Berberidaceae; Menispermaceae; Calycanthaceae; Lauraceae; Papaveraceae; Capparaceae; Brassicaceae; Droseraceae; Nepenthaceae; Crassulaceae; Saxifragaceae; Pittosporaceae; Hamamelidaceae; Platanaceae; Rosaceae; Fabaceae; Oxalidaceae; Geraniaceae; Linaceae; Zygophyllaceae; Rutaceae; Simaroubaceae; Meliaceae; Polygalaceae; Euphorbiaceae; Callitrichaceae; Buxaceae; Empetraceae; Coriariaceae; Anacardiaceae; Aquifoliaceae; Celastraceae; Staphyleaceae; Icacinaceae; Aceraceae; Hippocastanaceae; Sapindaceae; Sabiaceae; Balsaminaceae; Rhamnaceae; Vitaceae; Elaeaocarpaceae; Tiliaceae; Malvaceae; Sterculiaceae; *Actinidia arguta;* Theaceae; Clusiaceae; Elatinaceae; Tamaricaceae; Violaceae; Flacourtiaceae; Stachyuraceae; Passifloraceae; Begoniaceae; Cactaceae; Thymelaeaceae; Elaeagnaceae; Lythraceae; *Punica granatum;* Rhizophoraceae; Alangiaceae; Melastomataceae; Trapaceae; Onagraceae; Haloragaceae; Hippuridaceae; Araliaceae; Apiaceae; Cornaceae; Diapensiaceae; Clethraceae; Pyrolaceae; Ericaceae; Myrsinaceae; Primulaceae; Plumbaginaceae; Ebenaceae; Symplocaceae; Styracaceae; Oleaceae; Buddlejaceae; Gentianaceae; Apocynaceae; Asclepiadaceae; Polemoniaceae; Boraginaceae; Verbenaceae; Lamiaceae; Solanaceae; Scrophulariaceae; Bignoniaceae; Pedaliaceae; Orobanchaceae; Gesneriaceae; Lentibulariaceae; Acanthaceae; Myoporaceae; Phrymaceae; Plantaginaceae; Rubiaceae; Caprifoliaceae; Adoxaceae; Valerianaceae; Dipsacaceae; Cucurbitaceae; Campanulaceae; and Asteraceae.

The plant to which the plant growth regulator is supplied may be a mutant or a transformant of the above plant as well as a wild-type of the above plant. As explained in the later-mentioned Examples, application of the plant growth regulator of the present invention to a transformant plant to which a specific gene is introduced increases the effect of the plant growth regulator of the present invention (in other words, application of the plant growth regulator of the present invention to such transformant yields a greater effect than application of the plant growth regulator of the present invention to a wild-type plant).

Therefore, such transformant plant may be regarded as an object to which the plant growth regulator of the present invention is preferably applied.

A specific example of such transformant is a transformant plant to which a gene for encoding glutathione-binding plastid-type fructose-1,6-bisphosphate aldolase (which may be hereinafter referred to as "gFBA") is introduced.

As explained in the later-mentioned Examples, it is demonstrated that application of the plant growth regulator of the present invention to a transformant plant to which a gFBA gene is introduced allows the plant growth regulator to further enhance the effect of increasing harvest index.

A transformant plant to which the gFBA gene is introduced and a method for producing the transformant plant are described in International Application Publication No. WO 2007/091634A1 (published on Aug. 16, 2007) etc. Therefore, the contents of the International Application Publication serve as a reference for the present specification.

The plant growth regulator of the present invention may be applied to various organisms, organs, tissues, or cells by a method suitable for the form of the plant growth regulator.

Further, a seed obtained from a plant treated with the plant growth regulator of the present invention is industrially useful and is encompassed in the present invention. As explained in the later-mentioned Examples, analysis of ripeness (germination rate) of such seed showed that such seed germinated faster than a normal seed. Therefore, it may be considered that a seed obtained from a plant cultivated with glutathione, preferably oxidized glutathione, has a higher ripeness.

A treatment with the plant growth regulator of the present invention may be performed in such a manner that the plant growth regulator with appropriate concentration is used before and/or while normally cultivating a seed or callus of a target plant. Normally, it is effective to use the plant growth regulator in a treatment suitable for the nature (such as long-day property, short-day property) of the target plant. Since such treatment is well known to a person skilled in the art, detailed explanations thereof are omitted here. For example, in a case of a relative long-day plant, it is effective to use the plant growth regulator of the present invention while irradiating light with predetermined intensity or more.

Therefore, the present invention encompasses use of the plant growth regulator in a method of growing any plant (method of producing a plant) that is normally used in the field to which the present invention pertains.

The plant growth regulator of the present invention may be made of only glutathione that is an effective component. However, it is preferable that the plant growth regulator of the present invention is used in the form applicable to individual plants, such as a liquid agent, a solid agent, a powder agent, an emulsion, and an aquarium additive. Such agent may be produced through a conventional method by appropriately adding, to glutathione that is an effective component, a publicly known carrier and an adjuvant etc. that are pharmaceutically usable in individual fields in such an amount that does not impair the effect of the plant growth regulator of the present invention.

Further, the present invention encompasses a method of cultivating a plant by use of the plant growth regulator. That is, the method of cultivating a plant in accordance with the present invention is a method of cultivating a plant by use of glutathione so as to increase harvest index of the plant, and other specific steps and conditions etc. of the method are not particularly limited. In the method, glutathione may be GSH and/or GSSG, but it is preferable that glutathione contains GSSG.

One embodiment of a method of cultivating a plant in accordance with the present invention is explained below. Note that the present invention is not limited to the following embodiment.

In the method of cultivating a plant in accordance with the present invention, glutathione may be supplied to a plant under a condition that allows the plant to always absorb glutathione, or glutathione may be supplied to a plant under a condition that allows a plant to intermittently absorb glutathione during the cultivation (e.g. a condition that glutathione is supplied with an interval, once a week or twice a week). Further, glutathione may be supplied during a specific time, i.e., during a specific growth time.

Intermittently supplying glutathione allows reducing the amount of glutathione to be supplied. This reduces costs for cultivating a plant. In the case of intermittently supplying glutathione, it is preferable to supply glutathione at a constant interval. Alternatively, glutathione may be supplied at an inconstant interval.

The interval at which glutathione is supplied is not particularly limited, and may be determined in accordance with concentration of glutathione to be supplied, a plant to which glutathione is to be supplied, and a time (more specifically, a growth time) when glutathione is to be supplied. Generally, in a case where a plant to which glutathione is to be supplied is a herbaceous plant, it is preferable that glutathione is supplied once a week or twice a week or supplied at the same time as the time of additional fertilization.

In the case of supplying glutathione at a specific time, it is preferable to supply glutathione around at the time of transition from vegetative to reproductive development (including the time of transition from vegetative to reproductive development) or at the time of forming a floral bed after the transition from vegetative to reproductive development or at the time of translocation to a target harvest. This allows effectively obtaining the effect yielded by supplying glutathione. Further, since glutathione is supplied only at a specific time, it is possible to reduce costs for cultivating a plant.

In the case of supplying glutathione only at a specific time, glutathione may be supplied to a plant under a condition that allows the plant to always absorb glutathione during a predetermined period in the specific time, or glutathione may be supplied to a plant under a condition that allows the plant to intermittently absorb glutathione during a predetermined period in the specific time. Intermittently supplying glutathione during a predetermined period in the specific time allows further reducing costs for cultivating a plant.

Further, the present invention encompasses a method of increasing the number of seeds of a plant and/or the number of flowers of the plant. In the method, too, glutathione may be oxidized glutathione or reduced glutathione. It is preferable that glutathione includes oxidized glutathione.

In the method, a time at which glutathione is supplied to a plant and the amount of glutathione to be supplied to the plant etc. is not particularly limited. It is preferable that glutathione is supplied under the condition explained in the method of cultivating a plant.

Further, the present invention encompasses a plant obtained by the above method. The plant in accordance with the present invention shows a higher harvest index. Since the plant in accordance with the present invention shows a higher harvest index than a plant cultivated under a normally recommended condition, measurement of the harvest index allows clearly distinguishing the plant in accordance with the present invention from a plant obtained by a method other than the method of the present invention.

Further, such a plant can be easily and clearly distinguished from a plant obtained by a method other than the method of the present invention by examining the amount or the rate of oxidized glutathione in the plant. Other than the method of examining the amount and concentration of oxidized glutathione in a plant, it is possible to distinguish the plant in accordance with the present invention from a plant obtained by a method other than the method of the present invention by comparing gene expression patterns by use of a DNA micro allay etc. Specifically, the gene expression pattern of a plant cultivated with oxidized glutathione is examined in advance, and is compared with that of a plant cultivated by a method other than the method of the present invention so as to specify an expression pattern specific to a case of supplying oxidized glutathione (GSSG expression pattern). The expression pattern of a plant to be examined is examined, and is compared with the GSSG expression pattern. Thus, it is possible to easily determine whether the plant to be examined is a plant in accordance with the present invention or not.

Further, such a plant can be clearly distinguished from a plant cultivated by a method other than the method of the present invention by measuring the harvest index of the plant.

The methods as explained above (i.e. the methods for specifying a plant of the present invention) may be carried out singularly or in combination. Carrying out the methods in combination allows further clearly distinguishing the plant of the present invention from a plant cultivated by a method other than the method of the present invention.

The following more details the present Embodiment with reference to Examples. Note that the present invention is not limited to the following Examples, and various modifications are possible with respect to details of the present invention. Further, the present invention is not limited to the description of the embodiments above, but may be altered by a skilled person within the scope of the claims. An embodiment based on a proper combination of technical means disclosed in different embodiments is encompassed in the technical scope of the present invention.

EXAMPLES

<1. Influence of Oxidized Glutathione on Growth of *Arabidopsis*>

*Arabidopsis* was cultivated with light of 100 μE/m2 at 22° C. under a day length condition that a light period is 16 hours and a dark period is 8 hours, by use of a culture medium with two parts of vermiculite (Asahi Kogyo, Inc.) in a lower layer, one part of The Kureha Ikubyou Baido soil (Kureha) in a middle layer, and one part of vermiculite (Asahi Kogyo, Inc.) in an upper layer. Normally, *Arabidopsis* cultivated under these conditions does not exhibit the symptom of lacking nitrogen without additional fertilization.

In the present test, the states of the growing plants were observed while the plants were treated with only water, a 1 mM oxidized glutathione (GSSG) solution, or a 5 mM $H_2O_2$ solution. Specifically, the plants were cultivated with two or three plants in one pod of approximately 65 in width, 65 in depth, and 50 in height, and an appropriate amount of a treatment solution was supplied.

The effect of the treatment was evaluated with respect to the number of rosette leaves, the speed of a growing flower stalk, the number of flowers, and the number of seeds. The results are shown in FIGS. 1-5.

As shown in FIG. 1, it was found that 3-4 weeks after sowing, leaves of the plant cultivated with the 1 mM GSSG solution grew larger and rounder than leaves of the plant cultivated with only water and than leaves of the plant cultivated with the 5 mM $H_2O_2$ solution.

Figure 2:
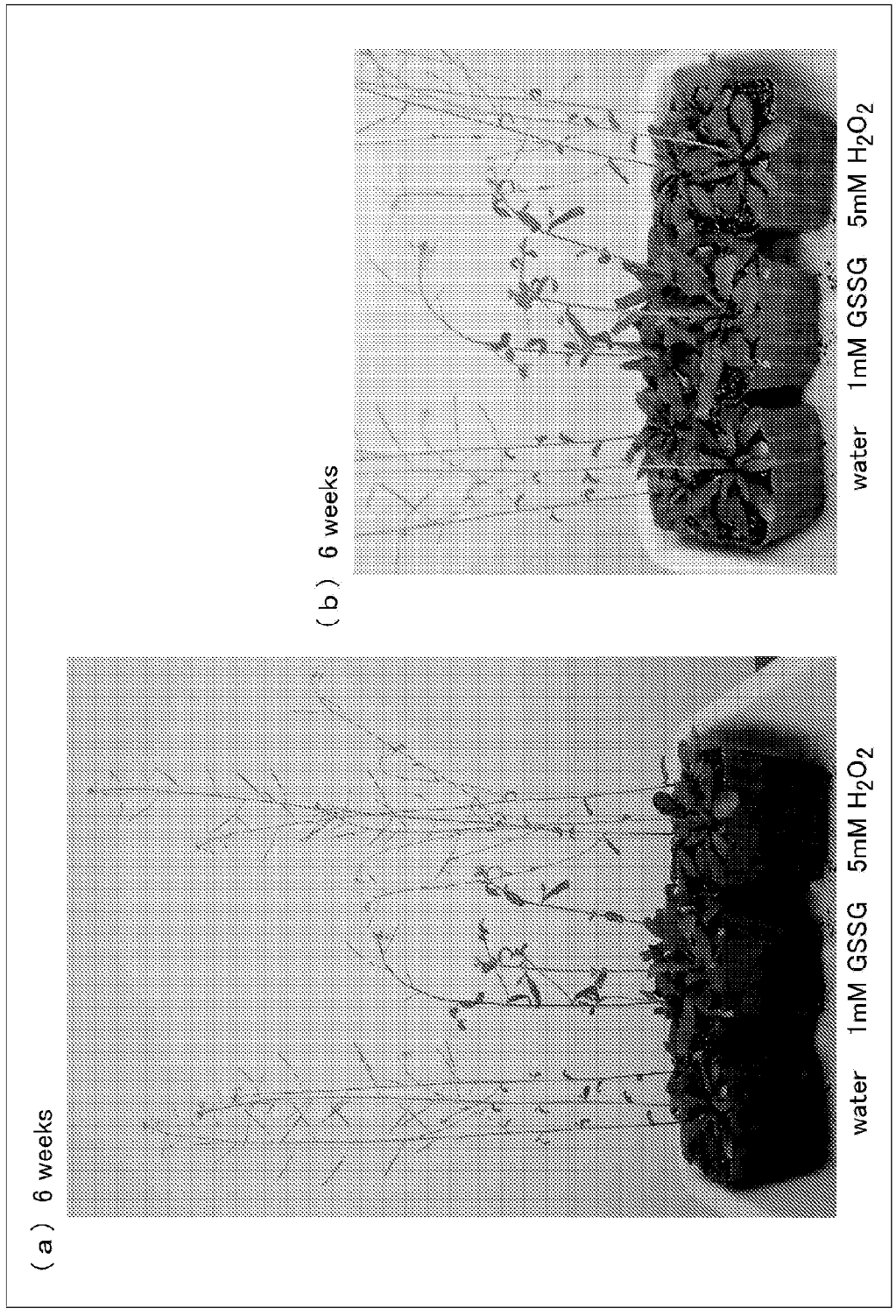
FIG. 2 is a drawing illustrating states of *Arabidopsis* treated with water, a GSSG solution, or an $H_2O_2$ solution, observed 6 weeks after sowing.

Further, as shown in (a) and (b) of FIG. 2, it was found that 6 weeks after the sowing, the plant cultivated with the 1 mM GSSG solution grew to have a shorter plant length, a thicker stem, and larger leaves than the plant cultivated with only water and the plant cultivated with the 5 mM $H_2O_2$ solution. (a) and (b) of FIG. 2 are photographs of the same sample taken in different angles.

Figure 3:
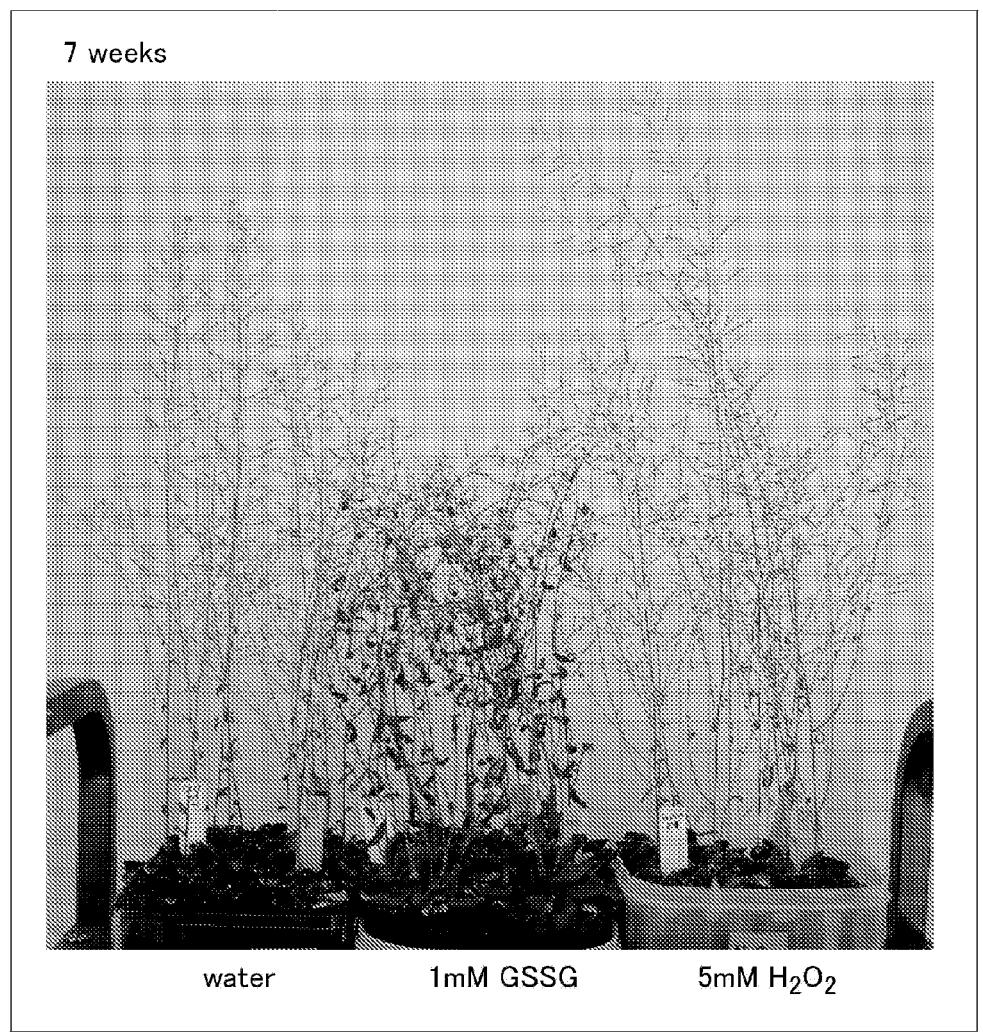
FIG. 3 is a drawing illustrating states of *Arabidopsis* treated with water, a GSSG solution, or an $H_2O_2$ solution, observed 7 weeks after sowing.

Further, as shown in FIG. 3, it was found that 7 weeks after the sowing, the number of flowers and the area of leaves of the plant cultivated with the 1 mM GSSG solution were greatly larger than those of the plant cultivated with only water and the plant cultivated with the 5 mM $H_2O_2$ solution.

Figure 4:
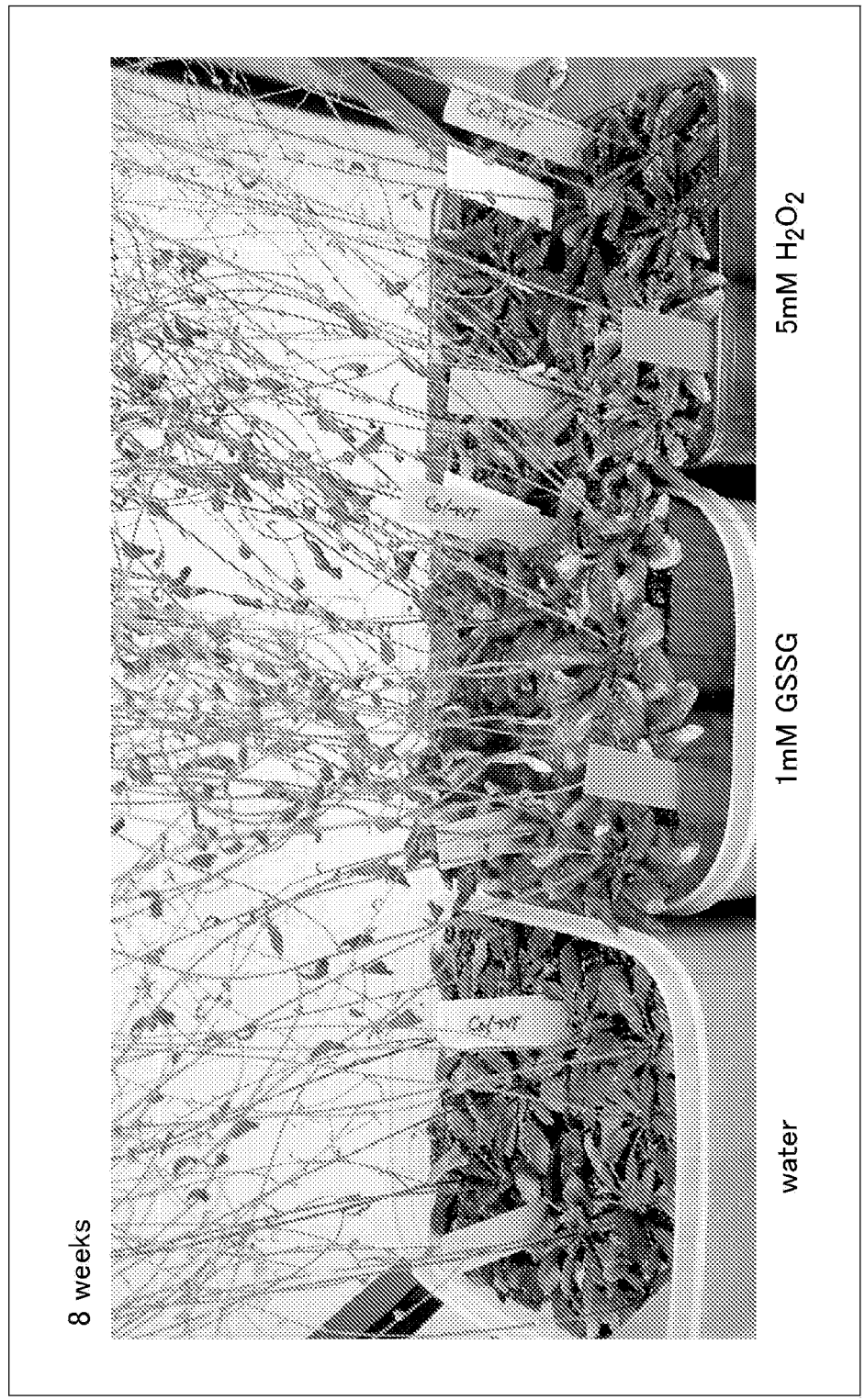
FIG. 4 is a drawing illustrating states of *Arabidopsis* treated with water, a GSSG solution, or an $H_2O_2$ solution, observed 8 weeks after sowing.

Further, as shown in FIG. 4, it was found that 8 weeks after the sowing, the plant cultivated with only water and the plant cultivated with the 5 mM $H_2O_2$ solution were withering, whereas the plant cultivated with the 1 mM GSSG solution showed much amount of green leaves. This shows that the plant cultivated with the 1 mM GSSG solution elongated its life.

Figure 5:
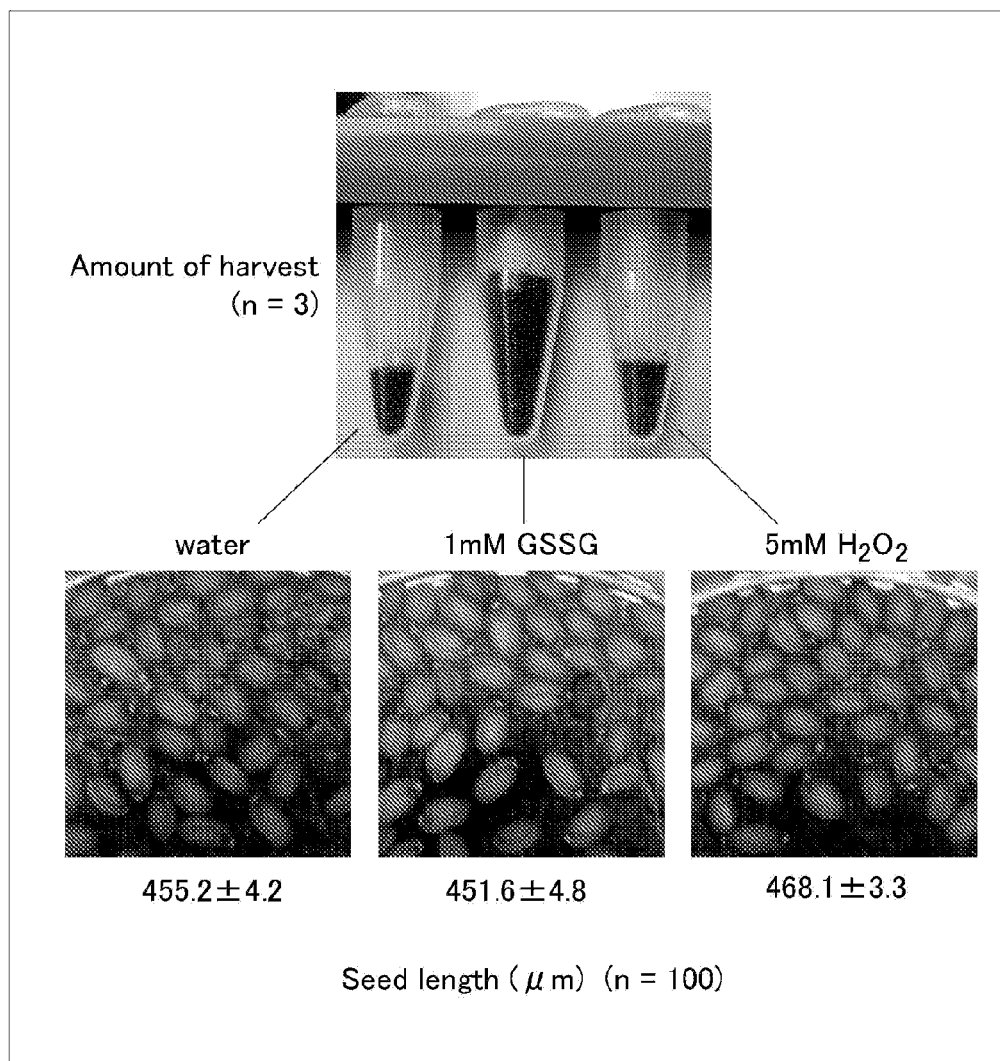
FIG. 5 is a drawing illustrating yields and states of seeds obtained from *Arabidopsis* treated with water, a GSSG solution, or an $H_2O_2$ solution.

Further, as shown in FIG. 5, it was found that the yield of seeds of the plant cultivated with the 1 mM GSSG solution was greatly larger than the yield of seeds of the plant cultivated with water and than the yield of seeds of the plant cultivated with the 5 mM $H_2O_2$ solution. The result of the measurement showed that the effective number of seeds per plant of the plant cultivated with the 1 mM GSSG solution was approximately three or four times as large as the effective number of seeds per plant of the plant cultivated with only water and the plant cultivated with the 5 mM $H_2O_2$ solution (see the upper photograph in FIG. 5).

Further, it was examined whether any differences in the shape of a seed and the size of a seed were observed. The result of the examination was shown by the lower photographs in FIG. 5. As shown in FIG. 5, seeds obtained from the plant cultivated with the 1 mM GSSG solution had substantially the same shape and the same size as those obtained from the plant cultivated with only water. It was found that seeds obtained from the plant cultivated with the 5 mM $H_2O_2$ solution were a bit larger.

The above results clearly show that cultivating a plant by use of oxidized glutathione increases the number of seeds and/or the number of flowers.

<2. Effect of Concentration of Oxidized Glutathione on Growth of *Arabidopsis*>

The influence of concentration of oxidized glutathione on growth of *Arabidopsis* was examined. Specifically, soil filled in a pod of approximately 65 in width, 65 in depth, and 50 in height was immersed in 0 mM-, 0.01 mM-, 0.2 mM-, 1 mM-, 2 mM-, and 5 mM-GSSG solutions. Seeds of *Arabidopsis* were sown in such a manner that approximately three seeds existed in each pod, and the seeds were observed chronologically 3 weeks after the sowing.

Figure 6:
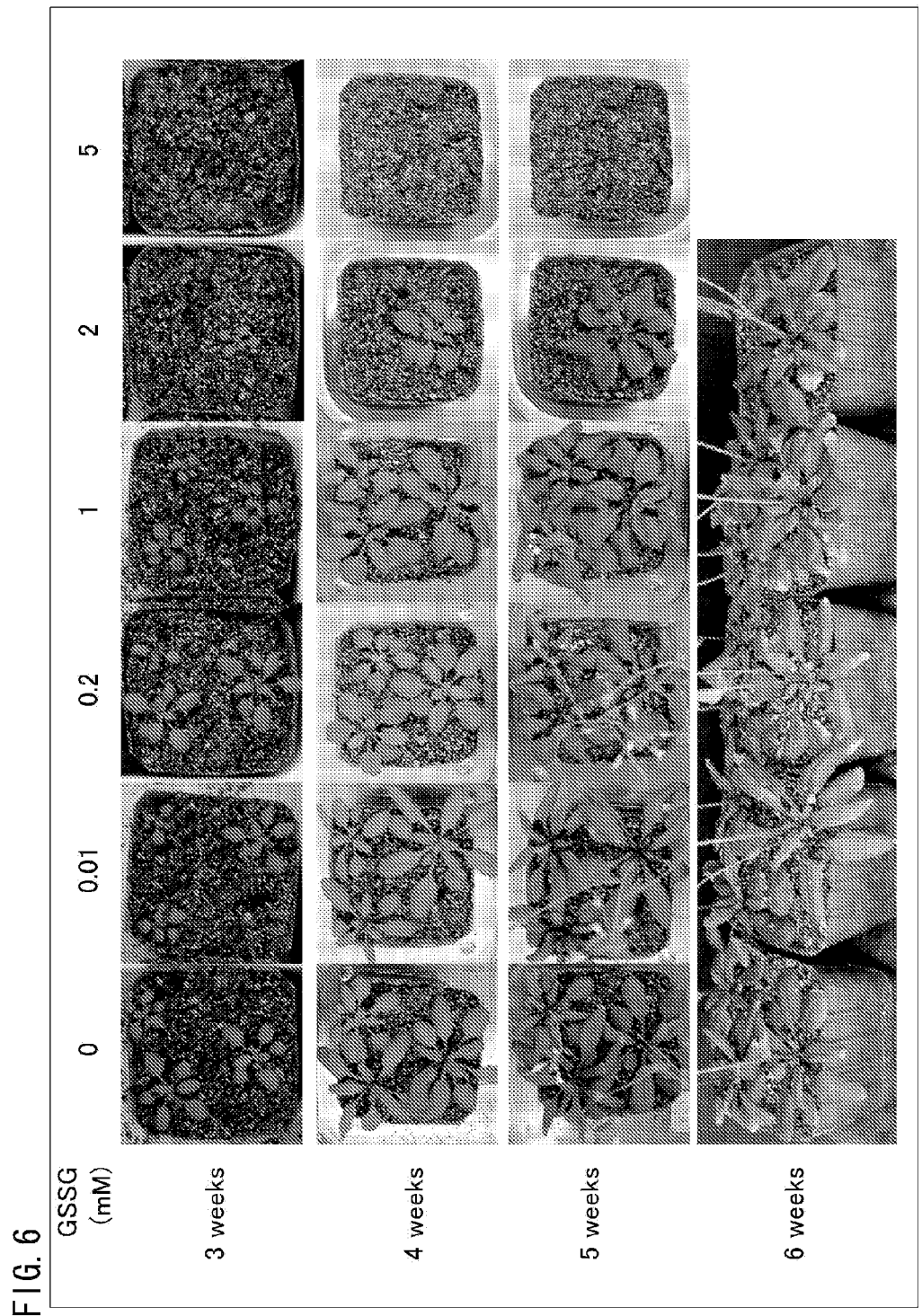
FIG. 6 is a drawing illustrating the result of examination on the influence of concentration of oxidized glutathione on growth of *Arabidopsis*.
Figure 7:
FIG. 7 is a drawing illustrating the result of examination on the influence of concentration of oxidized glutathione on growth of *Arabidopsis*.

The results of the observation are shown in FIGS. 6 and 7. As shown in the drawings, performance of making a leaf rounder and performance of lengthening the life of a plant were clearly observed at concentration of 0.2-2 mM, and performance of making a stem thicker was observed at concentration of 1-2 mM. In a case where concentration of GSSG was 0.01 mM, almost no difference was observed between *Arabidopsis* cultivated with GSSG and *Arabidopsis* cultivated with water (0 mM). In a case where concentration of GSSG was 5 mM, the growth of *Arabidopsis* was greatly prevented and much of *Arabidopsis* withered.

<3. Influence of Oxidized Glutathione on *Arabidopsis* Seeds>

Ripeness of seeds obtained from *Arabidopsis* cultivated with oxidized glutathione was examined. Specifically, seeds obtained from plants cultivated with water or a GSSG solution were sown in 1/2 MS culture media and germination rates of the seeds were examined chronologically.

Figure 8:
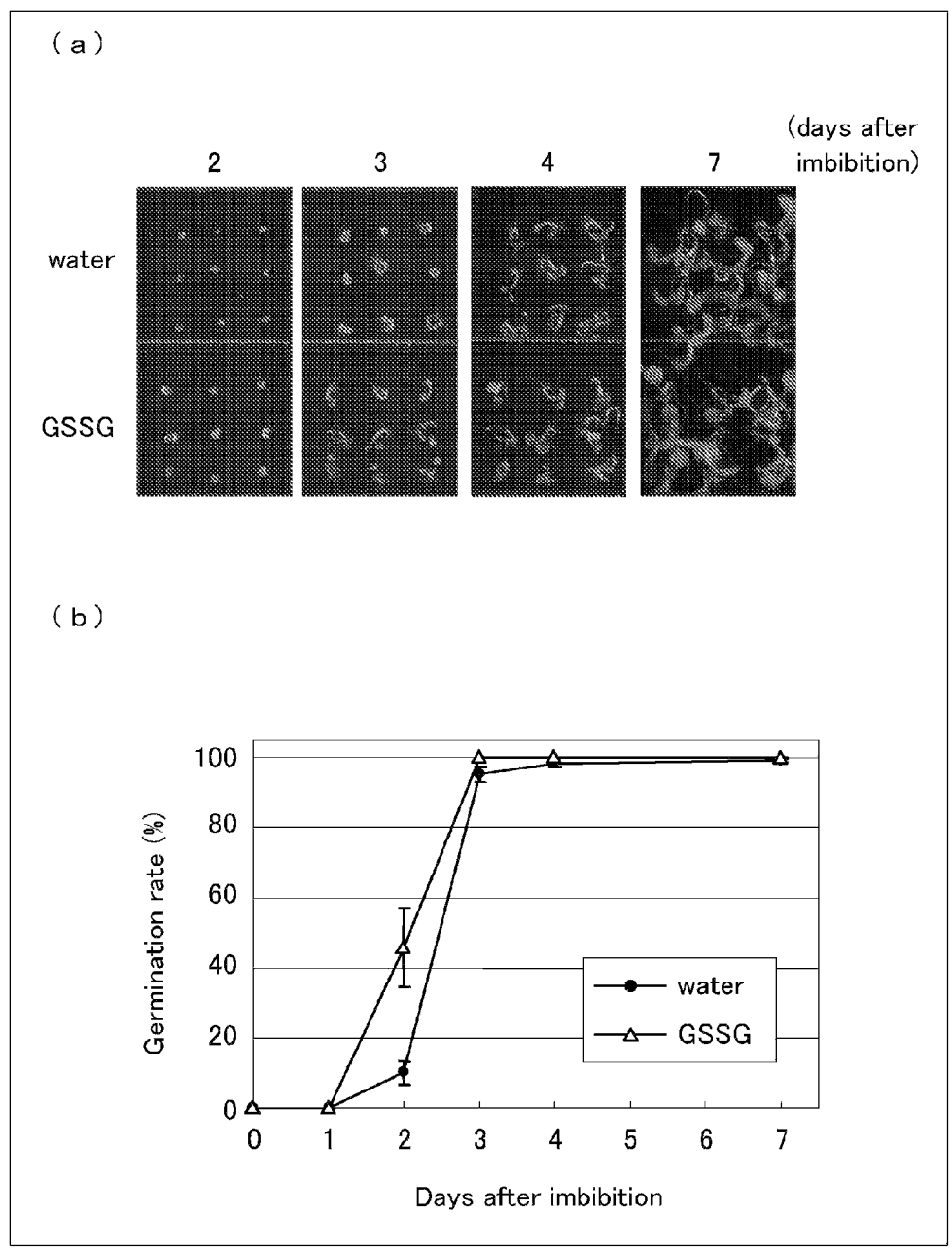
FIG. 8 is a drawing illustrating the result of examination on the influence of oxidized glutathione on seeds of *Arabidopsis*.

The results of the examination are shown in (a) and (b) of FIG. 8. As shown in the drawing, seeds of plants cultivated with the GSSG solution germinated faster than seeds of plants cultivated normally. In particular, the germination rate of the seeds of the plants cultivated with the GSSG solution was significantly high 2 days after the sowing. However, 7 days after the sowing, almost no difference was observed between the seeds of the plants cultivated with the GSSG solution and the seeds of the plants cultivated normally.

<4. Effect of Oxidized Glutathione on Gibberellin Synthesis Mutant>

The effect of oxidized glutathione on gibberellin (GA) synthesis mutant was examined. Specifically, *Arabidopsis* GA synthesis mutants ga20ox1 were cultivated with water or GSSG (1 mM) from the time when they were sown, and the state of their growth was observed.

Figure 9:
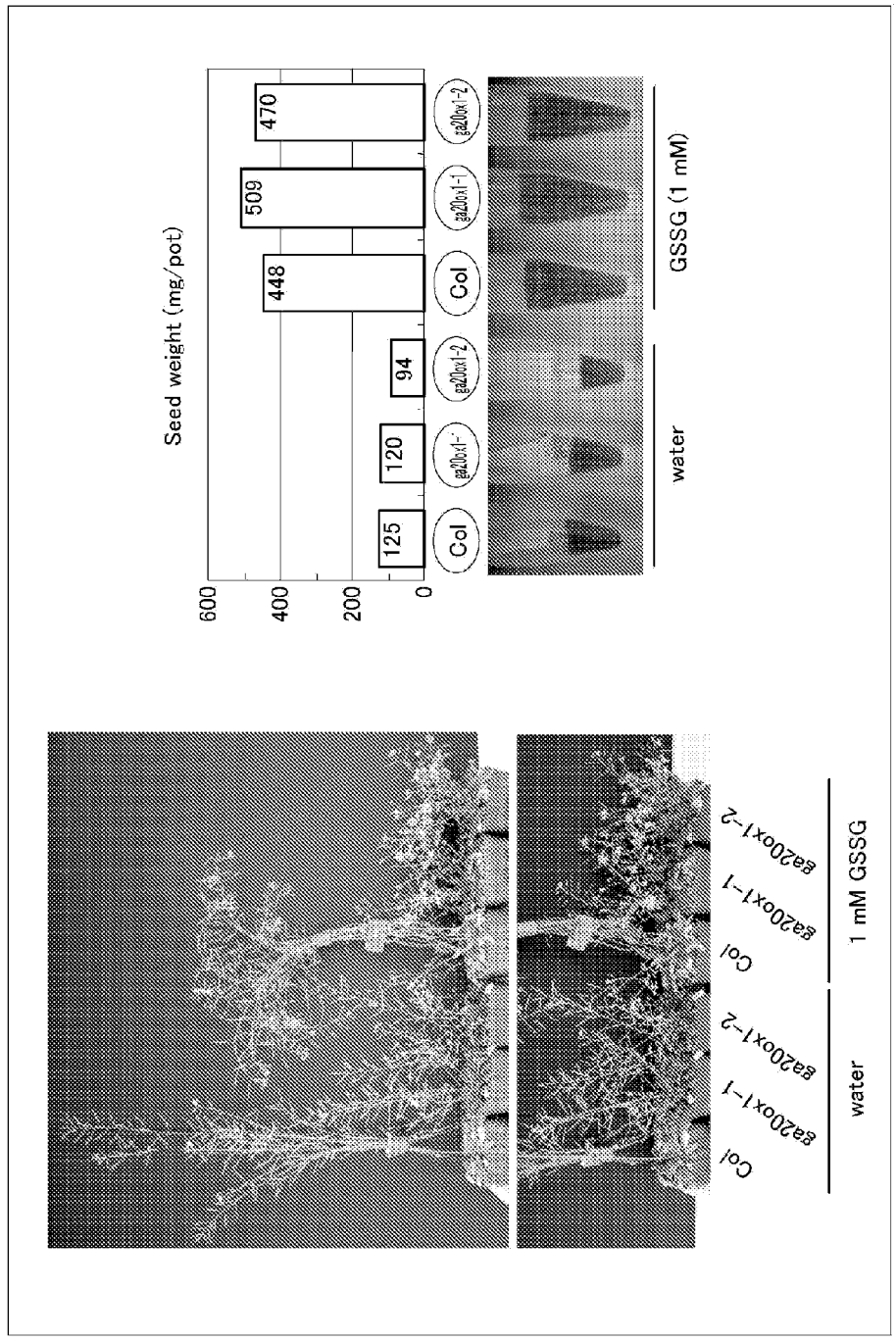
FIG. 9 is a drawing illustrating the result of examination on the influence of oxidized glutathione on a gibberellin synthesis mutant of *Arabidopsis*.

FIG. 9 shows the state of plants 8 weeks after the sowing. The upper photograph of FIG. 9 shows plants observed from the front side, and the lower photograph of FIG. 9 shows the plants observed from the upper oblique direction. In the drawing, "Col" indicates a wild-type Columbia, and "ga20ox1" indicates a mutant in which T-DNA is inserted into a GA20 oxidase gene that codes an enzyme of a GA biosynthesis. "ga20ox1-1" and "ga20ox1-2" are independent mutants in which T-DNA are inserted into different portions.

As illustrated in the drawing, GA mutant ga20ox1 cultivated with GSSG showed significantly increased number of lateral shoots than plants cultivated with water. In accordance with the increase in the number of lateral shoots, the number of flowers (sheaths) also increased. Further, as shown in the right side of FIG. 9, the seed weight significantly increased, too.

Therefore, this method allows increasing the yield of seeds by applying GSSG to a mutant having mutation in synthesis of a plant hormone and reaction to a plant hormone. In particular, the method is effective for a plant such as gramineae whose yield is greatly dependent on tillers. This is evident from the fact that when rice (Akita 63) was cultivated in hydroponics with the standard amount of fertilization being 5 kgN/10a and additional fertilization of 2 kgN/10a was made at the panicle formation stage and the meiotic stage, application of GSSG in the standard amount of 0.2 gN to each test location (0.1 m2) in additional fertilization made the number of ears approximately 1.4 times larger than the number of ears of the plant cultivated with only water.

The plant growth regulator of the present invention contains oxidized glutathione and therefore can promote growth of a plant. For example, the plant growth regulator of the present invention can increase the number of seeds of a plant and/or the number of flowers (sheaths) of a plant.

Further, cultivating with oxidized glutathione a mutant having mutation in synthesis of a plant hormone (e.g. gibberellin) or response to a plant hormone allows greatly increasing lateral shoots, and accordingly allows increasing the number of flowers (sheaths). Consequently, application of the plant growth regulator of the present invention to a plant such as gramineae whose tillers greatly influence the yield allows increasing the number of yield of seeds.

<5. Influence 1 of Treatment Condition of Oxidized Glutathione on Seeds of *Arabidopsis*>

Seeds of *Arabidopsis* were sown in pods filled with soil immersed in 0 mM-, 0.01 mM-, 0.2 mM-, 1 mM-, 2 mM-, and 5 mM-GSSG. The pods were transferred to trays with water containing no GSSG 2 days after, 1 week after, 2 weeks after, 3 weeks after, or 4 weeks after the sowing.

Arabidopsis was cultivated under the same conditions as those described in <1. Influence of oxidized glutathione on growth of Arabidopsis> except for the above condition.

The seed weight per one pod, obtained from Arabidopsis thus cultivated (three plants in each pod), was measured. The results of the measurement are shown in FIGS. 10-12. n is the number of plants that can be finally harvested.

Figure 10:
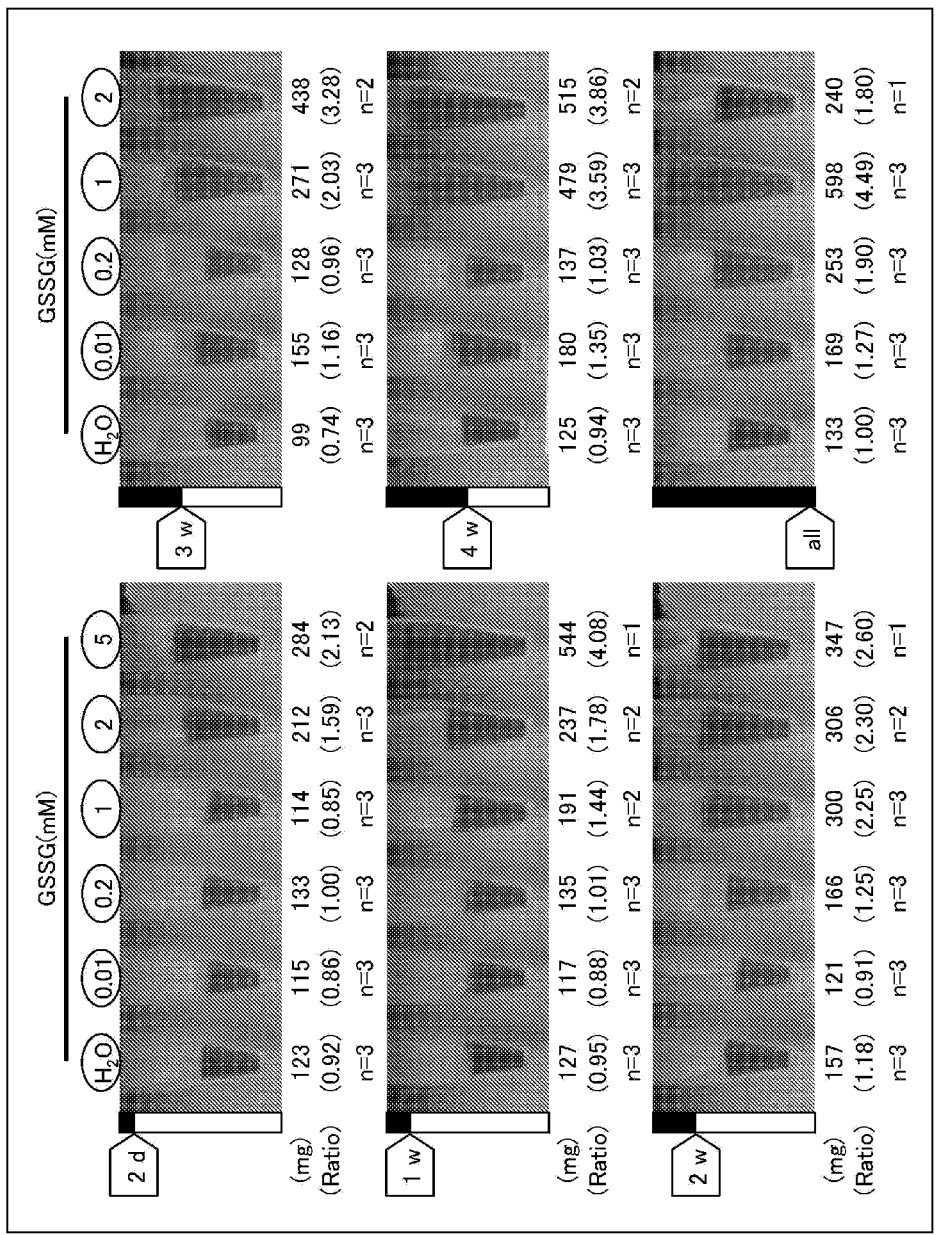
FIG. 10 is a drawing illustrating the result of examination on the influence of a treatment time of oxidized glutathione and treatment concentration of oxidized glutathione on the seed weight of *Arabidopsis*.

In FIG. 10, "Ratio" stands for a ratio of the seed weight of the plant thus cultivated to the seed weight (considered as 1) of a plant cultivated in a tray filled with water containing no GSSG.

Figure 11:
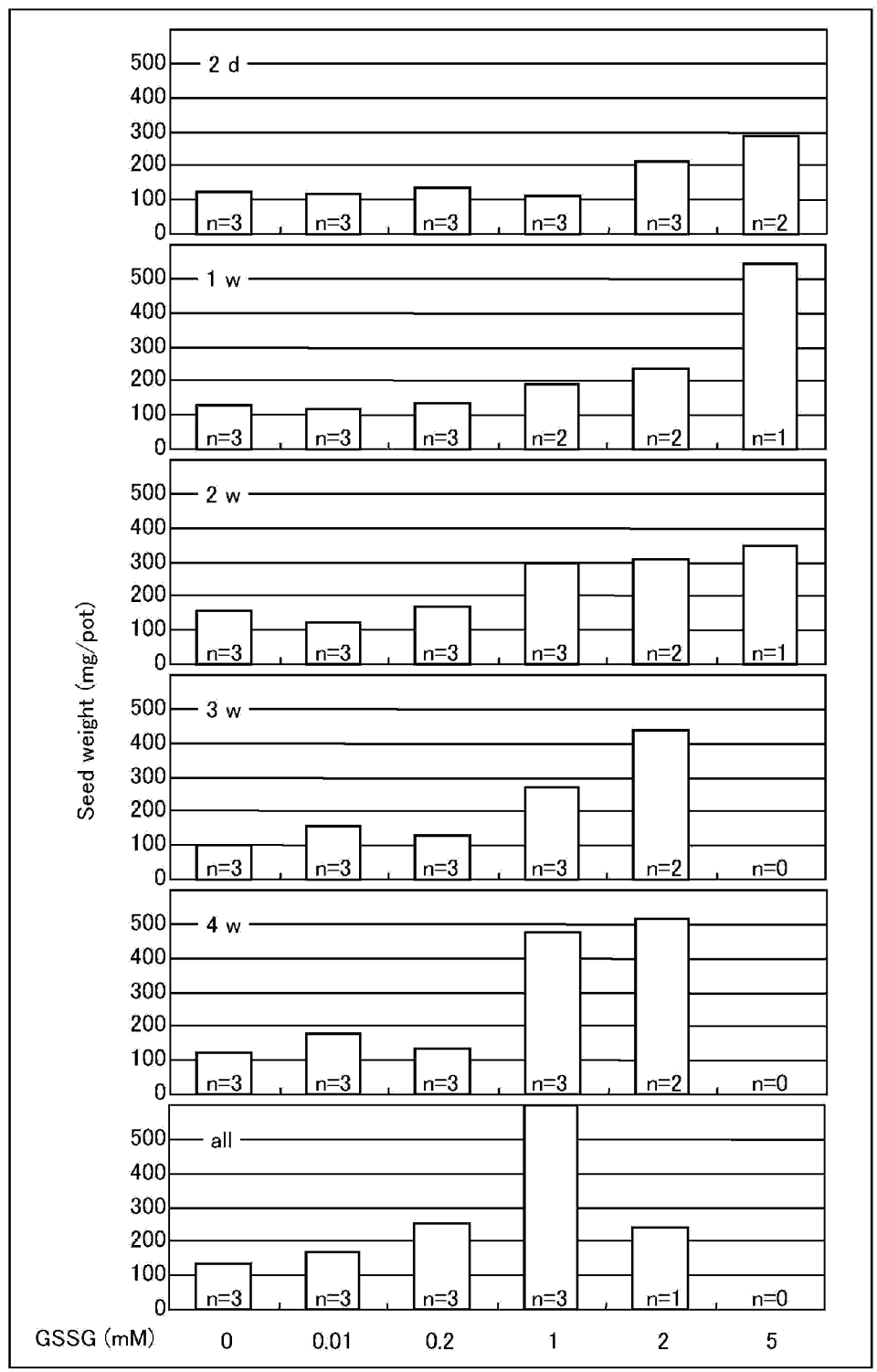
FIG. 11 is a drawing illustrating the result of examination on the influence of a treatment time of oxidized glutathione and treatment concentration of oxidized glutathione on the seed weight of *Arabidopsis*.
Figure 12:
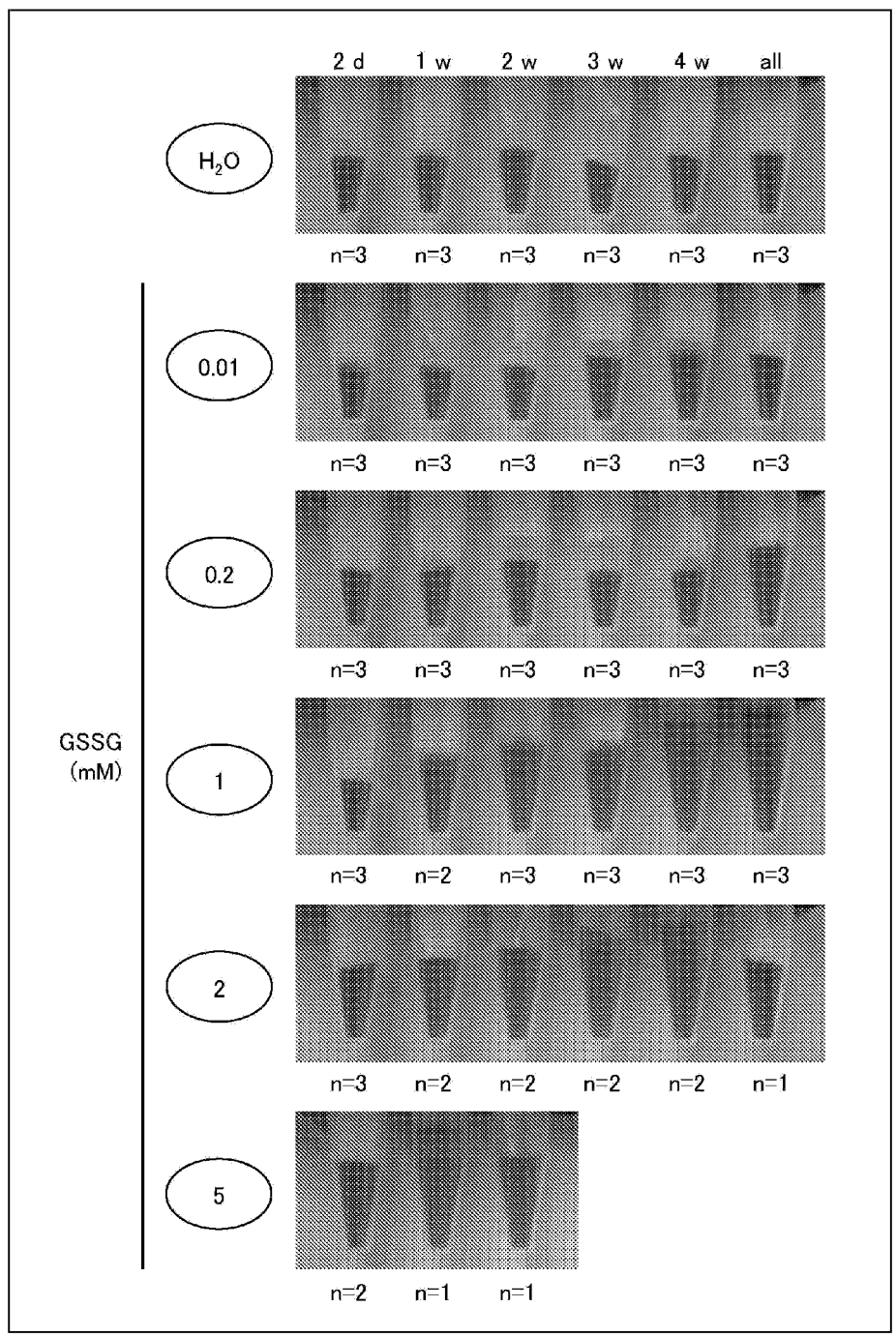
FIG. 12 is a drawing illustrating the result of examination on the influence of a treatment time of oxidized glutathione and treatment concentration of oxidized glutathione on the seed weight of *Arabidopsis*.

As shown in FIGS. 10-12, it was found that susceptibility of Arabidopsis to GSSG varied depending on the amount of GSSG (concentration of GSSG) to be supplied and the time of supplying GSSG. It was found that in a case of supplying GSSG for a long time, GSSG with low concentration is more effective than GSSG with high concentration, and in a case of supplying GSSG for a short time, GSSG with high concentration is more desirable.

<6. Influence 2 of Treatment Condition of Oxidized Glutathione on Seeds of Arabidopsis>

Seeds of Arabidopsis were sown in pods filled with soil immersed in water. The pods were transferred to trays filled with water containing 1 mM-GSSG 2 days after, 1 week after, 2 weeks after, 3 weeks after, 4 weeks after, 5 weeks after, 6 weeks after, or 7 weeks after the sowing. Further, there was prepared a pod that kept in a tray filled with water containing no GSSG, without being transferred into water containing 1 mM-GSSG.

Arabidopsis was cultivated under the same conditions as those described in <1. Influence of oxidized glutathione on growth of Arabidopsis> except for the above condition.

The seed weight per one pod, obtained from Arabidopsis thus cultivated (three plants in each pod), was measured.

Figure 13:
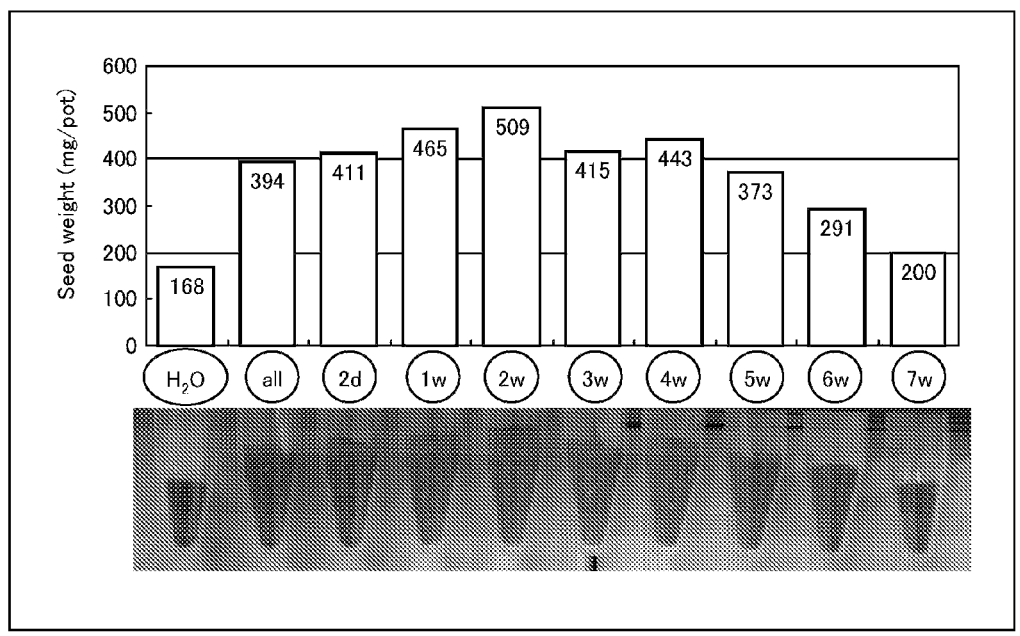
FIG. 13 is a drawing illustrating the result of examination on the influence of a treatment time of oxidized glutathione on the seed weight of *Arabidopsis*.

The result of the measurement showed that as shown in FIG. 13, even when concentration of GSSG to be supplied was the same among the pods, there existed a great difference in the amount of obtained seeds depending on the time of treating the plants with GSSG, indicating that there was a time most suitable for supplying GSSG. On the other hand, regardless of the time of treating the plants with GSSG, the treatment with GSSG allowed obtaining more seed weight than the case of no treatment with the GSSG.

<7. Influence 3 of Treatment Condition of Oxidized Glutathione on Seeds of Arabidopsis>

Seeds of Arabidopsis were sown in pods filled with soil immersed in water. The pods were transferred to trays filled with water containing 1 mM-GSSG and cultivated there only for one week that is the first week (0th-7th day), the second week (8th-14th day), the third week (15th-21st day), the fourth week (22nd-28th day), the fifth week (29th-35th day), the sixth week (36th-42nd day), and the seventh week (43rd-49th day) after the sowing. That is, Arabidopsis was treated with 1 mM-GSSG only for one week in a specific growth period.

There were prepared a pod that was kept in a tray filled with water containing no GSSG and that was not transferred into water containing 1 mM-GSSG consistently from the sowing and a pod that was kept in a tray filled with water containing 1 mM-GSSG consistently from the sowing.

Arabidopsis was cultivated under the same conditions as those described in <1. Influence of oxidized glutathione on growth of Arabidopsis> except for the above condition.

The seed weight per one pod, obtained from Arabidopsis thus cultivated (three plants in each pod), was measured.

Figure 14:
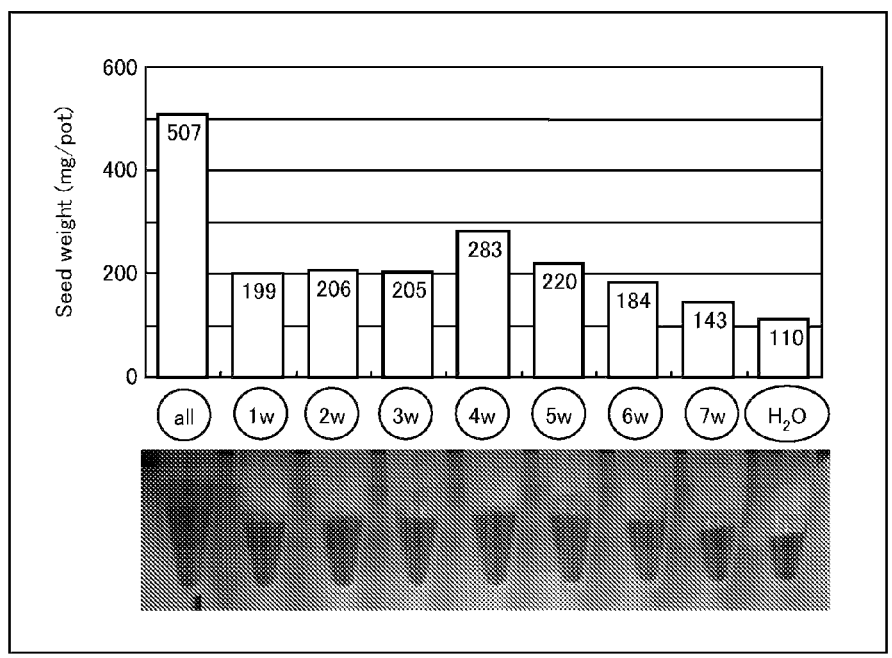
FIG. 14 is a drawing illustrating the result of examination on the influence of a treatment time of oxidized glutathione on the seed weight of *Arabidopsis*.

The result of the measurement showed that as shown in FIG. 14, application of GSSG to Arabidopsis only for one week in a specific growth period significantly increased the seed weight compared with the seed weight of Arabidopsis having not been treated with GSSG, although the effect yielded by applying GSSG to Arabidopsis only for one week in a specific growth period was smaller than the effect yielded by continuously applying GSSG to Arabidopsis.

In this case, too, there existed a great difference in the amount of obtained seeds depending on the time of treating the plants with GSSG. In particular, application of oxidized glutathione 4 weeks after the sowing yielded the maximum seed weight obtained. 4 weeks after the sowing corresponds to around a time of bolting.

<8. Influence 4 of Treatment Condition of Oxidized Glutathione on Seeds of Arabidopsis>

Seeds of Arabidopsis were sown in pods filled with soil immersed in water. The pods were transferred to trays filled with water containing 1 mM-GSSG and cultivated there only for two weeks that are the first and second weeks (0th-14th day), the second and third weeks (8th-21st day), the third and fourth weeks (15th-28th day), the fourth and fifth weeks (22nd-35th day), the fifth and sixth weeks (29th-42nd day), or the sixth and seventh weeks (36th-49th day) after the sowing. That is, Arabidopsis were treated with 1 mM-GSSG only for two weeks in a specific growth period.

There were prepared a pod that was kept in a tray filled with water containing no GSSG and that was not transferred into water containing 1 mM-GSSG consistently from the sowing and a pod that was kept in a tray filled with water containing 1 mM-GSSG consistently from the sowing.

Arabidopsis was cultivated under the same conditions as those described in <1. Influence of oxidized glutathione on growth of Arabidopsis> except for the above condition.

The seed weight per one pod, obtained from Arabidopsis thus cultivated (three plants in each pod), was measured.

Figure 15:
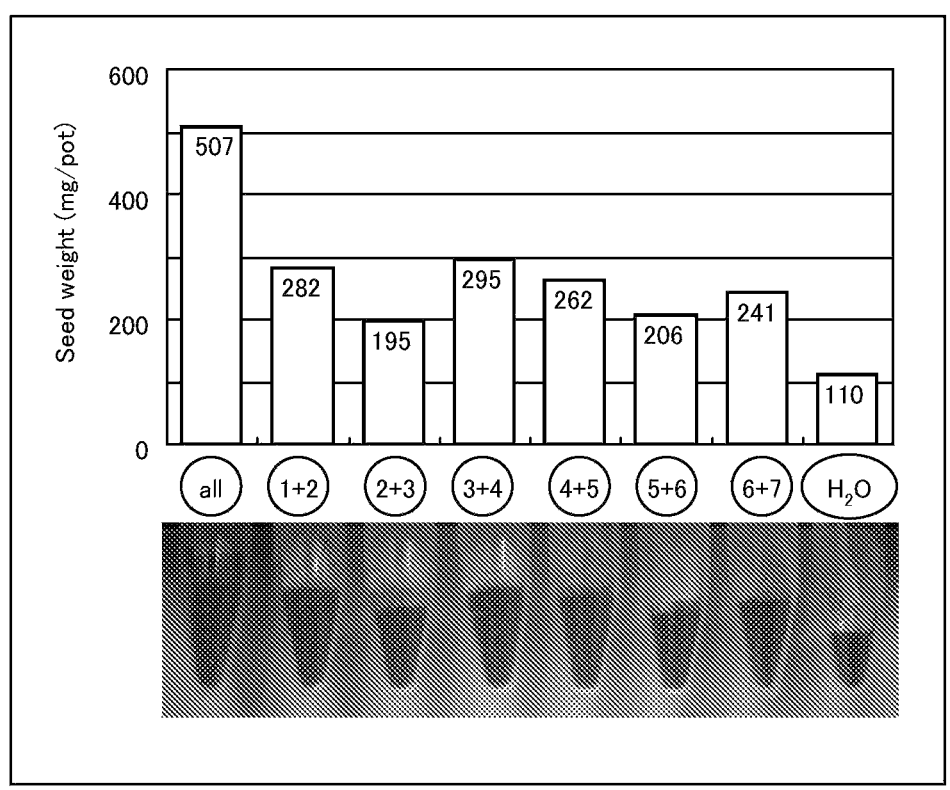
FIG. 15 is a drawing illustrating the result of examination on the influence of a treatment time of oxidized glutathione on the seed weight of *Arabidopsis*.

The result of the measurement showed that as shown in FIG. 15, application of oxidized glutathione to Arabidopsis only for two weeks in a specific growth period significantly increased the seed weight compared with the seed weight of Arabidopsis having not been treated with GSSG, although the effect yielded by applying oxidized glutathione to Arabidopsis only for two weeks in a specific growth period was smaller than the effect yielded by continuously applying oxidized glutathione to Arabidopsis.

In this case, too, there existed a great difference in the amount of obtained seeds depending on the time of treating the plants with GSSG.

<9. Influence 5 of Treatment Condition of Oxidized Glutathione on Seeds of Arabidopsis>

Seeds of Arabidopsis were sown in pods filled with soil immersed in water. The pods were transferred to trays filled with water containing 0.2 mM-GSSG or 1 mM-GSSG and cultivated there only for two weeks that were the first and second weeks (0th-14th day), the third and fourth weeks (15th-28th day), the fifth and sixth weeks (29th-42nd day), or the seventh and eighth weeks (43rd-56th day) after the sowing. That is, Arabidopsis were treated with 0.2 mM-GSSG or 1 mM-GSSG only for two weeks in a specific growth period.

There were prepared a pod that was kept in a tray filled with water containing no GSSG and that was not transferred into water containing 0.2 mM-GSSG or 1 mM-GSSG consistently from the sowing and a pod that was kept in a tray filled with water containing 0.2 mM-GSSG or 1 mM-GSSG consistently from the sowing.

Arabidopsis was cultivated under the same conditions as those described in <1. Influence of oxidized glutathione on growth of Arabidopsis> except for the above condition.

The seed weight, dry weight, and harvest index of *Arabidopsis* thus cultivated (three plants in each pod) were measured and an average of three pods was calculated.

Figure 16:
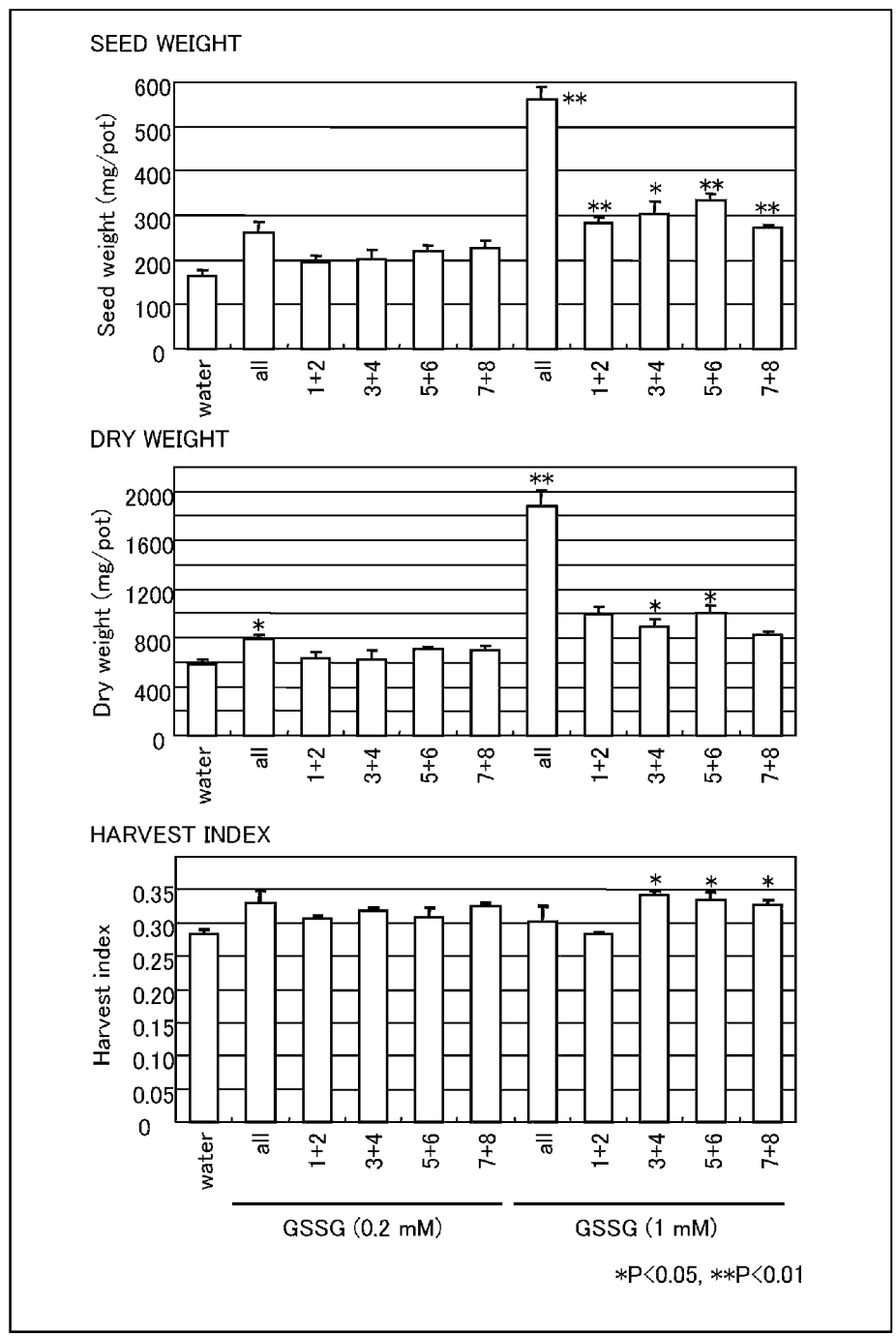
FIG. 16 is a drawing illustrating the result of examination on the influence of a treatment time of oxidized glutathione and treatment concentration of oxidized glutathione on the seed weight, the dry weight, and the harvest index of *Arabidopsis*.

As shown in FIG. 16, the result of the calculation showed that when *Arabidopsis* was treated with 0.2 mM-GSSG, the dry weight increased little compared with a case where *Arabidopsis* was not treated with GSSG, while the seed weight increased, which increased harvest index.

On the other hand, when *Arabidopsis* was treated with 1 mM-GSSG, the seed weight, dry weight, and harvest index evidently increased compared with a case where *Arabidopsis* was not treated with GSSG, except for harvest index in a case where *Arabidopsis* was treated with GSSG 1 or 2 weeks after the sowing.

In FIG. 16, asterisk indicates a great difference between a normal cultivation (water) and a GSSG treatment in the t-test (*$P<0.05$, **$<0.01$).

As described above, the results of <5. Influence of treatment condition of oxidized glutathione on seeds of *Arabidopsis* 1>—<9. Influence of treatment condition of oxidized glutathione on seeds of *Arabidopsis* 5> showed that susceptibility of *Arabidopsis* to oxidized glutathione was different depending on the growth time of *Arabidopsis*. To be specific, in a case where *Arabidopsis* was treated with oxidized glutathione for 1 or 2 weeks, when *Arabidopsis* was treated at 4 weeks to 5 weeks after the sowing, the yield of seeds increased effectively. Under the present growth condition, the time of around 2 weeks after the sowing corresponds to the time of transition from vegetative to reproductive development, and the time of 4 to 5 weeks after the sowing corresponds to around the time of bolting of *Arabidopsis*. That is, it was found that treatment of *Arabidopsis* with oxidized glutathione at a time ranging from the time of transition from vegetative to reproductive development to around the time of bolting allows effectively increasing the yield of seeds.

<10. Influence of Oxidized Glutathione on Growth of Rose (Breed; Patiohit Alicante)>

Rose (breed; Patiohit alicante) was fertilized with 50 mL of 0.5 mM-GSSG solution two times a week for four months and then pruned completely and cultivated. In addition to GSSG, the rose was additionally fertilized with 2 g of S604 per 2 weeks.

Figure 17:
FIG. 17 is a drawing illustrating the result of examination on the influence of oxidized glutathione on growth of a rose (breed; Patiohit alicante).

Consequently, as shown in FIG. 17, it was found that the plant treated with GSSG (plant positioned in the left-side tray in the drawing) exhibited significant promotion of growth of new floral buds compared with the plant that was not treated with GSSG (plant positioned in the right-side tray in the drawing).

<11. Influence of Oxidized Glutathione on Growth of Rose (Breed; English Rose)>

Rose (breed; English rose) was fertilized with 50 mL of a 0.5 mM-GSSG solution two times a week for four months and then pruned completely and cultivated. In addition to GSSG, the rose was additionally fertilized with 2 g of S604 every two weeks.

Figure 18:
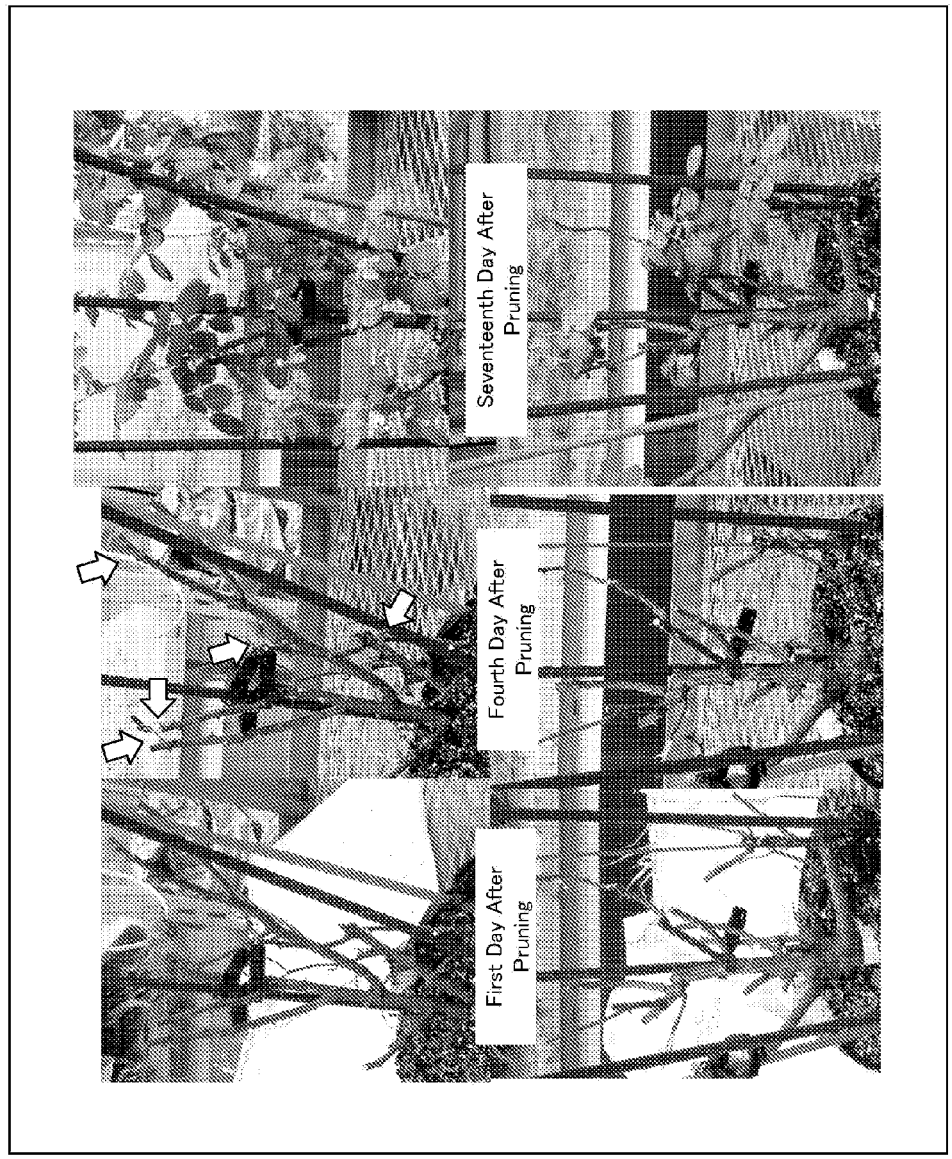
FIG. 18 is a drawing illustrating the result of examination on the influence of oxidized glutathione on growth of a rose (breed; English rose).

Consequently, as shown in FIG. 18, it was found that the plant treated with GSSG (plant positioned in the upper-side in the drawing) exhibited significantly earlier germination and significant promotion of growth of new buds compared with the plant that was not treated with GSSG (plant positioned in the lower-side in the drawing).

<12. Influence of Oxidized Glutathione on Growth of Tsai-hsin (Sakata Seed Co.) 1>

Tsai-hsin was cultivated for two weeks, and then transferred to an agricultural field and grown with or without the treatment with GSSG. Tsai-hsin was fertilized with a nitrogen fertilizer that was KUMIAI RIN RYUANKARI S604 in a ratio of 20 kgN per 10 are, and was additionally fertilized with 5 kgN 3 weeks later.

In a GSSG-treated management zone, 0.5 mM- or 5 mM-GSSG solution was sprayed to surfaces of leaves of the plant two times a week in such a manner that 1 L of the GSSG solution was sprayed per 1 zone (3 m$^2$).

Figure 19:
FIG. 19 is a drawing illustrating the result of examination on the influence of oxidized glutathione on growth of tsai-hsin that is a kind of coleseed.

Consequently, as shown in FIG. 19, the plant in the GSSG-treated management zone exhibited significant increase in the amount of growth than the plant in a normal nitrogen management zone (not treated with GSSG).

<13. Influence of Oxidized Glutathione on Growth and Yield of Seeds of Soybean 2>

Figure 20:
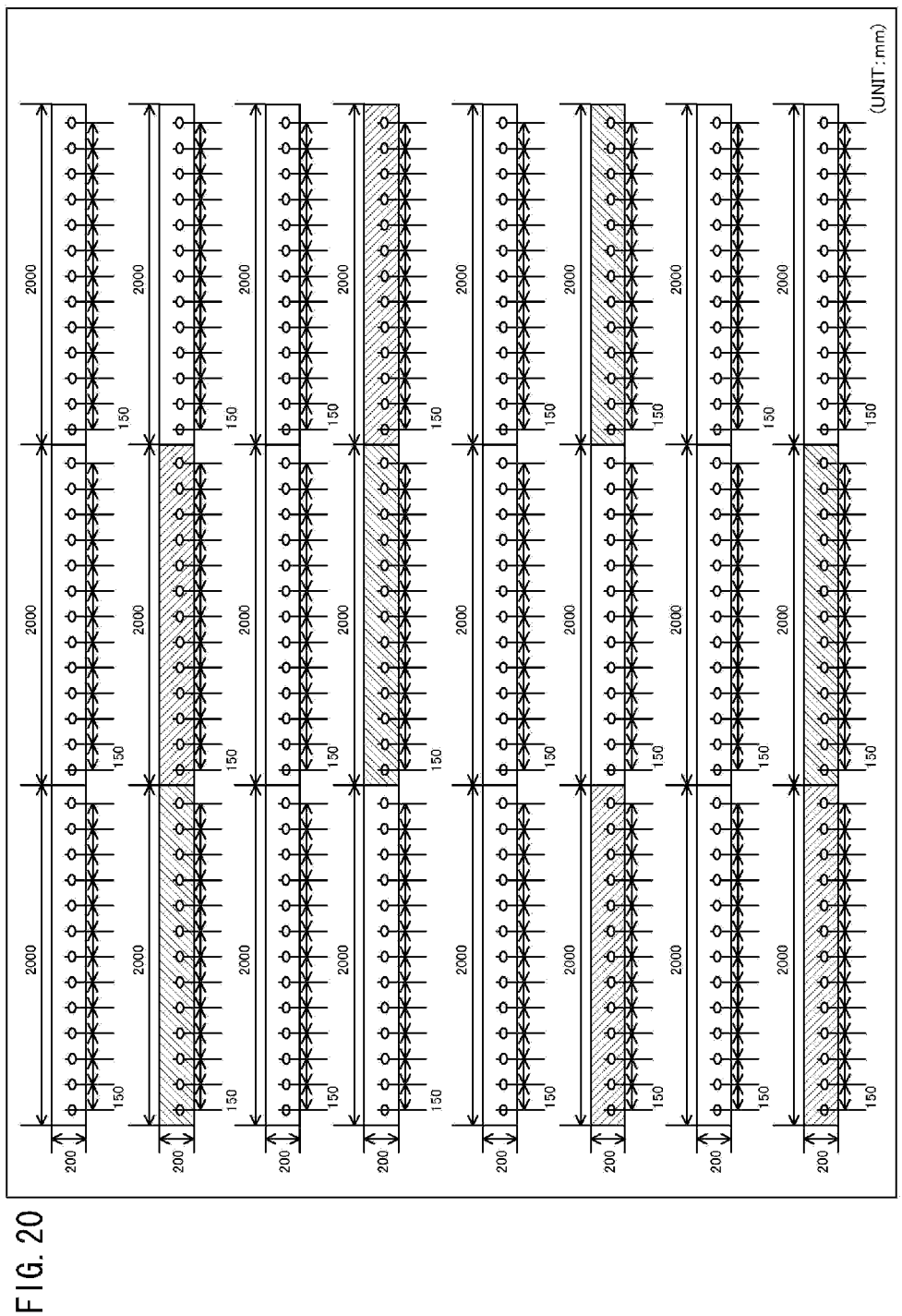
FIG. 20 is a drawing illustrating positions of individual soybeans in an agricultural field test in which the influence of oxidized glutathione on growth of soybean is examined.

Soybean (breed: Tsurumusume) and soybean (breed; Toyomusume) were cultivated for two weeks, and then transferred to an agricultural field in such a manner as to be positioned as shown in FIG. 20, and grown with or without the treatment with GSSG. The soybean was fertilized with a nitrogen fertilizer that was KUMIAI RIN RYUANKARI S604 in a ratio of 20 kgN per 10 are, and was additionally fertilized with 5 kgN 3 weeks later.

Figure 21:
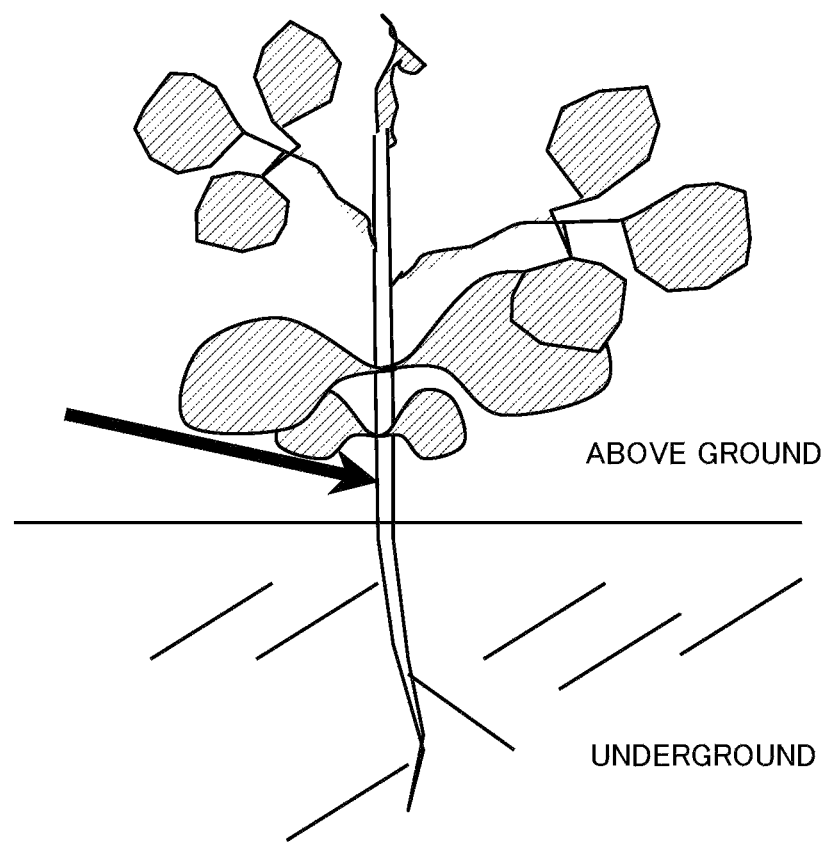
FIG. 21 is a drawing illustrating how to supply oxidized glutathione in the agricultural field test in which the influence of oxidized glutathione on growth of soybean is examined.

Further, in a GSSG-treated management zone, a 0.5 mM-GSSG solution was given to the base of a stem (see the arrow in FIG. 21) in the amount of 50 mL per one individual two times a week in such a manner that the solution flowed along the stem.

In a case where it was likely to rain, the GSSG solution was supplied to the plant after the rain. Similarly, in a case of watering, the GSSG solution was supplied to the plant after the watering. When the harvest time of the plant of the control (i.e. normal nitrogen management zone) was coming, supply of the GSSG solution to the plant in the GSSG-treated management zone was stopped.

The seed weight, the amount of biomass, and the harvest index of the plant thus obtained in the GSSG-treated management zone, each relative to that of the plant in the normal nitrogen management zone, were measured.

Figure 22:
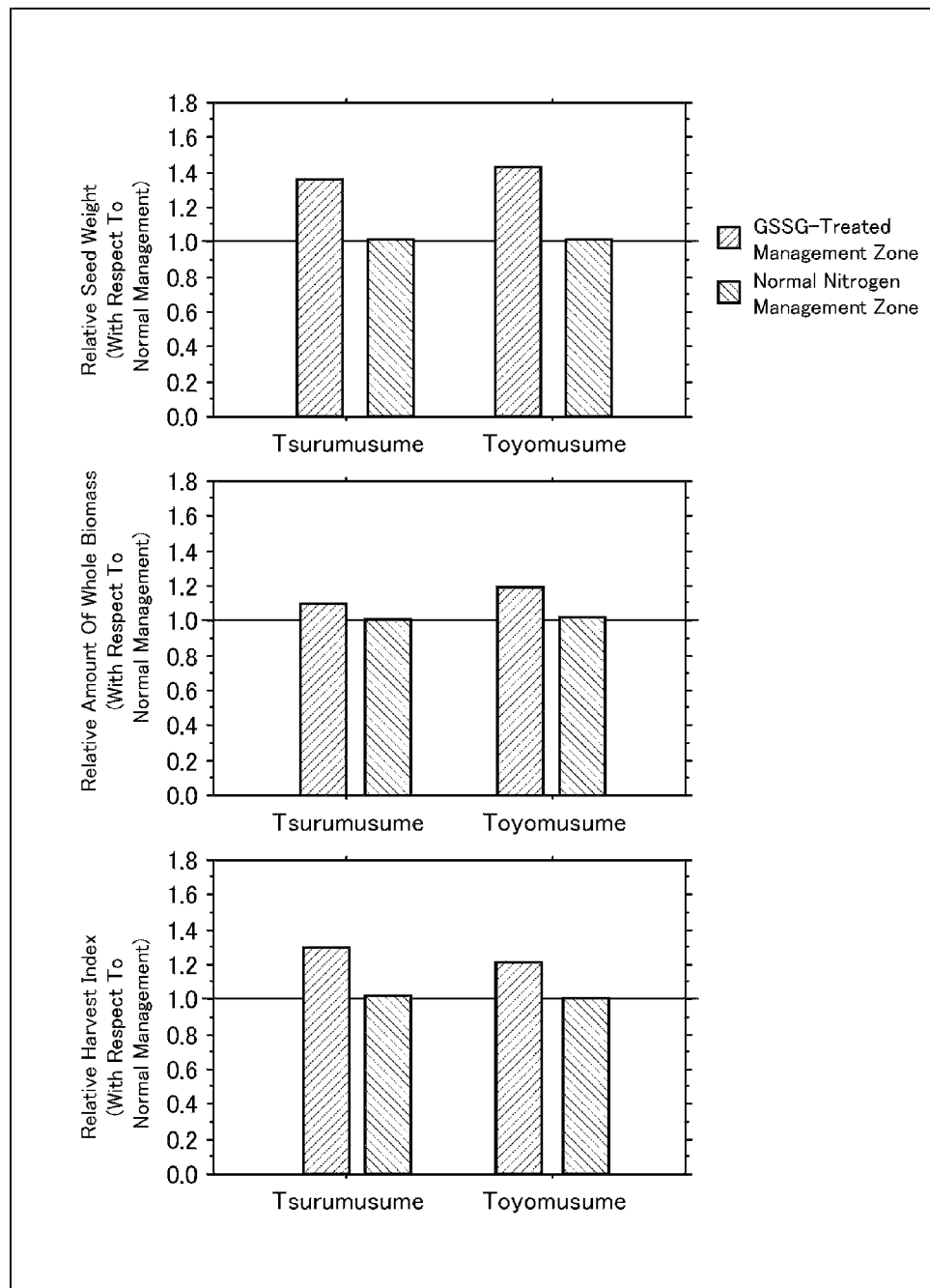
FIG. 22 is a drawing illustrating the results of examinations on the weight of seeds, the whole amount of biomass, and the harvest index in the agricultural field test in which the influence of oxidized glutathione on growth of soybean is examined

Consequently, as shown in FIG. 22, with respect to each breed, the plant in the GSSG-treated management zone exhibited a higher seed weight, a higher amount of biomass, and a higher harvest index than those of the plant in the normal nitrogen management zone.

<14. Effect 1 of Oxidized Glutathione on Productivity of Corn>

Figure 25:
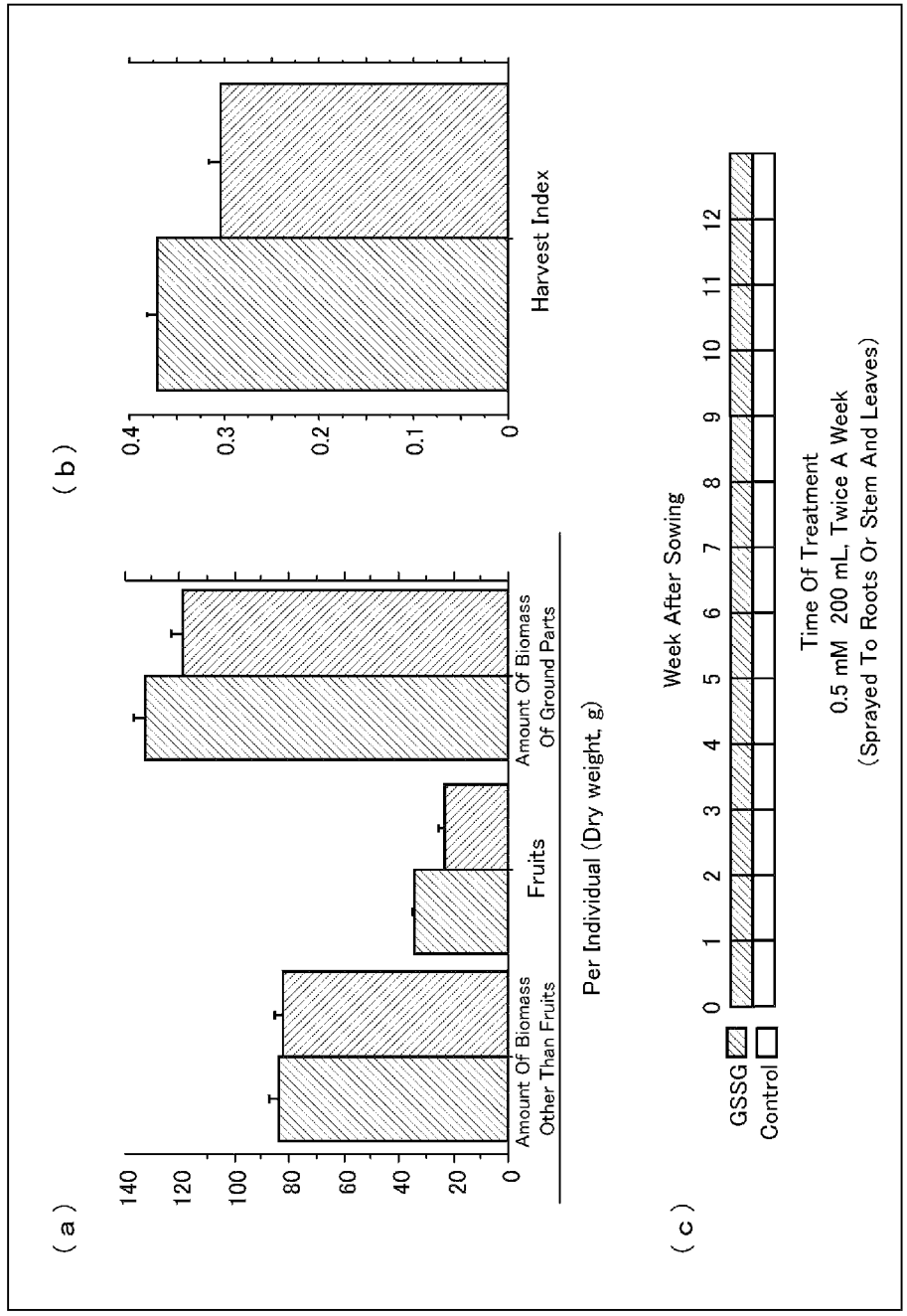
FIG. 25 is a drawing illustrating the results of examinations on the influence of oxidized glutathione on the amount of biomass and the harvest index of fruits, ground parts, and portions other than the fruits of individual corns.

Sweet corn (Canberra 90, TAKII & CO., LTD.) was sown, and then transferred to a hydroponics pot (1/2000 are) filled with a culture soil (6 L of vermiculite as the lower layer, 3 L of The Kureha Ikubyou Baido soil as the middle layer, and 3 L of vermiculite as the upper layer) two weeks later and additionally fertilized with 3 g of KUMIAI RIN RYUAN-KARI S604 four weeks later and six weeks later. Further, the GSSG-treated plant was given 200 mL of 0.5 mM-GSSG two times a week for 12 weeks after germination at its root. As for the time of the treatment with GSSG, see (c) of FIG. 25. The time indicated by the hatched part in (c) of FIG. 25 was the time of the treatment with GSSG.

Figure 23:
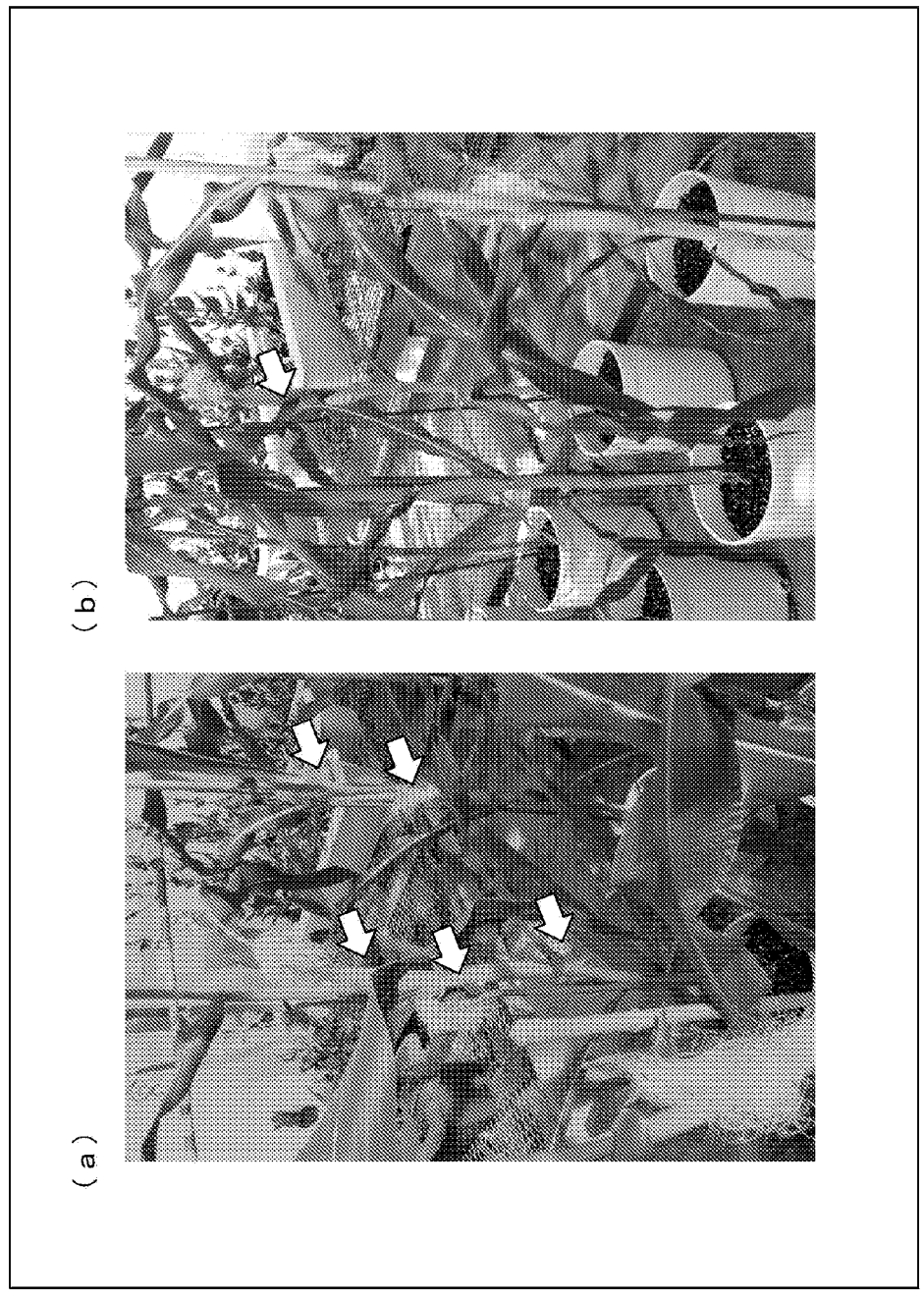
FIG. 23 is a drawing illustrating the results of examination on the influence of oxidized glutathione on formation of floral buds of corn.

Consequently, as shown in FIG. 23, the plant treated with GSSG (left-side (a) in FIG. 23) exhibited promotion of formation of floral buds compared with the plant that was not treated with GSSG (right-side (b) in FIG. 23).

Figure 24:
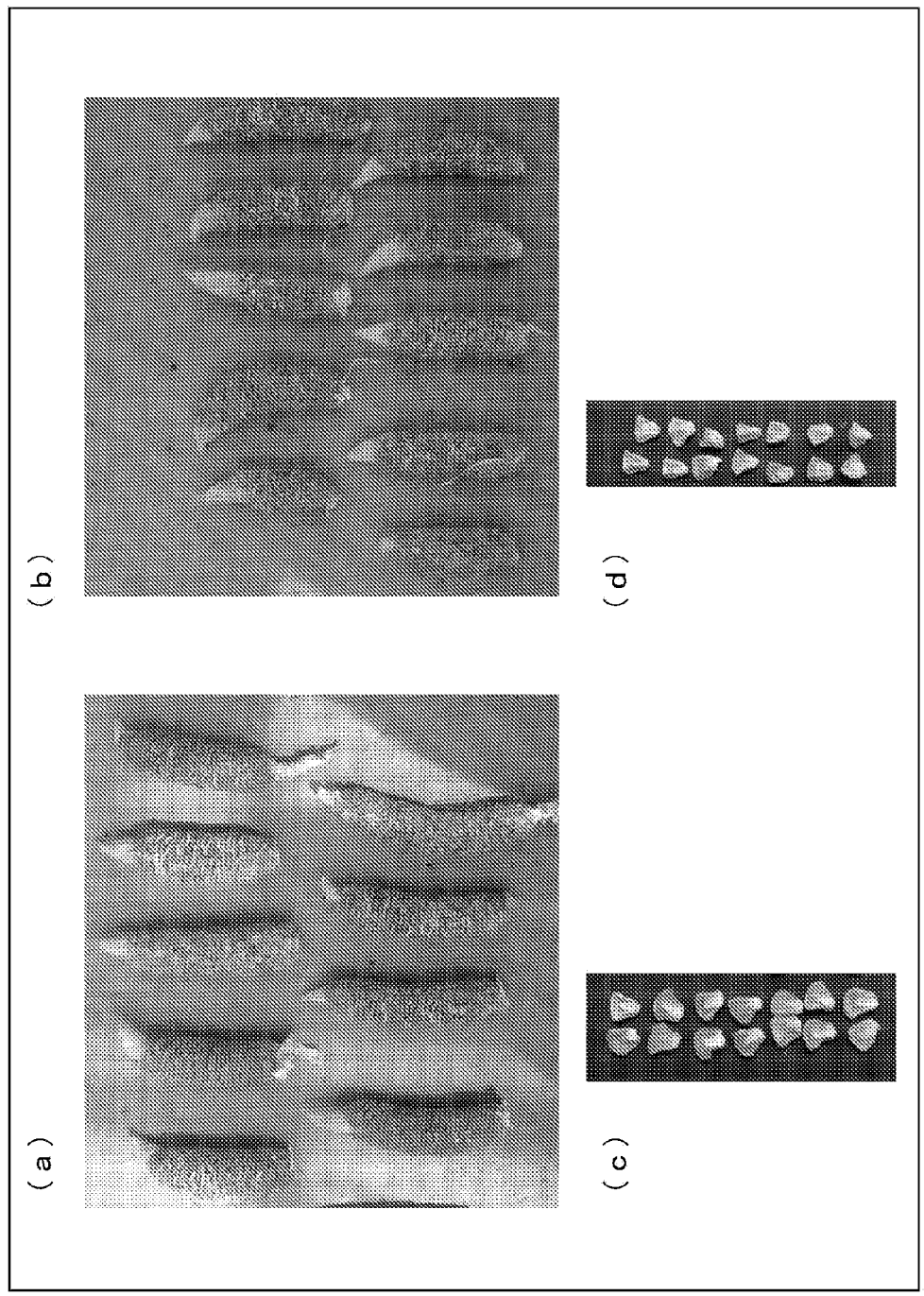
FIG. 24 is a drawing illustrating the results of examination on the influence of oxidized glutathione on the crop yields of corn.

Further, as shown in FIG. 24, fruits of the plant treated with GSSG (upper-left panel (a) in FIG. 24) were larger than pistils of the plant that was not treated with GSSG (upper-right panel (b) in FIG. 24) and had more number of edible seeds than the plant that was not treated with GSSG.

Further, seeds of the plant treated with GSSG (lower-left panel (c) in FIG. 24) were larger than seeds of the plant that was not treated with GSSG (lower-right panel (d) in FIG. 24).

This clearly shows that treating corn with GSSG increases the crop yields of the corn.

Subsequently, the amounts of biomass of fruits, ground parts, and portions other than the fruits of the plant treated with GSSG and the plant that was not treated with GSSG were measured. As shown in (a) of FIG. 25, the result of the measurement showed that there was no great difference in the amount of biomass of the portions other than the fruits between the plant treated with GSSG and the plant that was not treated with GSSG, whereas the amounts of biomass of the fruits and ground parts of the plant treated with GSSG were significantly high.

In view of the above, harvest index was calculated. The result of the calculation showed that as shown in (b) of FIG. 25, the plant treated with GSSG exhibited significantly high harvest index than the plant that was not treated with GSSG.

<15. Effect 2 of Oxidized Glutathione on Productivity of Corn>

Effect of the time of the treatment with oxidized glutathione on productivity of corn was examined.

Sweet corn (Canberra 90, TAKII & CO., LTD.) was sown, and then transferred to a hydroponics pot (1/2000 are) filled with a culture soil (6 L of vermiculite as the lower layer, 3 L of The Kureha Ikubyou Baido soil as the middle layer, and 3 L of vermiculite as the upper layer) two weeks later and additionally fertilized with 3 g of KUMIAI RIN RYUAN-KARI S604 four weeks later and six weeks later.

Further, the GSSG-treated plant was given 50 mL of 0.2 mM-GSSG solution four times in 2 weeks (two times a week) after 2 weeks, 4 weeks, or 6 weeks had elapsed from the sowing. Further, there were prepared a management zone to which 0.2 mM-GSSG was given 22 times in total for 11 weeks after 2 weeks had elapsed from the sowing and a management zone to which 0.2 mM-GSSG was not given. As for the time of the treatment with GSSG, see (c) of FIG. 26. The time indicated by the hatched part in FIG. (c) of 26 was the time of the treatment with GSSG.

The amount of fruits and the amount of biomass of ground parts of each plant were measured and harvest index was calculated.

Figure 26:
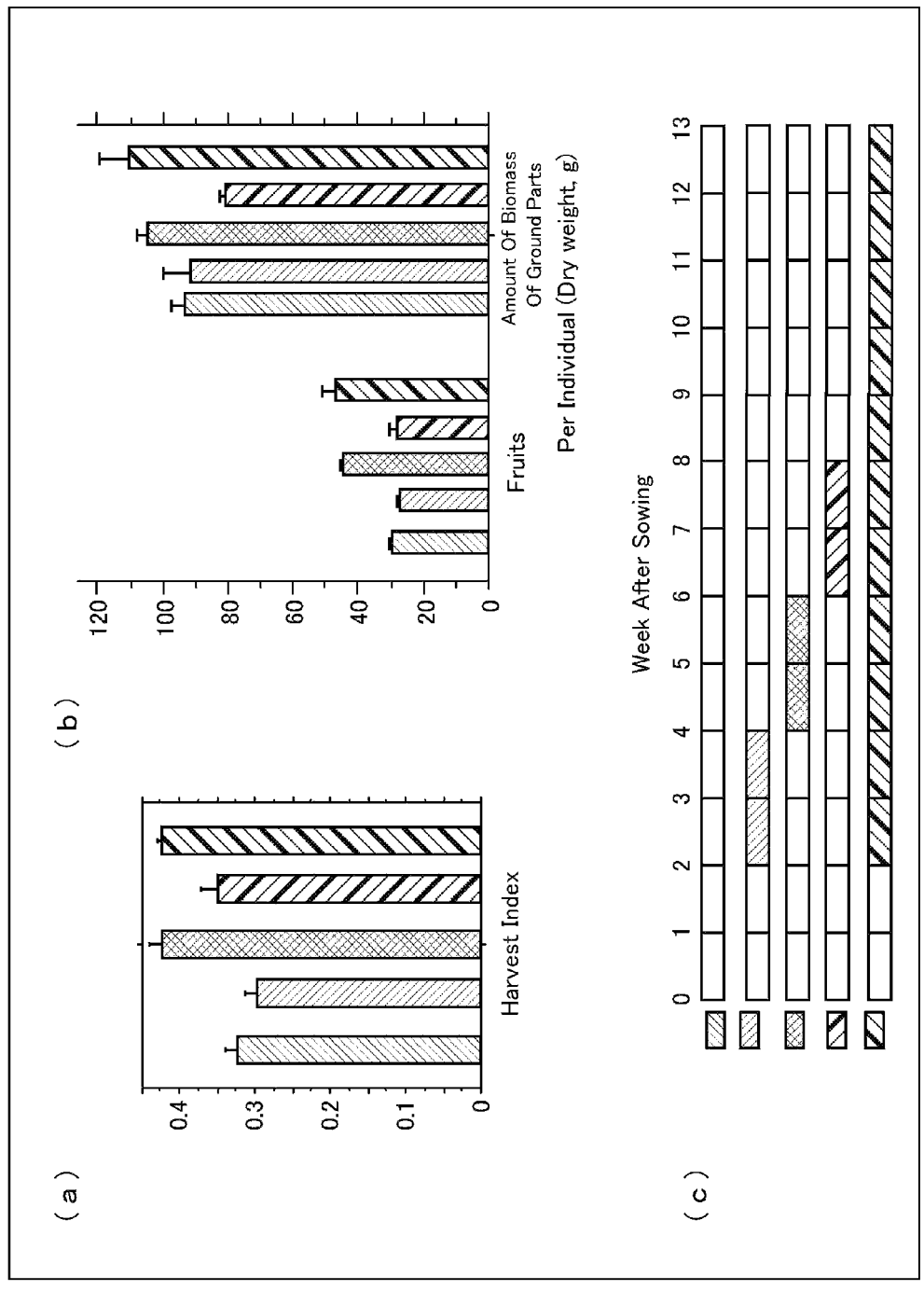
FIG. 26 is a drawing illustrating the results of examinations on the influence of a treatment time of oxidized glutathione on the amount of biomass and the harvest index of fruits, ground parts, and portions other than the fruits of individual corns.

Consequently, as shown in (a) of FIG. 26, the plant treated with GSSG for two weeks after four weeks had elapsed from the sowing and for two weeks after six weeks had elapsed from the sowing and the plant treated with GSSG for eleven weeks after two weeks had elapsed from the sowing exhibited larger harvest index than the plant that was not treated with GSSG. In particular, the plant treated with GSSG for two weeks after four weeks had elapsed from the sowing and the plant treated with GSSG for eleven weeks after two weeks had elapsed from the sowing exhibited a great increase in harvest index.

As shown in (b) of FIG. 26, the plant treated with GSSG for two weeks after four weeks had elapsed from the sowing and the plant treated with GSSG for eleven weeks after two weeks had elapsed from the sowing had a larger amount of fruits and a larger amount of biomass of ground parts per each plant than the plant that was not treated with GSSG. However, the plant treated with GSSG for two weeks after six weeks had elapsed from the sowing had a smaller amount of fruits and a smaller amount of biomass of ground parts per each plant than the plant that was not treated with GSSG.

<16. Effect 3 of Oxidized Glutathione on Productivity of Corn>

Sweet corn was cultivated under the same conditions as those of <15. Effect of oxidized glutathione on productivity of corn 2> except that GSSG was sprayed to a stem and leaves four times in two weeks after six weeks had elapsed from the sowing, the zone where sweet corn was cultivated was considered as a GSSG-treated zone, and GSSG was foliar-sprayed. See the time of treatment with GSSG in (c) of FIG. 27. The time indicated by the hatched part in (c) of FIG. 27 is the time of treatment with GSSG.

The amount of fruits and the amount of biomass of ground parts of the plant thus obtained were measured with respect to each plant and harvest index was calculated.

Figure 27:
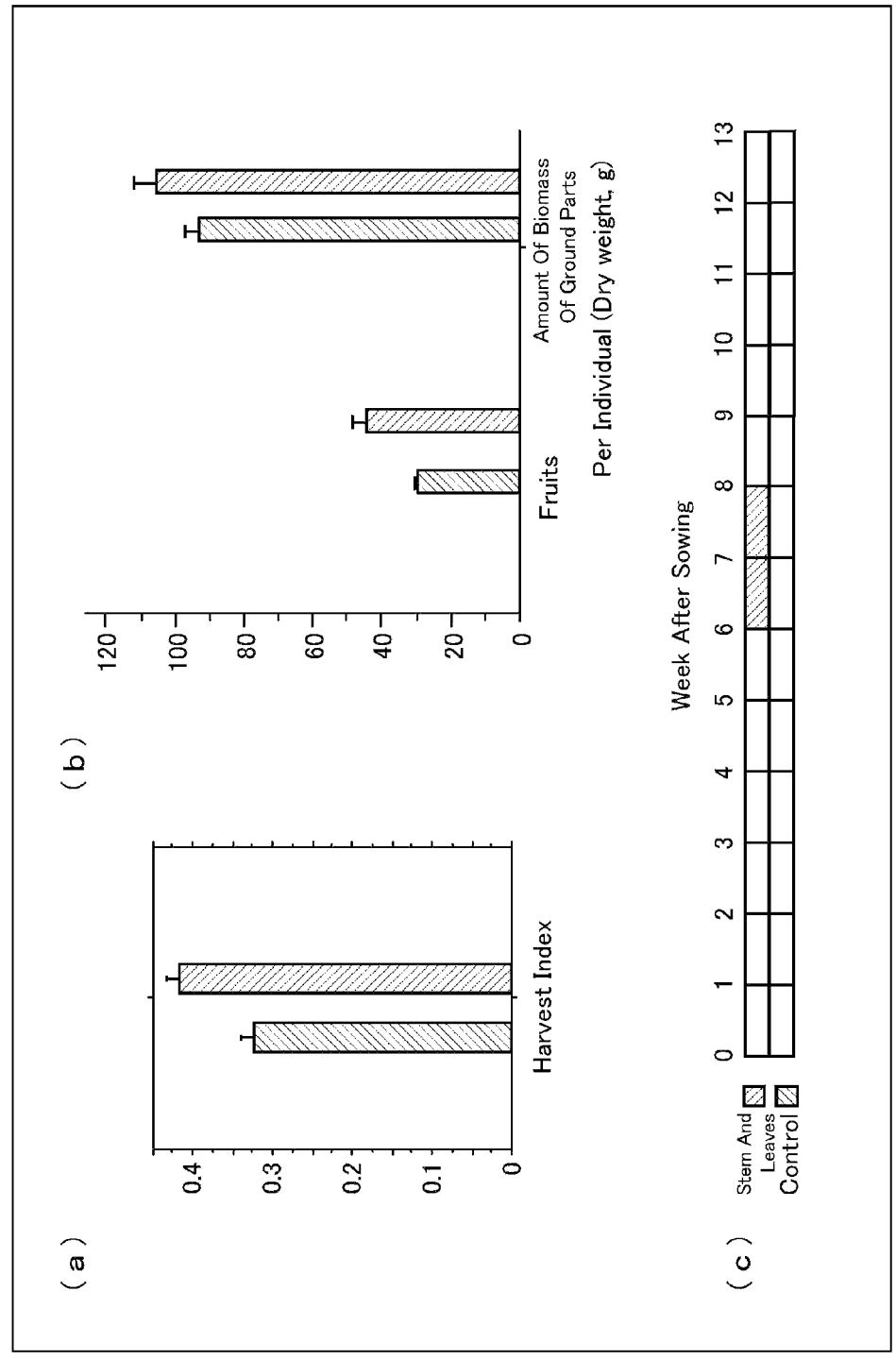
FIG. 27 is a drawing illustrating the results of examinations on the influence of a treatment method of oxidized glutathione on the amount of biomass and the harvest index of fruits, ground parts, and portions other than the fruits of individual corns.

Consequently, as shown in (a) and (b) of FIG. 27, even in a case of spraying GSSG to a stem and leaves, the treatment with GSSG increased the amount of fruits, the amount of biomass of ground parts, and the harvest index of each plant.

<17. Effect 4 of Oxidized Glutathione on Productivity of Corn>

Figure 28:
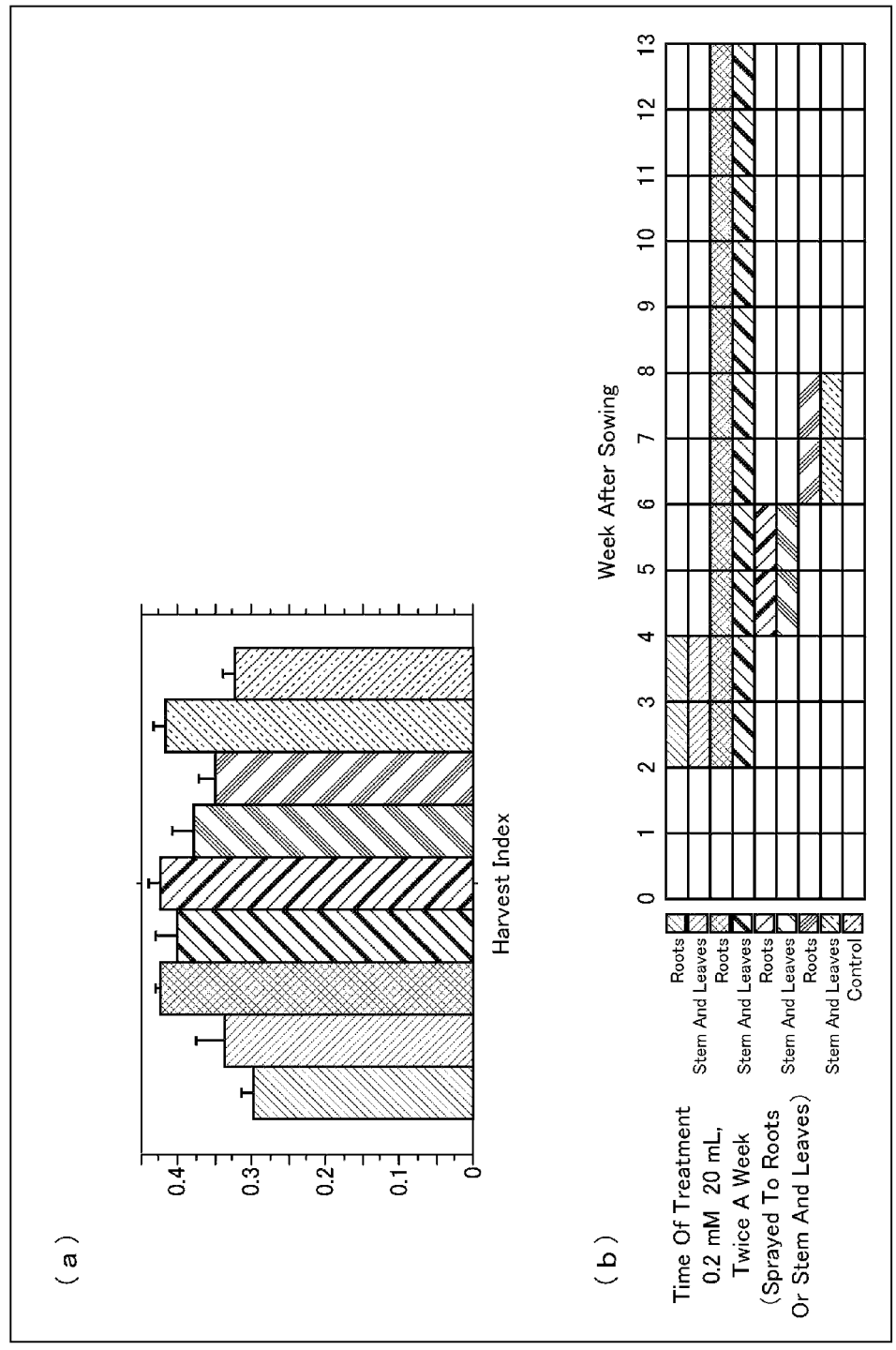
FIG. 28 is a drawing illustrating the results of examinations on the influence of a treatment method of oxidized glutathione and a treatment time of oxidized glutathione on the harvest index of corn.

Sweet corn was cultivated under the same conditions as those of <15. Effect of oxidized glutathione on productivity of corn 2> except that GSSG was supplied to roots in the form of a solution or sprayed to a stem and leaves for two weeks after two weeks had elapsed from the sowing, or for eleven weeks after two weeks had elapsed from the sowing, or for two weeks after four weeks had elapsed from the sowing, or for two weeks after six weeks had elapsed from the sowing, and 20 mL of 0.2 mM-GSSG was supplied each time. See the time of treatment with GSSG in (b) of FIG. 28. The time indicated by the hatched part in (b) of FIG. 28 is the time of treatment with GSSG.

Harvest index of the plant thus obtained was measured. Consequently, as shown in (a) of FIG. 28, harvest index significantly increased under any of the above conditions compared with the case of the plant that was not treated with GSSG.

<18. Effect 5 of Oxidized Glutathione on Productivity of Corn>

Figure 29:
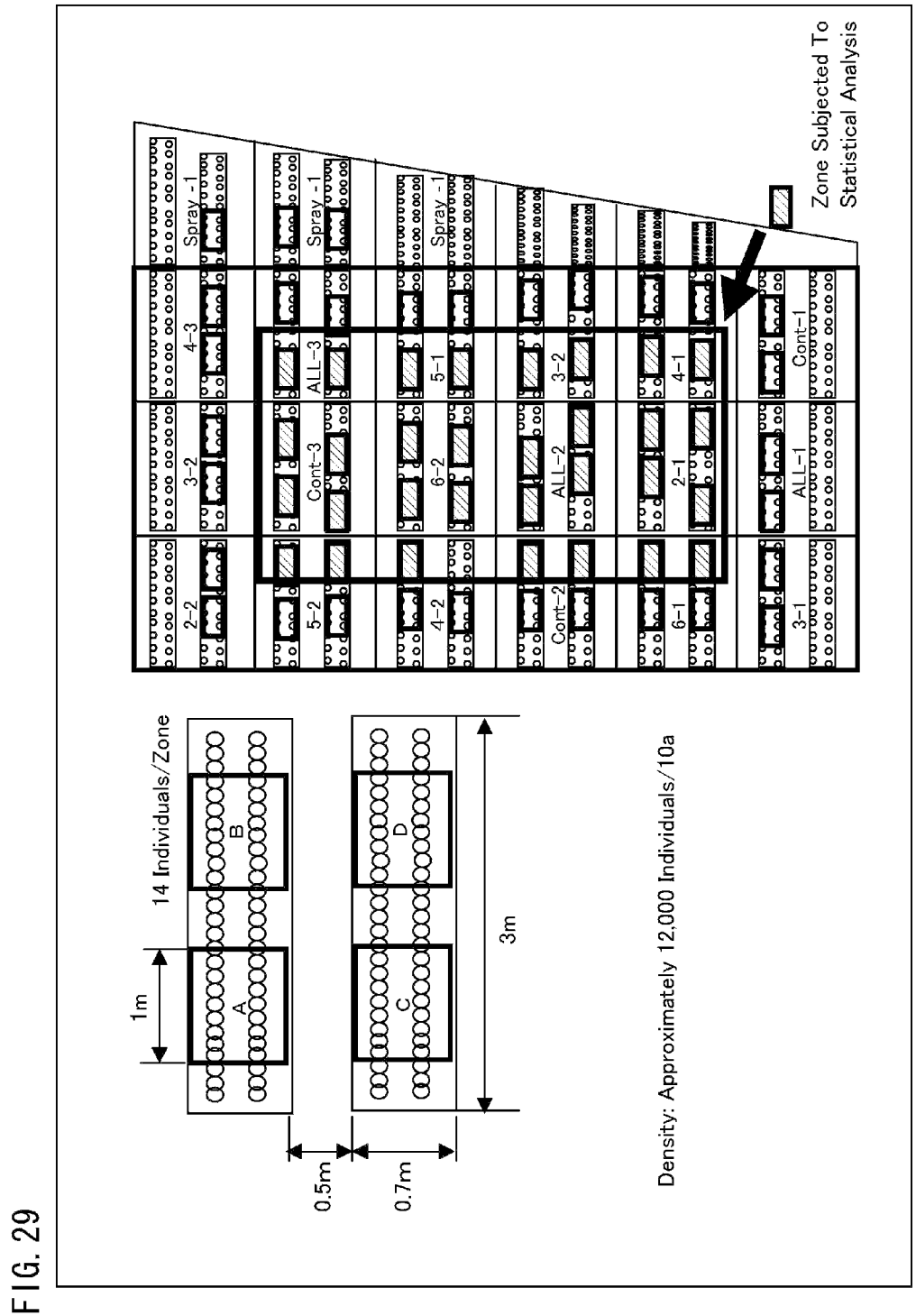
FIG. 29 is a drawing illustrating positions of individual corn in an agricultural field test in which the influence of oxidized glutathione on growth of corn is examined.

Sweet corn was cultivated in an agricultural field in such a manner that the sweet corn was positioned as shown in FIG. 29 (density: approximately 12000 individuals/10a).

There were prepared plants treated with GSSG as follows: plants whose roots were sprayed with GSSG (20 mL of 0.5 mM-GSSG per each time) two times a week for two weeks after two weeks had elapsed from the sowing, for two weeks after three weeks had elapsed from the sowing, for two weeks after four weeks had elapsed from the sowing, for two weeks after five weeks had elapsed from the sowing, for two weeks after six weeks had elapsed from the sowing, and for seven weeks after two weeks had elapsed from the sowing; plants that were not treated with GSSG; and plants whose stem and leaves were sprayed with GSSG (20 mL of 0.5 mM-GSSG per each time with respect to each plant) two times a week for seven weeks after two weeks had elapsed from the sowing. See the time of treatment with GSSG in (b) of FIG. 30. The time indicated by the hatched part in (b) of FIG. 30 is the time of the treatment with GSSG.

The whole amount of biomass per area and the yield of pistils (fruits) per area of plants having grown inside a colony out of the plants thus obtained were measured and harvest index was calculated.

Figure 30:
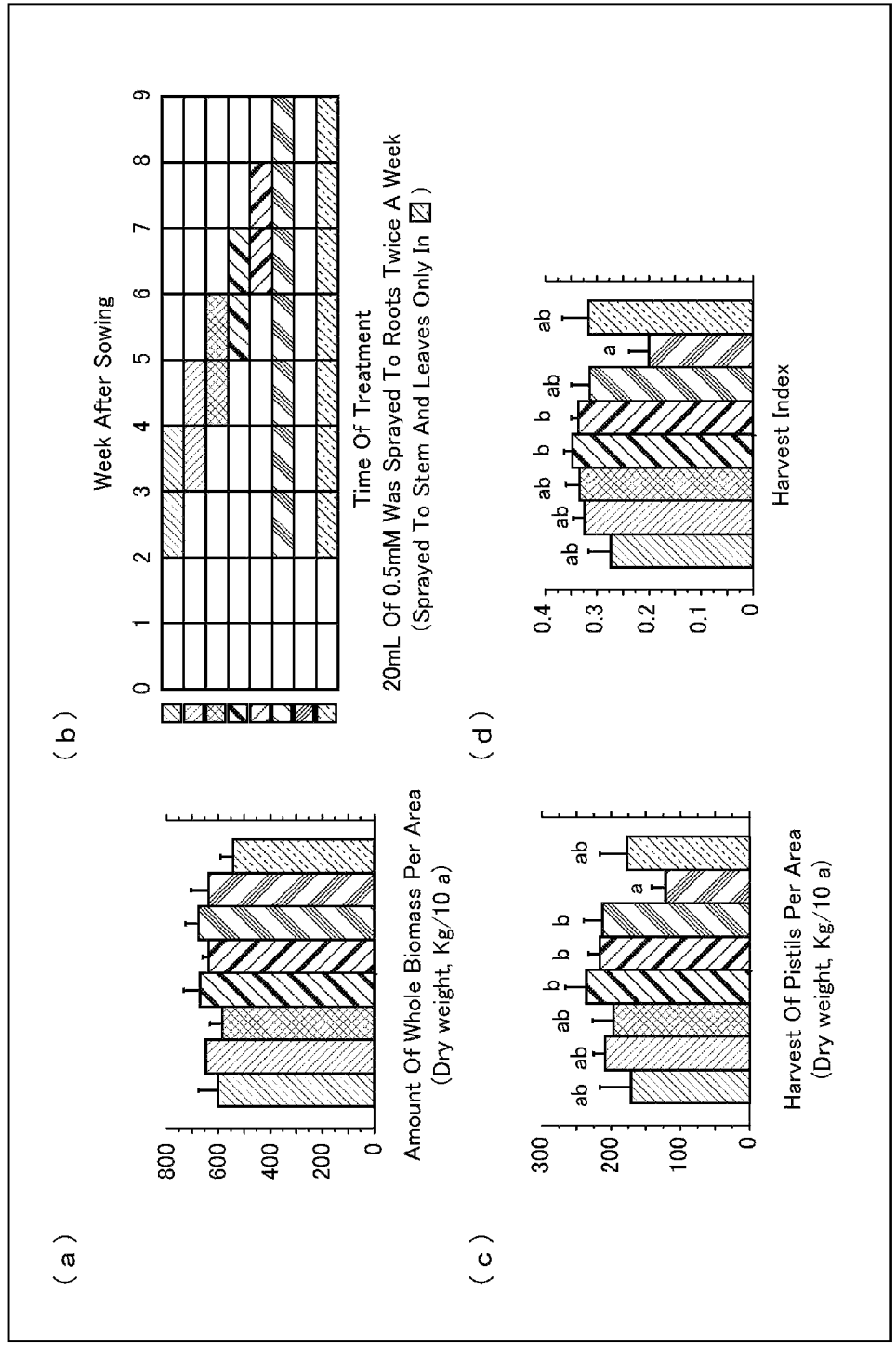
FIG. 30 is a drawing illustrating the results of examinations on the influence of a treatment time of oxidized glutathione on the whole amount of biomass per area, the crop yields of pistils per area, and the harvest index in an agricultural field test in which the influence of oxidized glutathione on growth of corn is examined.

Consequently, as shown in (a), (c), and (d) of FIG. 30, any of the conditions for treatment with GSSG did not exhibit a significant difference in the whole amount of biomass per area from the case of the plants that were not treated with GSSG, but exhibited higher yield of pistils (fruits) and higher harvest index.

Figure 31:
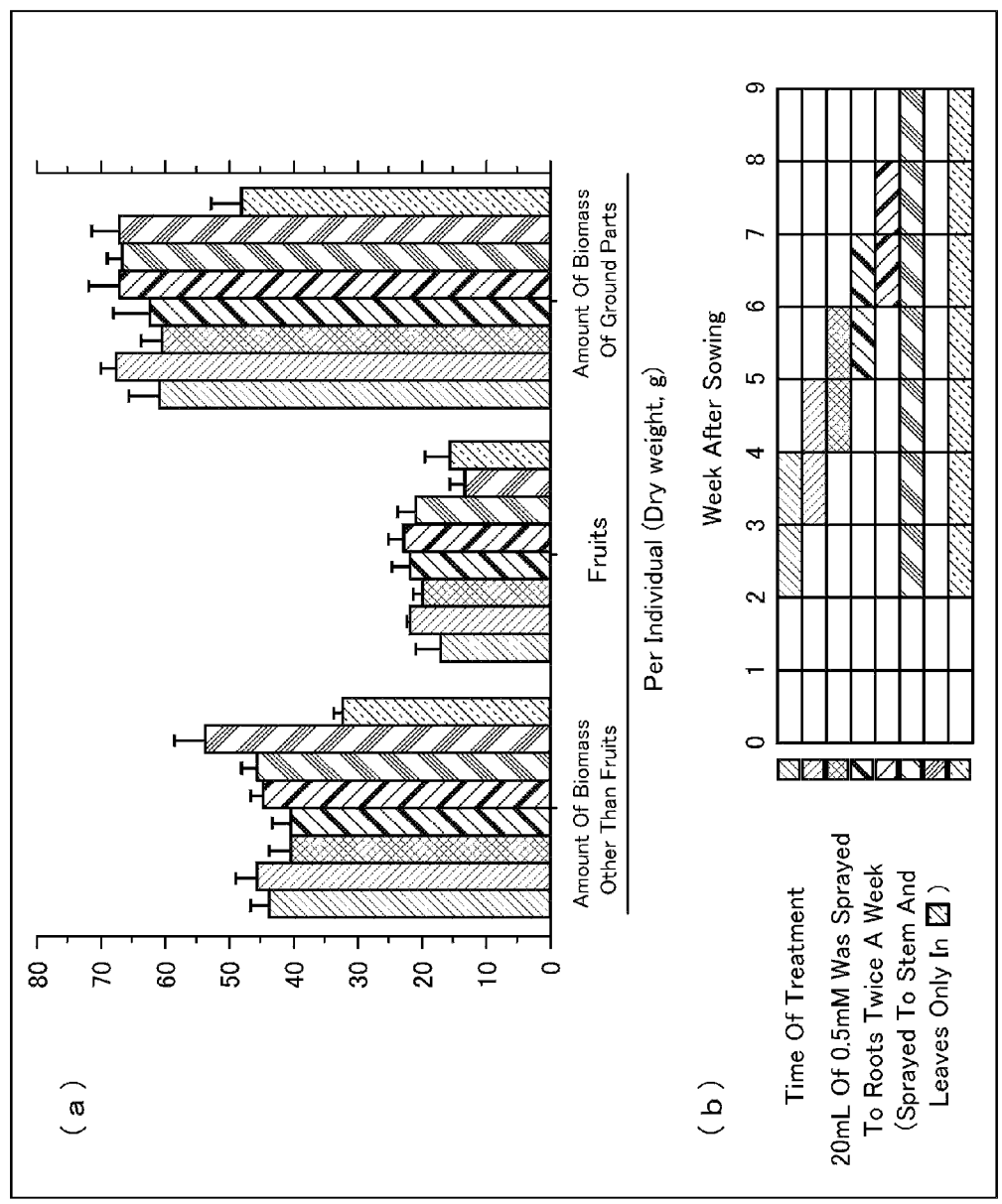
FIG. 31 is a drawing illustrating the results of examinations on the influence of a treatment time of oxidized glutathione on the amounts of biomass of fruits, ground parts, and portions other than the fruits of individual corns in an agricultural field test in which the influence of oxidized glutathione on growth of corn is examined.

Further, the amounts of biomass of fruits, ground parts, and portions other than the fruits of each of the plants were measured. As shown in FIG. 31, the results of the measurement showed that any of the conditions for treatment with GSSG exhibited higher amount of biomass of fruits (i.e. amount of fruits) than the case of the plants that were not treated with GSSG.

However, any of the conditions for treatment with GSSG exhibited a lower amount of biomass of the portions other than fruits than the case of the plants that were not treated with GSSG. Further, any of the conditions for treatment with GSSG exhibited substantially the same or lower amount of biomass of ground parts than the case of the plants that were not treated with GSSG. In particular, the plant whose stem and leaves were sprayed with GSSG for seven weeks after two weeks had elapsed from the sowing exhibited greatly lower amounts of biomass of the portions other than fruits and ground parts than the case of the plants that were not treated with GSSG.

The above results show that oxidized glutathione increases the amount of fruits that were harvests of corn and thus increases harvest index, without increasing the amount of biomass of ground parts.

<19. Effect of Oxidized Glutathione on Productivity of Corn under Nitrogen-deficient Condition>

Sweet corn was sown and cultivated for 84 days (7 weeks) after the sowing without supplying a nitrogen source to the sweet corn. Thereafter, the sweet corn was cultivated with 30 kgN/10a of a nitrogen source. Treatment with GSSG was performed in such a manner that GSSG solutions with 0 mM-, 0.2mM-, 0.5 mM, and 1.0 mM-concentrations were supplied in the amount of 50 mL per one time, two times a week, 8 weeks after the sowing (i.e. after the supply of the nitrogen source began). See the cultivation conditions in (c) of FIG. 33.

Figure 32:
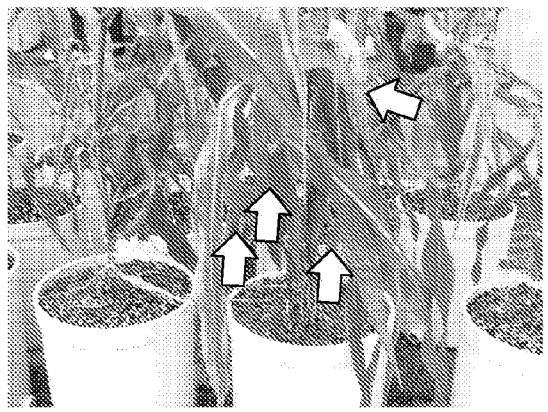
FIG. 32 is a drawing illustrating the results of examinations on the influence of oxidized glutathione on the crop yields of corn under a nitrogen-deficient condition.
Figure 32:
Figure 32:

As shown in (a) and (b) of FIG. 32, the plants thus obtained exhibited a larger amount of fruits than the plants that were not treated with GSSG in (c) of FIG. 32.

In order to examine the amount of production of the plants in more detail, the amounts of biomass of fruits, ground parts, and portions other than the fruits were measured, and harvest index was calculated.

Figure 33:
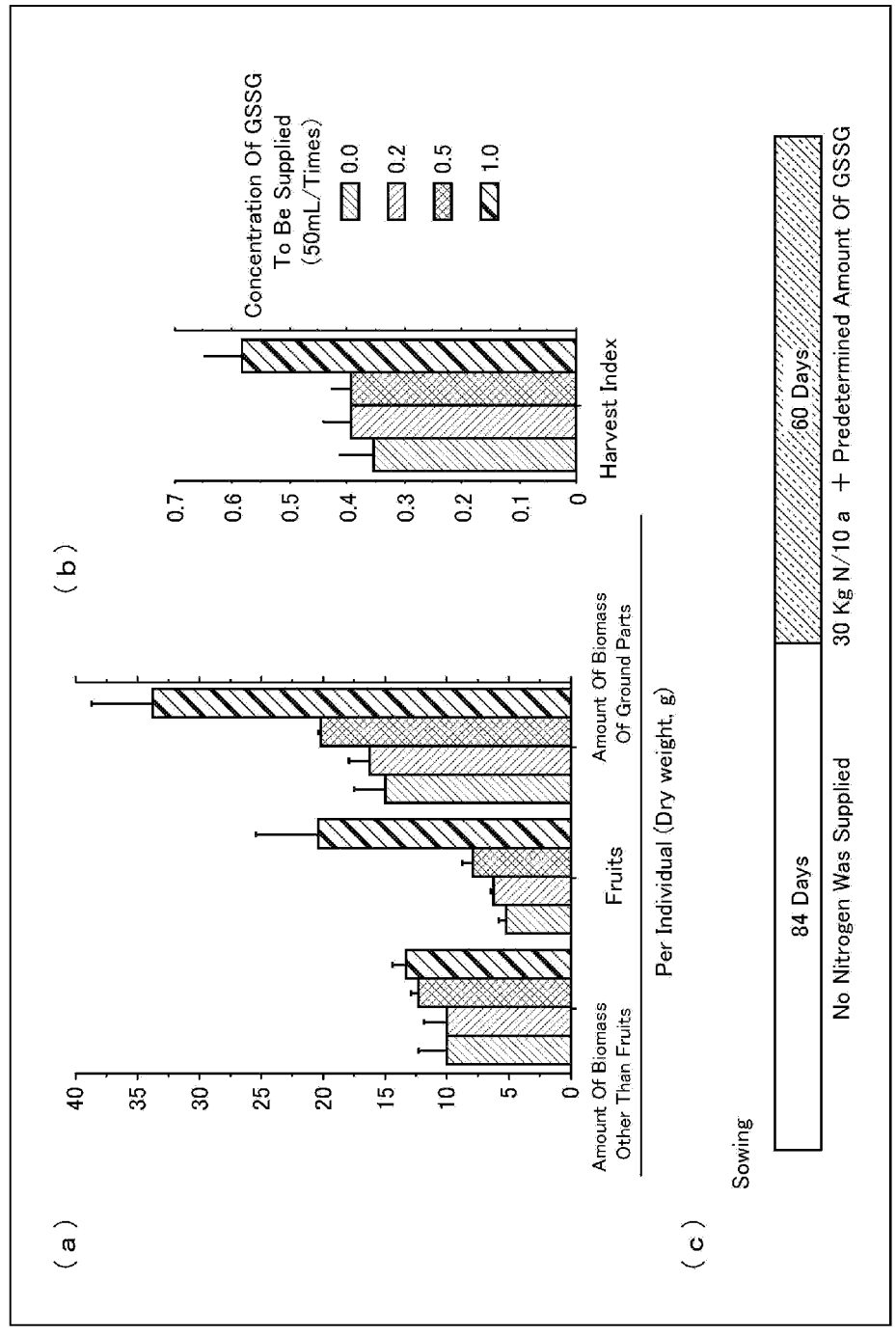
FIG. 33 is a drawing illustrating the results of examinations on the influence of oxidized glutathione on the amounts of biomass and the harvest index of fruits, ground parts, and portions other than the fruits of individual corns under a nitrogen-deficient condition.

As shown in (a) and (b) of FIG. 33, the results of the measurement and the calculation showed that the plants treated with GSSG exhibited larger amounts of biomass of fruits, ground parts, and portions other than the fruits and harvest index than the plants that were not treated with GSSG.

The above results clearly shows that when growth of a plant is restricted due to deficiency in nitrogen in vegetative development, the yield of fruits normally drops, but the treatment with GSSG allows preventing the yield from dropping even after the growth of the plant was restricted due to the deficiency in nitrogen.

<20. Effect 1 of Oxidized Glutathione on Promoting Growth of Sprout and Floral Bud of Rose>

Rose saplings (breed; Purple rose) were purchased at a hardware store and cultivated in pods for rice hydroponics. The rose saplings were fertilized with 50 mL of a 0.5 mM-GSSG solution in the form of a liquid fertilizer two times a week. In addition to GSSG, the rose saplings were additionally fertilized with 2 g of S604 every two weeks.

Figure 34:
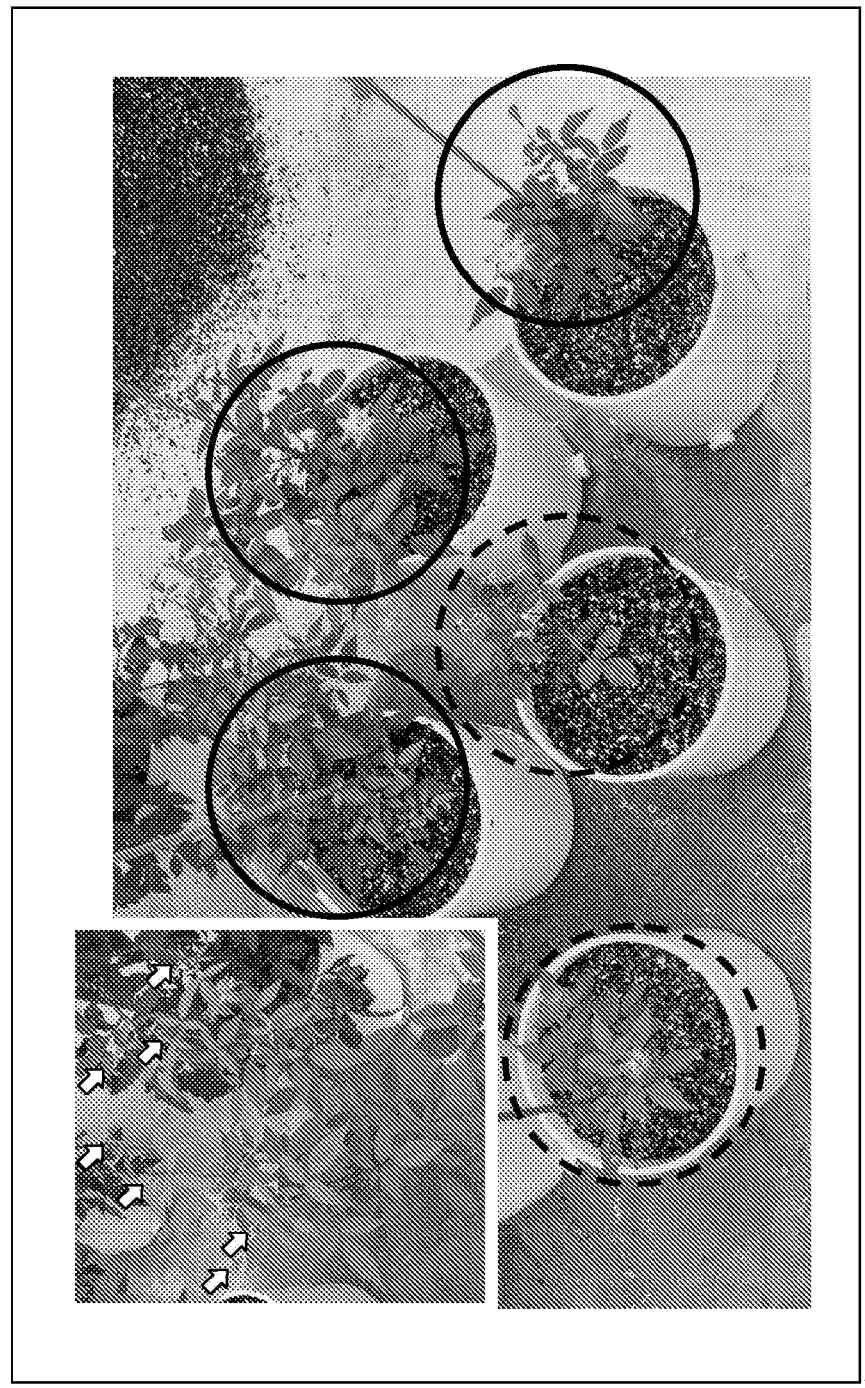
FIG. 34 is a drawing illustrating the result of examination on the influence of oxidized glutathione on growth of sprout and anthesis of a rose (breed; Purple rose).

Consequently, the plants treated with GSSG (plants surrounded by full circles of FIG. 34) exhibited promoted growth of sprout at one month from the fertilization compared with the plants that were not treated with GSSG (plants surrounded by broken circles of FIG. 34).

The above result clearly shows that the treatment with GSSG promotes growth of sprouts and floral buds of roses (breed; Purple rose).

<21. Effect 2 of Oxidized Glutathione on Promoting Growth of Sprout and Floral Bud of Rose>

Rose saplings (breed; JJ scarlet and JJ apricot) were purchased at a hardware store and cultivated in pods for rice hydroponics. The rose saplings were fertilized with 50 mL of a 0.5 mM-GSSG solution in the form of a liquid fertilizer two times a week. In addition to GSSG, the rose saplings were additionally fertilized with 2 g of S604 every two weeks.

Figure 35:
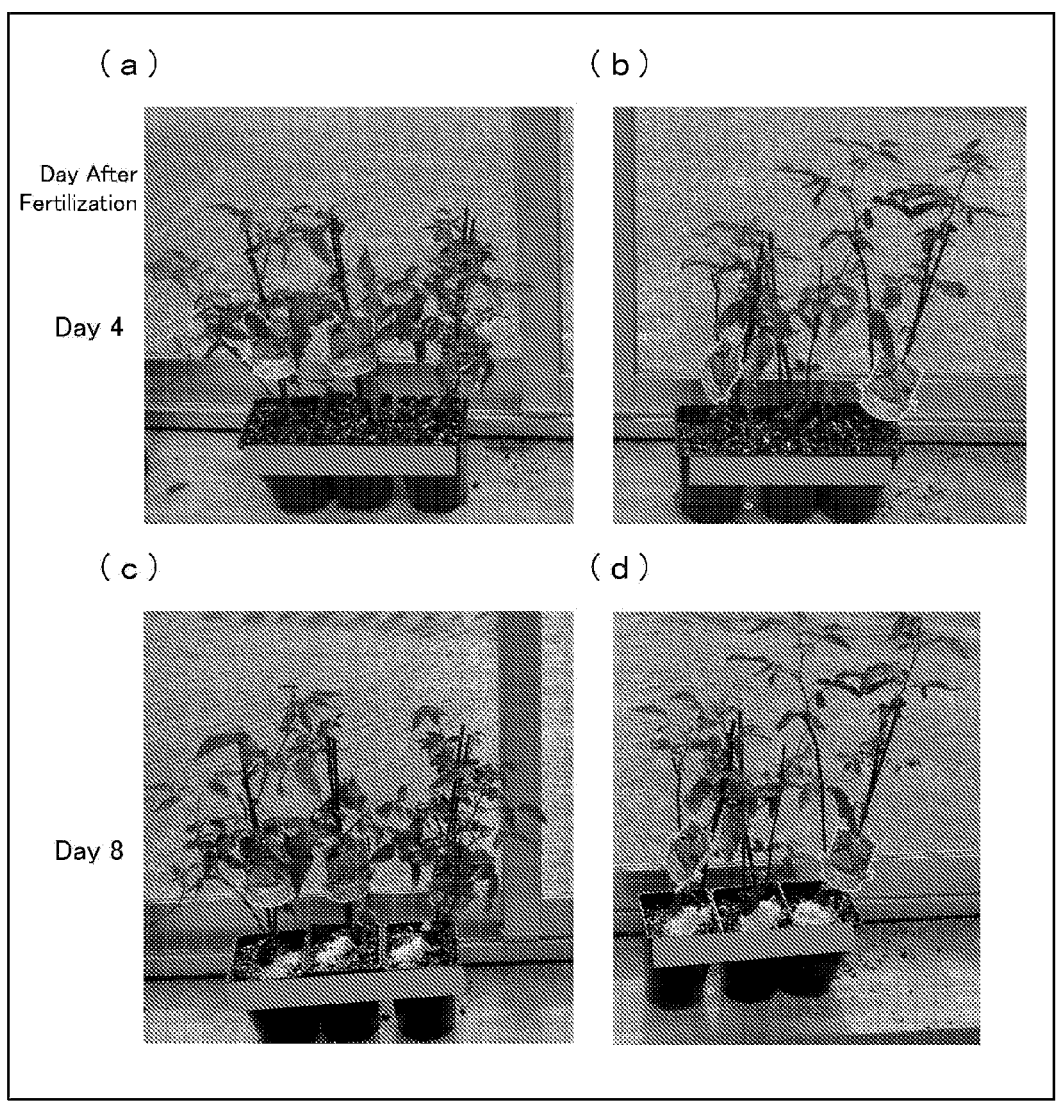
FIG. 35 is a drawing illustrating the result of examination on the influence of oxidized glutathione on growth of sprout and anthesis of a rose (breed; JJ scarlet and JJ apricot).

Consequently, the plants treated with GSSG ((a) and (c) of FIG. 35) exhibited promoted growth of sprout at fourth and eighth day from the fertilization compared with the plants that were not treated with GSSG ((b) and (d) of FIG. 35).

In (a)-(d) of FIG. 35, the breeds of three plants are JJ scarlet, JJ apricot, and JJ scarlet, respectively from the left.

<22. Effect of Oxidized Glutathione on Promoting Growth of Roots of Eustoma>

Seeds of eustoma were germinated in an MS culture medium containing 1 mM-GSSG or GSH, were grown for 1 month, and transferred to a planter. In the planter, 2 parts of vermiculite, 1 part of The Kureha Ikubyou Baido soil, and 1 part of vermiculite were layered as a lower layer, a middle layer, and an upper layer, respectively, and the above plants were transferred thereto.

Figure 36:
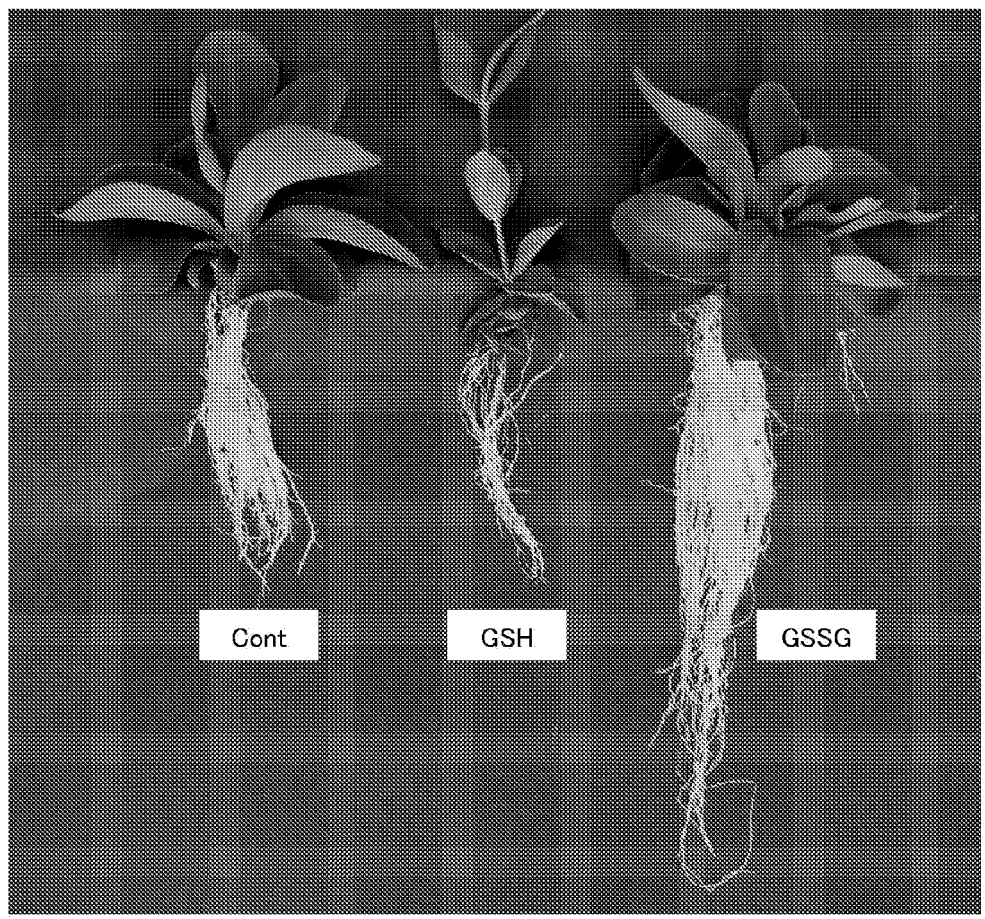
FIG. 36 is a drawing illustrating the results of examinations on the influences of oxidized glutathione and reduced glutathione on growth of roots of eustoma.

Consequently, as shown in FIG. 36, the plants treated with GSSG exhibited significant growth of roots compared with the plants that were not treated with GSSG. On the other hand, the plants treated with GSH exhibited subdued growth of roots compared with the plants that were not treated with GSSG.

<23. Effect 1 of Oxidized Glutathione on Promotion of Induction of Floral Bud of Rose>

Roses (breed; Patiohit alicante) were purchased at a hardware store and fertilized with 50 mL of a 0.5 mM-GSSG solution in the form of a liquid fertilizer two times a week. Approximately three and a half months later, plants in a GSSG-treated zone and plants in a non-GSSG-treated zone were compared with each other.

Figure 37:
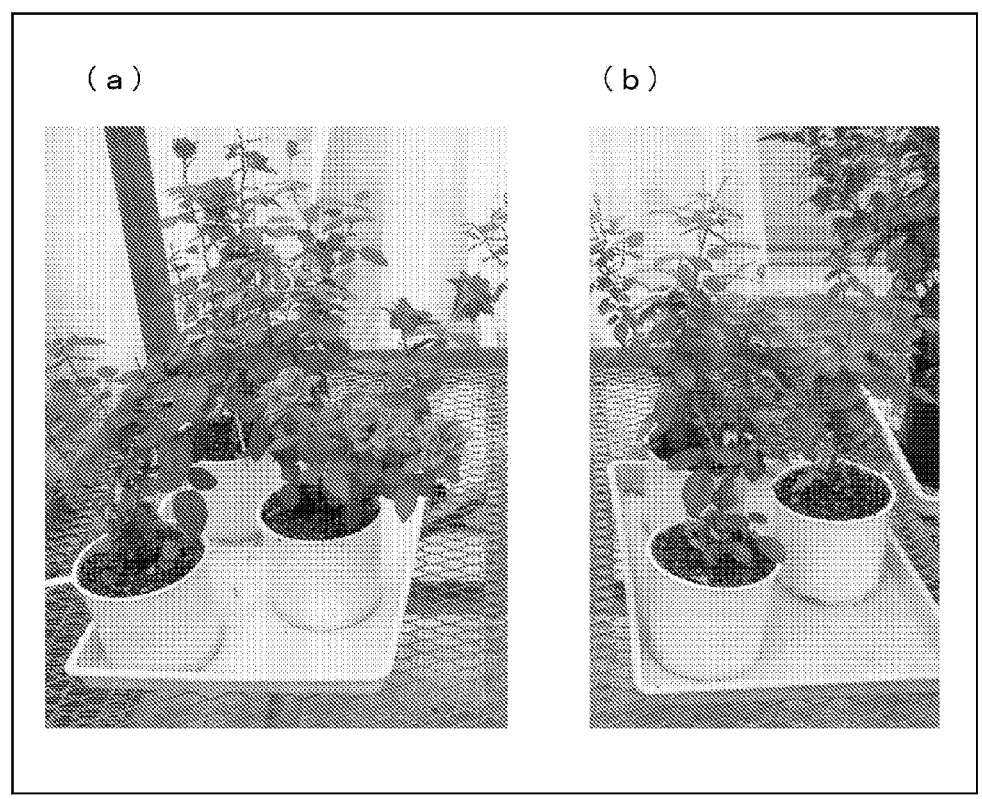
FIG. 37 is a drawing illustrating the results of examinations on the influence of oxidized glutathione on induction of floral buds of a rose.
Figure 38:
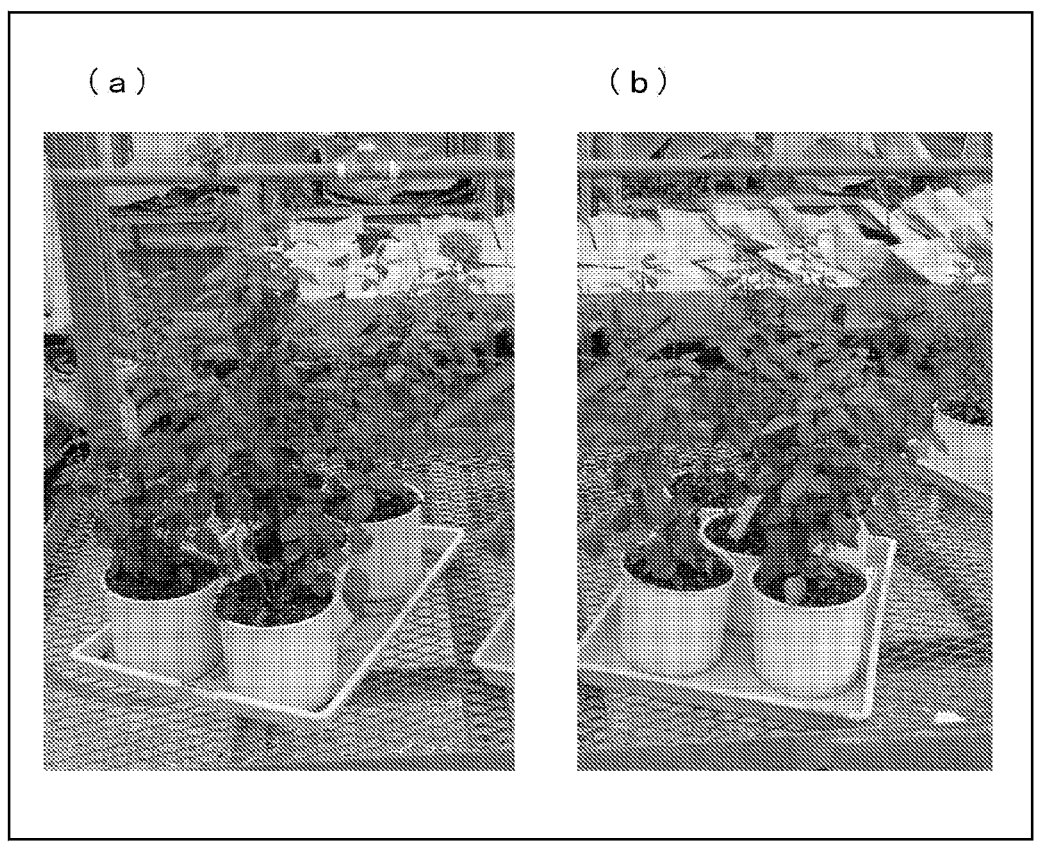
FIG. 38 is a drawing illustrating the results of examinations on the influence of oxidized glutathione on induction of floral buds of a rose.

Consequently, the plants treated with GSSG ((a) of FIG. 37 and (a) of FIG. 38) exhibited greatly larger number of bloomed flowers than the plants that were not treated with GSSG ((b) of FIG. 37 and (b) of FIG. 38).

The above results clearly show that oxidized glutathione promotes induction of floral buds of roses.

<24. Effect of Oxidized Glutathione on Growth of Strawberry>

A sapling of strawberry (breed; Eminent garden series, Yokubari-ichigo kurenai (SUMIKA)) was purchased at a hardware store and cultivated. The strawberry was fertilized with 50 mL of a 0.5 mM-GSSG solution in the form of a liquid fertilizer two times a week. In addition to GSSG, The strawberry was additionally fertilized with 2 g of S604 every two weeks.

Figure 39:
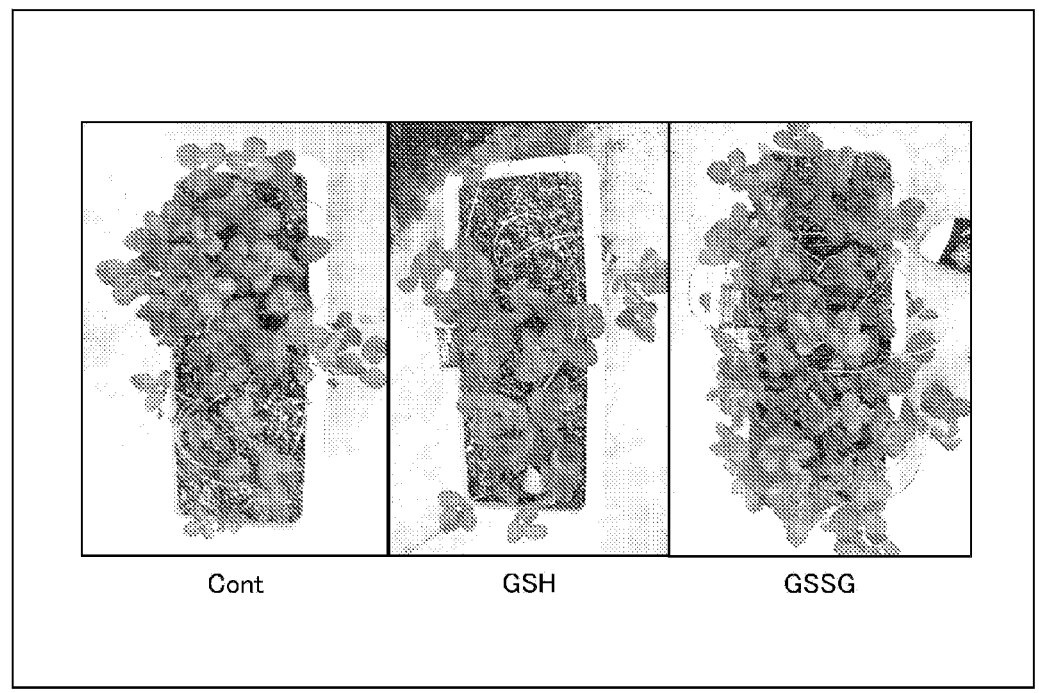
FIG. 39 is a drawing illustrating the results of examinations on the influences of oxidized glutathione and reduced glutathione on growth and multiplication (number of runners) of strawberry (Eminent garden series Yokubari-ichigo kurenai (SUMIKA)).

Consequently, as shown in FIG. 39, four months after the fertilization, a Cont zone (non-GSSG-treated zone) exhibited two or three runners per one stock, whereas a GSSG-treated zone exhibited a greatly large number of runners, i.e., several ten runners per one stock.

On the other hand, although a GSH-treated zone exhibited more number of runners per one stock than a Cont zone, the increase in the number of runners of the GSH-treated zone was approximately one third of the increase in the number of runners of the GSSG-treated zone.

The above results show that oxidized glutathione promotes growth of strawberry and increases the number of runners, promoting proliferation of stocks.

<25. Influence 1 of Oxidized Glutathione on Growth of Transformant *Arabidopsis* to which a Gene Encoding gFBA is Introduced>

Initially, transformants of *Arabidopsis* to which a gone encoding glutathione-binding plastid-type fructose-1,6-bisphosphate aldolase (which may be hereinafter referred to as "gFBA") was introduced and wild-type *Arabidopsis* (Columbia; Col) were cultivated under the same conditions as those in <1. Influence of oxidized glutathione on growth of *Arabidopsis*> except that the transformants of *Arabidopsis* and the wild-type *Arabidopsis* were fertilized with a liquid of 0 mM-, 3 mM, 9 mM-, or 18 mM-ammonium nitrate in the amount of 25 mL per three individuals one time a week.

Figure 40:
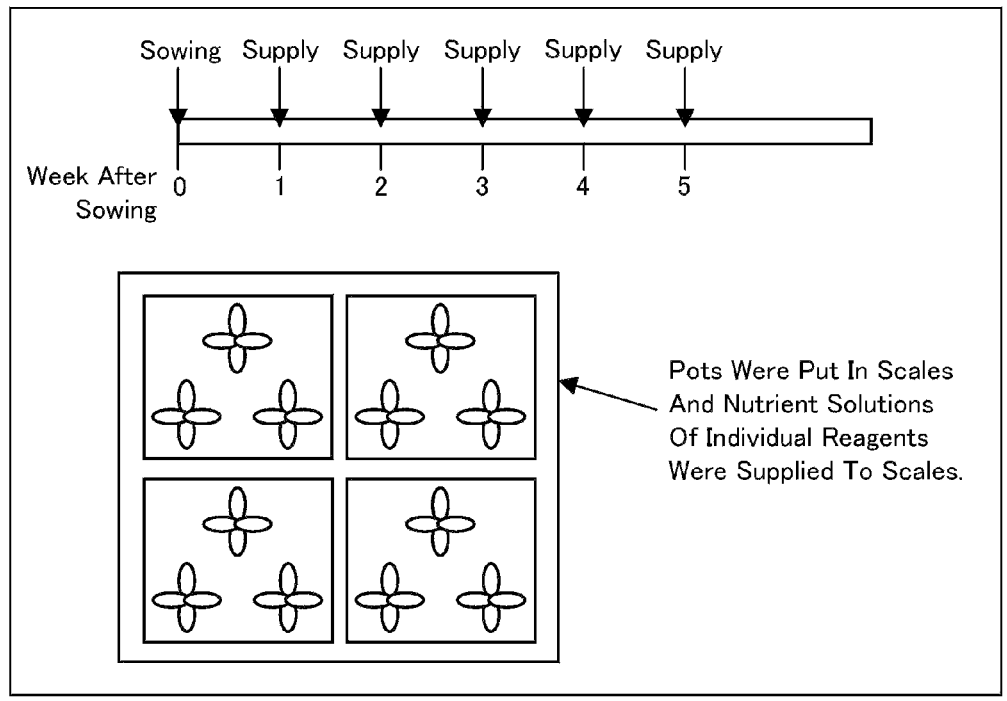
FIG. 40 is a drawing illustrating positions of individual plants in cultivation and a time of supplying oxidized glutathione in a test in which the influence of oxidized glutathione on growth of transformants of *Arabidopsis* to which a gFBA gene is introduced is examined.

The fertilization was performed in such a manner that a pot was put in a scale and an ammonium nitrate solution was poured in the scale. As for conditions for cultivating a plant, see FIG. 40.

Figure 41:
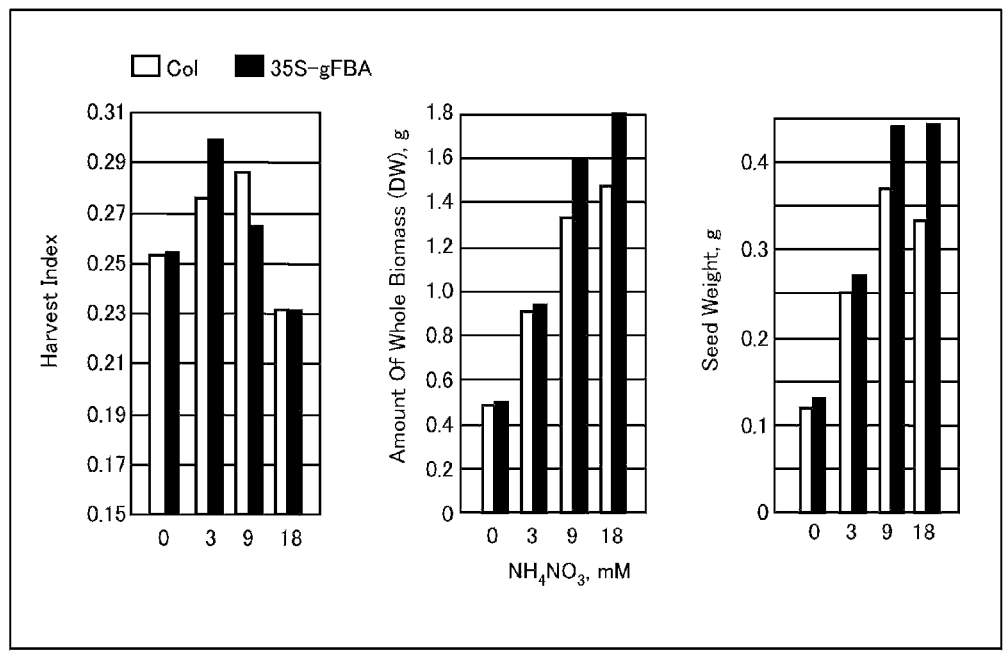
FIG. 41 is a drawing illustrating the results of examinations on concentration of ammonium nitrate at which the effects of increasing the harvest index, the whole amount of biomass, and the seed weight of wild-type *Arabidopsis* and transformants of *Arabidopsis* to which a gFBA1 gene is introduced are saturated.

The whole amount of biomass and the seed weight of the plants thus obtained were measured and harvest index was calculated. Consequently, as shown in FIG. 41, in any of the plants, the whole amount of biomass and the seed weight increased as concentration of ammonium nitrate used as a fertilizer increased, but the increase slowed down at 9 mM, and the effect was saturated at 18 mM.

On the other hand, in any of the plants, when 3 mM- and 9 mM-ammonium nitrate were used as fertilizers, the harvest index increased. However, when 18 mM-ammonium nitrate was used as a fertilizer, the harvest index dropped lower than the harvest index in a case of using no fertilizer. Such drop in harvest index was generally seen when nitrogen was excessively used as a fertilizer. In this case, as a fertilization amount N gets further higher, the drop in harvest is observed. In a case of crops, in order to avoid reduction of crop yields due to excessive fertilization, agricultural experimental stations and nursery companies disclose information on a standard fertilization amount N most suitable for crop yields.

Under fertilization conditions (18 mM-ammonium nitrate) where the effect of increasing crop yields was saturated with respect to the fertilization amount N, the effect of supplying GSSG was compared with the case of supplying no GSSG. The transformants of *Arabidopsis* to which a gene encoding gFBA was introduced and the wild-type *Arabidopsis* (Columbia; Col) were fertilized with only 1 mM-GSSG, or only 18 mM-ammonium nitrate, or both 18 mM-ammonium nitrate and 1 mM-GSSG in the form of a liquid fertilizer in the same manner as fertilization with ammonium nitrate in FIG. 41, and cultivated.

Figure 42:
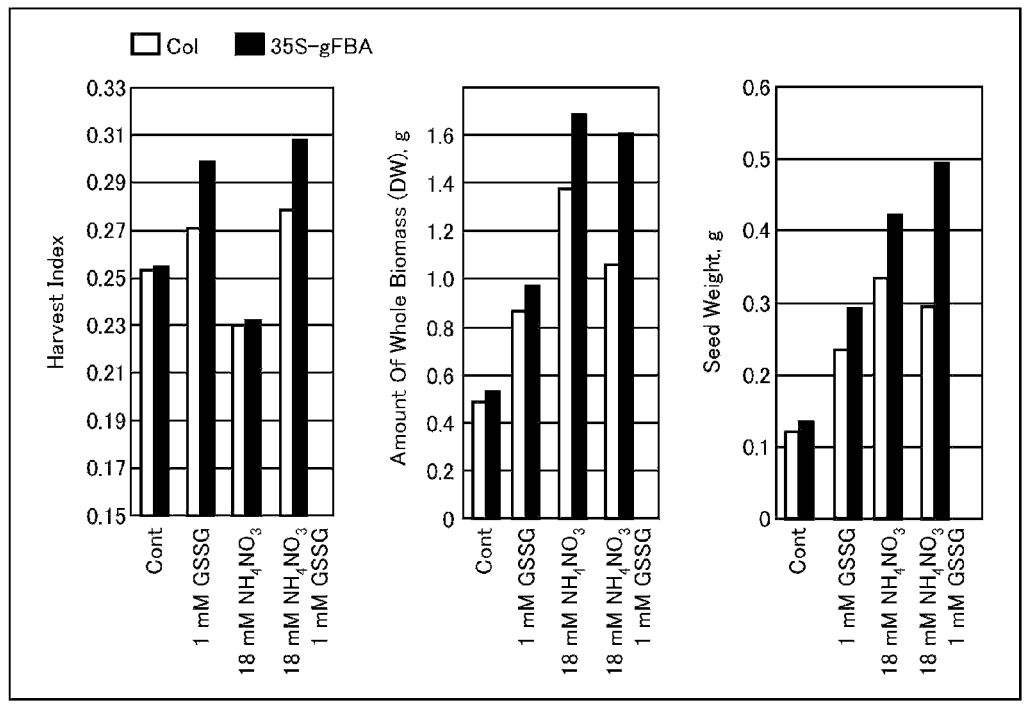
FIG. 42 is a drawing illustrating the results of examinations on the influence of oxidized glutathione on the harvest index, the whole amount of biomass, and the seed weight of transformants to which a gFBA gene is introduced, under a condition where the effect of nitrogen fertilization is saturated.

The whole amount of biomass and the seed weight of the plants thus obtained were measured and harvest index was calculated. Consequently, as shown in FIG. 42, fertilization with only oxidized glutathione increased any of the harvest index, the whole amount of biomass, and the seed weight, and the effect of oxidized glutathione was observed under conditions where the effect of ammonium nitrate on growth of the seed weight was saturated.

Combination of oxidized glutathione and ammonium nitrate resulted in a greater effect in the transformants to which the gene encoding gFBA was introduced than in the wild-type.

The above results show that supplying combination of oxidized glutathione and ammonium nitrate to the transformants to which the gene encoding gFBA was introduced allows further enhancing the effect of GSSG on increasing the harvest index, the whole amount of biomass, and the seed weight.

<26. Influence 2 of Oxidized Glutathione and Reduced Glutathione on Growth of Transformant *Arabidopsis* to which a Gene Encoding gFBA is Introduced>

Under the conditions in FIG. 42, instead of 1 mM-GSSG, GSH or ammonium sulfate was supplied in the same amount in terms of the N amount, and the effect of GSH or ammonium sulfate was compared with the effect of GSSG. Transformants of *Arabidopsis* to which a gene encoding gFBA was introduced and wild-type *Arabidopsis* (Columbia; Col) were cultivated in the same manner as in FIGS. 41 and 42 except for a condition concerning a liquid fertilizer. As the liquid fertilizer, 18 mM-ammonium nitrate, 18 mM-ammonium nitrate+1 mM-GSSG, 18 mM-ammonium nitrate+2 mM-GSH, or 18 mM-ammonium nitrate+2 mM-ammonium sulfate was used.

The fertilization was performed in such a manner that a pot was put in a scale and the above liquid fertilizer was poured in the scale. As for a condition for cultivating a plant, see FIG. 40.

Figure 43:
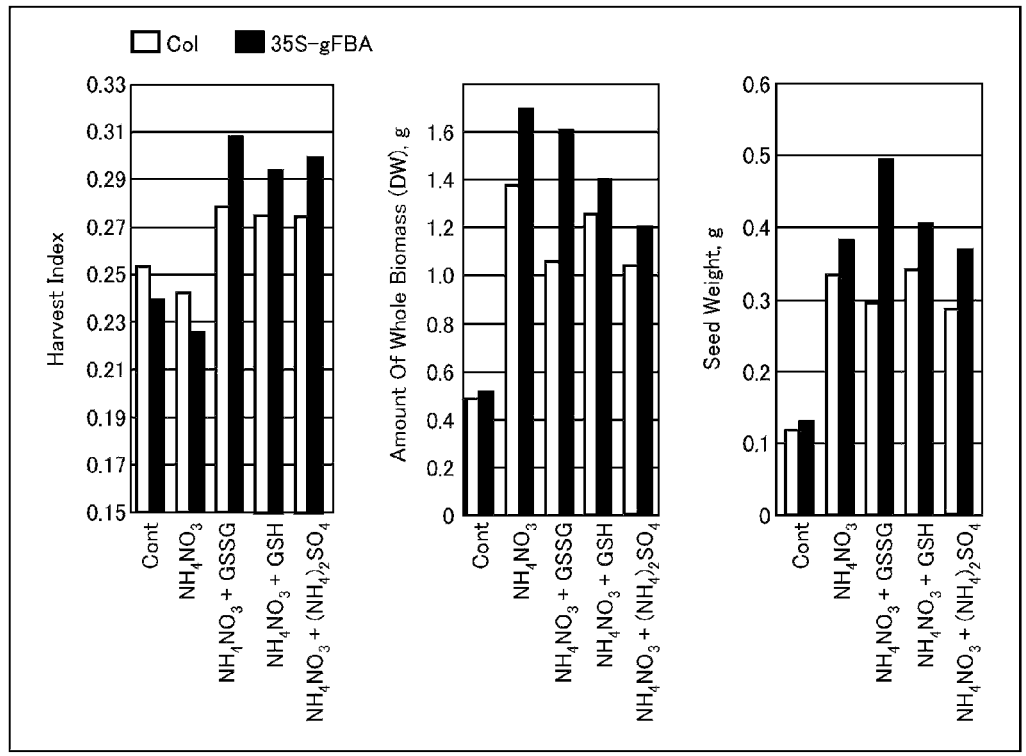
FIG. 43 is a drawing illustrating the results of examinations on the influences of oxidized glutathione, reduced glutathione, and ammonium sulfate on the harvest index, the whole amount of biomass, and the seed weight of transformants of *Arabidopsis* to which a gFBA gene is introduced, under a condition where the effect of nitrogen fertilization is saturated.

The whole amount of biomass and the seed weight of the plants thus obtained were measured and harvest index was calculated. Consequently, as shown in FIG. 43, supplying combination of oxidized glutathione and ammonium nitrate to the transformants to which the gFBA gene was introduced allows greatly increasing the harvest index, the whole amount of biomass, and the seed weight, compared with a case of treating the transformants in other manner.

As for the harvest index, although combination of reduced glutathione and ammonium nitrate resulted in an effect that was not so great as the effect of combination of oxidized glutathione and ammonium nitrate, the combination of reduced glutathione and ammonium nitrate greatly increased the harvest index compared with a case of using no fertilizer or a case of using only ammonium nitrate as a fertilizer.

The above results showed that both of oxidized glutathione and reduced glutathione allow greatly increasing the harvest index and significantly increasing crop yields when combined with ammonium nitrate. Further, the above results showed that the effect increased when the combination was supplied to plants to which the gFBA gene was introduced. Further, the above results showed that oxidized glutathione had a higher ability to increase the harvest index and to significantly increase crop yields than reduced glutathione.

<27. Influence 3 of Oxidized Glutathione on Growth of Transformant of *Arabidopsis* to which gFBA is Introduced>

Under the conditions similar to those in FIGS. 41-43 except that only GSSG was supplied as a liquid fertilizer, transformants of *Arabidopsis* to which the gFBA gene was introduced and wild-type *Arabidopsis* (Columbia; Col) were cultivated. Concentration of GSSG supplied as the liquid fertilizer varied from 0 mM to 5 mM.

Figure 44:
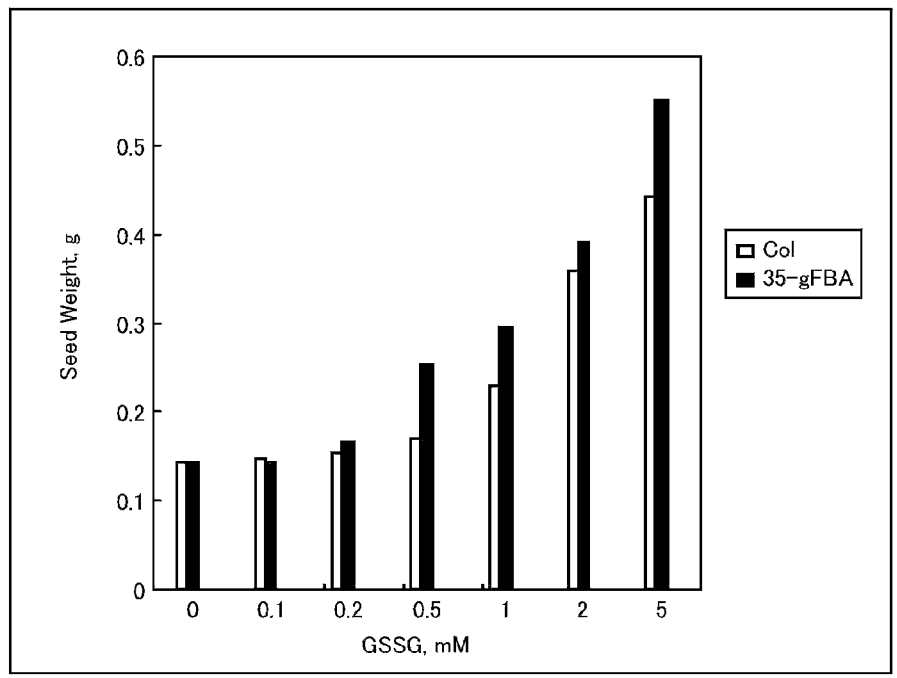
FIG. 44 is a drawing illustrating the result of examination on the influence of concentration of GSSG as a fertilizer on the yields of seeds of transformants of *Arabidopsis* to which a gFBA gene is introduced and wild-type *Arabidopsis*.
Figure 45:
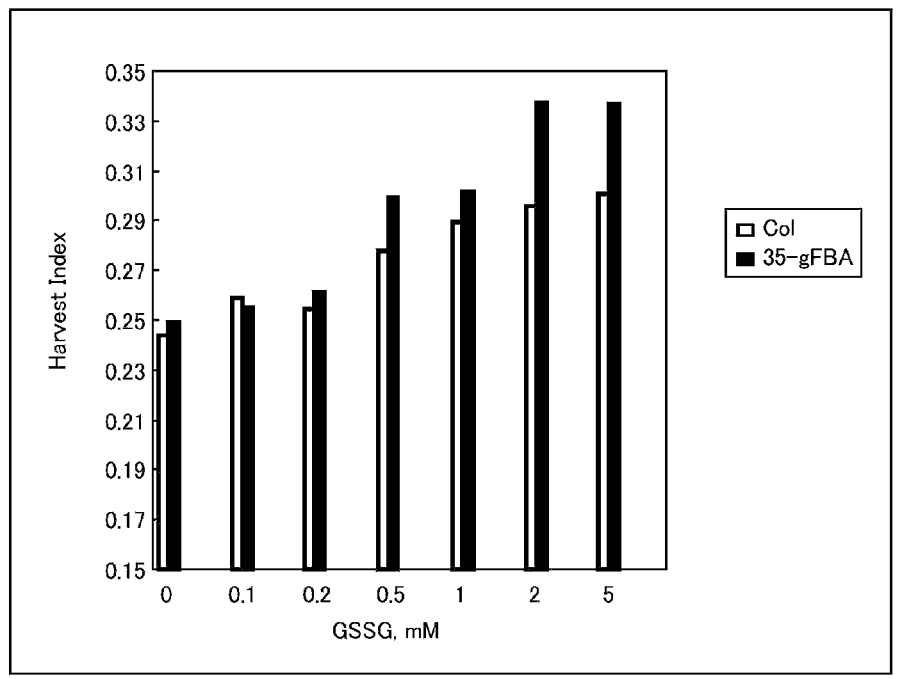
FIG. 45 is a drawing illustrating the result of examination on the influence of concentration of GSSG as a fertilizer on the harvest index of transformants of *Arabidopsis* to which a gFBA gene is introduced and wild-type *Arabidopsis*.

The whole amount of biomass and the seed weight of the plants thus obtained were measured and harvest index was calculated. The result of the seed weight was shown in FIG. 44 and the result of the harvest index was shown in FIG. 45. The seed weight increased as concentration of GSSG increased, and the effect was not saturated at the tested concentration. This tendency was more clearly observed in the transformants of *Arabidopsis* to which the gFBA gene was introduced.

On the other hand, the harvest index increased as concentration of GSSG increased, and the effect was saturated when the concentration of GSSG was approximately 2 mM. The effect of increasing the seed weight and the effect of increasing the harvest index that were yielded by the treatment with GSSG were greatly larger than the maximum effects yielded by fertilization with nitrogen resulting from ammonium nitrate.

The above results showed that the effect of increasing the seed weight and the effect of increasing the harvest index that were yielded by GSSG are greater than the effects yielded by ammonium nitrate and enhancing the gFBA gene allows increasing the effects.

<28. Comparisons of Influences of Oxidized Glutathione, Reduced Glutathione, and Ammonium Sulfate as Sulfur Sources on Growth>

Figure 46:
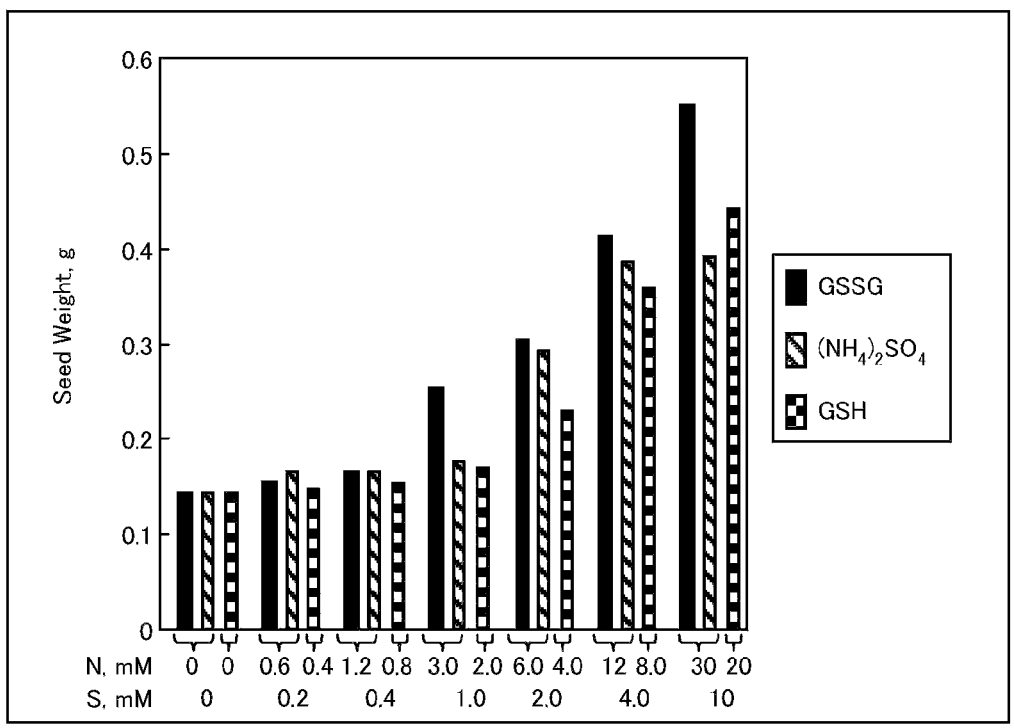
FIG. 46 is a drawing illustrating the results of examinations on the influences of fertilization with GSSG, GSH, and ammonium sulfate as sulfate sources on the yield of seeds of transformants of *Arabidopsis* to which a gFBA gene is introduced.
Figure 47:
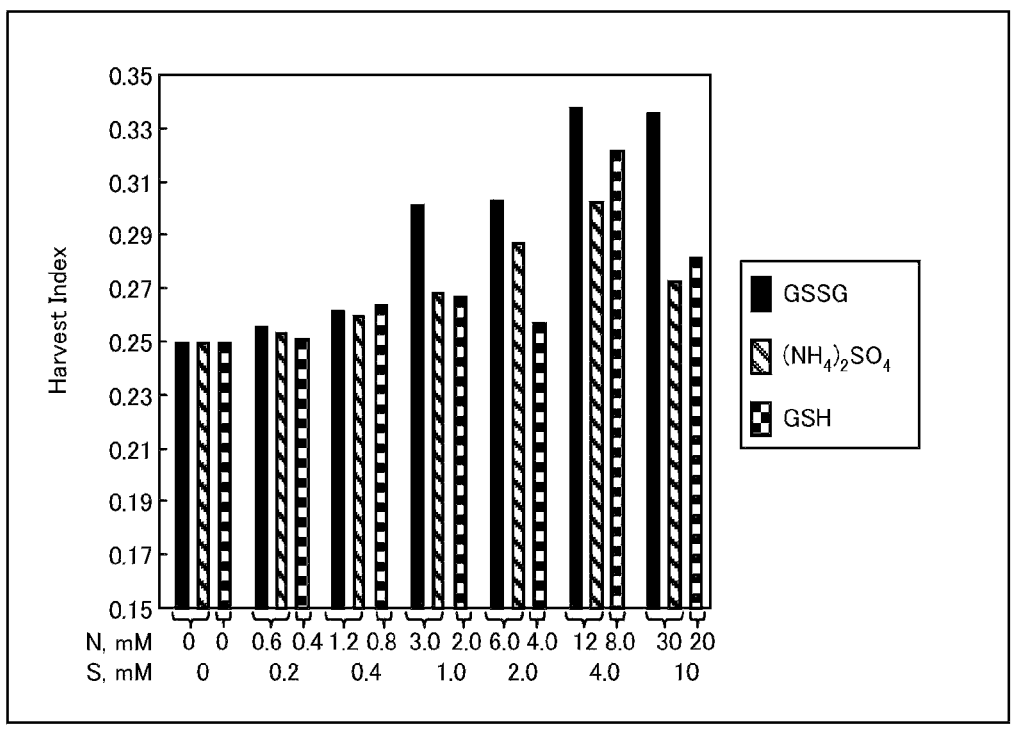
FIG. 47 is a drawing illustrating the results of examinations on the influences of fertilization with GSSG, GSH, and ammonium sulfate as sulfate sources on the harvest index of transformants of *Arabidopsis* to which a gFBA gene is introduced.

Under the conditions similar to those in FIGS. 41-45 except that any of GSSG, GSH, and ammonium sulfate was supplied as a liquid fertilizer, the effects of the liquid fertilizers on growth of transformants to which the gFBA gene was introduced were compared. The amounts of respective liquid fertilizers were set so that concentrations of the liquid fertilizers were the same in terms of an S amount. The seed weight and the whole amount of biomass of the plants thus obtained were measured and harvest index was calculated. The result of the seed weight was shown in FIG. 46 and the result of the harvest index was shown in FIG. 47.

The effect of ammonium sulfate generally used as a nitrogen fertilizer on increasing the seed weight was saturated at a value similar to that of the effect of ammonium nitrate. On the other hand, the effects of GSSG and GSH were not saturated at tested concentrations, indicating that GSSG and GSH yield higher effects of increasing the seed weight than ammonium sulfate. On the other hand, in any of the liquid fertilizers, the effect of increasing the harvest index reached its maximum when the N amount was 12 mM. Among the three liquid fertilizers, GSSG yielded the highest effect.

The above results showed that the effect of glutathione is higher than that of a conventional fertilizer and GSSG yields a higher effect than GSH.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

The present invention allows increasing harvest index of a plant. Further, the present invention allows increasing the number of seeds or flowers of the plant. Further, the present invention allows increasing lateral shoots and tillers and increasing the yield of seeds. Therefore, the present invention allows increasing the number of flowers and yields not only in ornamental flowering grasses and plants to be eaten but also in forests and plant resources for biomass energy. Therefore, the present invention has wide industrial applicability not only in agriculture but also food industries and energy industries.

The invention claimed is:

1. A method for preparing a plant having increased harvest index compared to a harvest index of a wild strain, or untreated plant, comprising:
   applying reduced glutathione to a plant, or to soil in which a plant is to be cultivated;
   cultivating the plant;
   measuring the amount of harvest of the plant;
   calculating harvest index of the plant; and
   selecting a plant having a harvest index that is higher than the harvest index of a wild strain or untreated plant;
   wherein a total amount of the reduced glutathione with which the plant is cultivated is in the range (i) between 2.6 mg and 128.1 mg per one individual said plant or (ii) between 36.4 mg and 1820.9 mg per one liter of the soil.

2. The method as set forth in claim 1, wherein the reduced glutathione is applied intermittently.

3. The method as set forth in claim 1, wherein the reduced glutathione is applied at around a time of transition from vegetative to reproductive development.

4. The method as set forth in claim 1, wherein the plant has a mutation in a function for synthesizing a plant hormone and/or a function for responding to a plant hormone.

5. The method as set forth in claim 4, wherein the plant hormone is gibberellin.

6. The method as set forth in claim 1, wherein the amount of harvest is selected from the group consisting of: a weight of harvest, number of harvest, and amount of biomass of the harvest.

7. The method as set forth in claim 6, wherein the harvest is at least one selected from the group consisting of: fruit, seed, stem, root, flower and leaves.

8. The method as set forth in claim 1, wherein applying reduced glutathione to the plant or to the soil comprises applying the reduced glutathione at a time ranging from a time of transition from vegetative to reproductive development to the about a time of bolting.

9. The method as set forth in claim 1, wherein the plant is a mutant or transformant plant.

10. The method as set forth in claim 9, wherein the plant is a transformant plant to which a gene for encoding glutathione-binding plastid-type fructose-1,6- bisphosphate aldolase (gFBA) is introduced.

11. A method for preparing a plant having increased number of seeds and/or flowers compared to a number of seeds and/or flowers of a wild strain or untreated plant, comprising:
    applying reduced glutathione to a plant, or to soil in which a plant is to be cultivated; cultivating the plant;
    measuring the number of seeds and and/or the flowers of the plant; and
    selecting a plant having a number of seeds and/or flowers that is higher than the number of seeds and/or flowers of a wild strain or untreated plant;
    wherein a total amount of the reduced glutathione with which the plant is cultivated is in the range (i) between 2.6 mg and 128.1 mg per one individual said plant or (ii) between 36.4 mg and 1820.9 mg per one liter of the soil.

12. A method for preparing a plant having increased number of lateral shoots and/or tillers compared to a number of lateral shoots and/or tillers of a wild strain or untreated plant, comprising:
    applying reduced glutathione to a plant, or to soil in which a plant is to be cultivated;
    cultivating the plant;
    measuring the number of lateral shoots and/or tillers of the plant; and
    selecting a plant having a number of lateral shoots and/or tillers that is higher than the number of lateral shoots and/or tillers of a wild strain or untreated plant;
    wherein a total amount of the reduced glutathione with which the plant is cultivated is in the range (i) between 2.6 mg and 128.1 mg per one individual said plant or (ii) between 36.4 mg and 1820.9 mg per one liter of the soil.

13. The method as set forth in claim 12, wherein applying reduced glutathione to the plant or to the soil comprises applying the reduced glutathione intermittently.

14. The method as set forth in claim 12, wherein applying reduced glutathione to the plant or to the soil comprises applying the reduced glutathione at about a time the plant transitions from vegetative to reproductive development.

* * * * *